(12) United States Patent
Takahashi et al.

(10) Patent No.: US 9,951,060 B2
(45) Date of Patent: Apr. 24, 2018

(54) 2-ACYLAMINOTHIAZOLE DERIVATIVE OR SALT THEREOF

(71) Applicant: ASTELLAS PHARMA INC., Chuo-ku (JP)

(72) Inventors: Taisuke Takahashi, Tokyo (JP); Takanori Koike, Tokyo (JP); Kenji Negoro, Tokyo (JP); Hiroaki Tanaka, Tokyo (JP); Jun Maeda, Tokyo (JP); Kazuhiro Yokoyama, Tokyo (JP); Hajime Takamatsu, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/316,645

(22) PCT Filed: Jun. 5, 2015

(86) PCT No.: PCT/JP2015/066321
§ 371 (c)(1),
(2) Date: Dec. 6, 2016

(87) PCT Pub. No.: WO2015/186821
PCT Pub. Date: Dec. 10, 2015

(65) Prior Publication Data
US 2017/0197955 A1  Jul. 13, 2017

(30) Foreign Application Priority Data

Jun. 6, 2014 (JP) .................. 2014-118046

(51) Int. Cl.
*A61K 31/497* (2006.01)
*C07D 417/14* (2006.01)

(52) U.S. Cl.
CPC .................. *C07D 417/14* (2013.01)

(58) Field of Classification Search
CPC .................................................. C07D 417/14
See application file for complete search history.

(56) References Cited

U.S. PATENT DOCUMENTS

| 2002/0049195 A1 | 4/2002 | Mammen et al. |
| 2005/0277676 A1 | 12/2005 | Laine et al. |
| 2006/0194844 A1 | 8/2006 | Sugasawa et al. |

FOREIGN PATENT DOCUMENTS

| JP | 2001-278872 A | 10/2001 |
| JP | 2003-516391 A | 5/2003 |
| JP | 2006-505517 A | 2/2006 |
| JP | 2006-219480 A | 8/2006 |
| JP | 2006-219481 A | 8/2006 |
| WO | 01/42213 A1 | 6/2001 |
| WO | 03/062233 A1 | 7/2003 |
| WO | 2004/012684 A2 | 2/2004 |
| WO | 2005/007651 A1 | 1/2005 |
| WO | 2014/133056 A1 | 9/2014 |
| WO | 2012/016217 A1 | 2/2015 |

OTHER PUBLICATIONS

Mansfield, K.J., Muscarinic receptor antagonists, the overactive bladder and efficacy against urinary urgency. Clinical Medicine Insights: Therapeutics, 2010, 2, 471-480.*
International Search Report dated Sep. 1, 2015, in PCT/JP2015/066321, filed Jun. 5, 2015.
Birdsall, et al., "Subtype-Selective Positive Cooperative Interactions Between Brucine Analogs and Acetylcholine at Muscarinic Receptors: Functional Studies", Molecular Pharmacology, vol. 55, 1999, pp. 778-786.
Lazareno, et al., "Analogs of WIN 62,577 Define a Second Allosteric Site on Muscarinic Receptors", Molecular Pharmacology, vol. 62, No. 6, 2002, pp. 1492-1505.
Tarasova, et al., "Modelling Atypical Small-Molecule Mimics of an Important Stem Cell Cytokine, Thrombopoietin", ChemMedChem, vol. 4, 2009, pp. 2002-2011.
Extended European Search Report dated Nov. 7, 2017 in Patent Application No. 15803484.3.
Office Action dated Feb. 16, 2018 issued in corresponding Colombian patent application NC2017/0000044 (with partial English translation).

* cited by examiner

*Primary Examiner* — Brian McDowell
(74) *Attorney, Agent, or Firm* — Oblon, McClelland, Maier & Neustadt, L.L.P.

(57) ABSTRACT

[Problem]
To provide a compound which is useful as an active ingredient for a pharmaceutical composition for preventing or treating urine storage dysfunction, voiding dysfunction, lower urinary tract dysfunction, and the like.
[Means for Solution]
The present inventors have found that a thiazole derivative substituted with pyrazinylcarbonylamino at the 2-position is an excellent muscarinic $M_3$ receptor-positive allosteric modulator and is expected as an agent for preventing or treating bladder/urinary tract diseases associated with bladder contractions via a muscarinic $M_3$ receptor, thereby completing the present invention. 2-Acylaminothiazole derivative or a salt thereof of the present invention is expected as an agent for preventing or treating bladder/urinary tract diseases associated with bladder contractions via a muscarinic $M_3$ receptor, for example voiding dysfunction such as underactive bladder.

17 Claims, No Drawings

2-ACYLAMINOTHIAZOLE DERIVATIVE OR SALT THEREOF

CROSS REFERENCE TO RELATED APPLICATION

This application is a National Stage entry under 35 USC 371 of PCT/JP2015/066321, filed on Jun. 5, 2015, and claims priority to Japanese Patent Application No. 2014-118046, filed on Jun. 6, 2014.

TECHNICAL FIELD

The present invention relates to a 2-acylaminothiazole derivative or a salt thereof which is useful as an active ingredient for a pharmaceutical composition, in particular, a pharmaceutical composition for treating bladder/urinary tract diseases related to bladder contractions via a muscarinic $M_3$ receptor.

BACKGROUND ART

The important roles of the lower urinary tract are urine storage and voiding, which are regulated by a coordinated action of the bladder and the urethra. That is, during urine storage, the bladder smooth muscle is relaxed and the urethral sphincter is contracted, whereby a state in which urethral resistance is high is maintained and urinary continence is maintained. On the other hand, during voiding, the bladder smooth muscle is contracted, the urethra smooth muscle is relaxed, and contraction of the external urethral sphincter is also inhibited. Examples of the lower urinary tract disorder include urine storage dysfunction such as overactive bladder, in which urine cannot be retained during urine storage, and voiding dysfunction, in which urine cannot be drained sufficiently during voiding due to an increase in the urethral resistance or a decrease in the bladder contractile force. These two disorders may develop simultaneously in some cases.

Voiding dysfunction is caused by a decrease in the bladder contractile force or an increase in urethral resistance during voiding, and causes difficulty in voiding, straining during voiding, a weak urine stream, extension of voiding time, an increase in residual urine, a decrease in voiding efficiency, or the like. The decrease in the bladder contractile force during voiding is referred to as underactive bladder, acontractile bladder, or the like. As a factor causing such a decrease in the bladder contractile force during voiding, for example, aging, diabetes mellitus, benign prostatic hyperplasia, neurological diseases such as Parkinson's disease and multiple sclerosis, spinal cord injury, neurological disorders by pelvic surgery, and the like have been known (Reviews in Urology, 15: pp. 11-22 (2013)).

As a mechanism to cause bladder contraction during voiding, involvement of muscarinic receptor stimulation has been known. That is, during urination, the pelvic nerve which is a parasympathetic nerve governing the bladder is excited to release acetylcholine from nerve terminals. The released acetylcholine binds to a muscarinic receptor present in the bladder smooth muscle to cause contraction of the bladder smooth muscle (Journal of Pharmacological Sciences, 112: pp. 121-127 (2010)). The muscarinic receptors are currently classified into five subtypes, $M_1$, $M_2$, $M_3$, $M_4$, and $M_5$, and it has been known that the subtypes involving the contraction in the bladder smooth muscle is mainly $M_3$ (Pharmacological Reviews, 50: pp. 279-290 (1998); The Journal of Neuroscience, 22: pp. 10627-10632 (2002)).

As a therapeutic drug for a decrease in bladder contractile force during voiding, bethanechol chloride which is a non-selective muscarinic receptor agonist and distigmine bromide which is a cholinesterase inhibitor have been known. However, it has been known that these drugs have cholinergic side effects such as diarrhea, abdominal pain, and perspiration. In addition, there may be cases where cholinergic crisis is occurred as a serious side effect, which require attention during use (Ubretid (registered trademark), tablet 5 mg, package insert, Torii Pharmaceutical Co., Ltd., and Besacholine (registered trademark) powder 5%, package insert, Eisai Co., Ltd.).

On the other hand, as a cause of an increase in urethral resistance, voiding dysfunction associated with benign prostatic hyperplasia has been well-known, which is characterized in that the urethra is partially occluded by nodular enlargement of the prostatic tissue. Currently, an adrenergic a, receptor antagonist has been used as a therapeutic drug for voiding dysfunction associated with benign prostatic hyperplasia (Pharmacology, 65: pp. 119-128 (2002)). On the other hand, the effectiveness of the adrenaline $\alpha_1$ receptor antagonist for voiding dysfunction that is not associated with benign prostatic hyperplasia is unclear, as compared with the effectiveness against voiding dysfunction that is associated with benign prostatic hyperplasia (Journal of Pharmacological Sciences, 112: pp. 121-127 (2010)).

Furthermore, for voiding dysfunction caused by a decrease in bladder contractile force or an increase in urethral resistance, residual urine after voiding may be observed in some cases. The increased residual urine may cause a decrease in effective bladder capacity, and thus cause overactive bladder symptoms such as urinary frequency or severe symptoms such as hydronephrosis in some cases.

There has been a demand for a more effective therapeutic drug for such bladder/urethral diseases due to a decrease in the bladder contractile force or an increase in urethral resistance during voiding, or symptoms thereof (Reviews in Urology, 15: pp. 11-22 (2013)).

Patent Document 1 discloses that a compound represented by the following general formula (A) including a compound of the formula (A1) below, which is disclosed in Example 315, has a Ba/F3 cell proliferative activity through a human c-myeloproliferative leukemia virus type P (c-Mpl), and has thrombocyte increasing activity.

[Chem. 1]

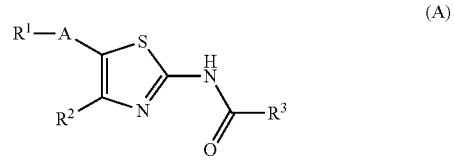

(A)

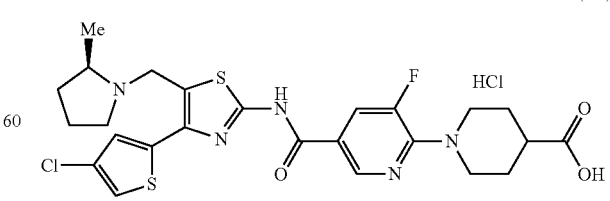

(A1)

(in which $R^3$ represents an aromatic hetero ring which may be substituted, or the like. For the other symbols, refer to the patent publication).

Patent Document 2 discloses that a compound represented by the following general formula (B) has an AMPK pathway activating action.

[Chem. 2]

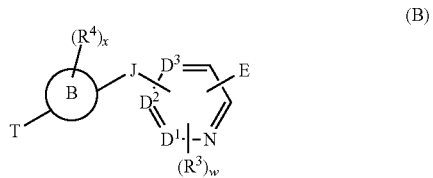

(B)

(in which Ring B represents a heteroarylene or the like, J represents —NR$^{13}$C(O)— or the like, D$^1$, D$^2$ and D$^3$ each represent N, CH, or the like, E represents —NR$^1$R$^2$ or the like, and R$^1$ and R$^2$ may be combined with an adjacent nitrogen atom to form a heterocycloalkyl which may be substituted. For the other symbols, refer to this publication).

Non-Patent Document 1 discloses that a compound represented by the following formula (C1) is an allosteric enhancer of a muscarinic M$_3$ receptor.

[Chem. 3]

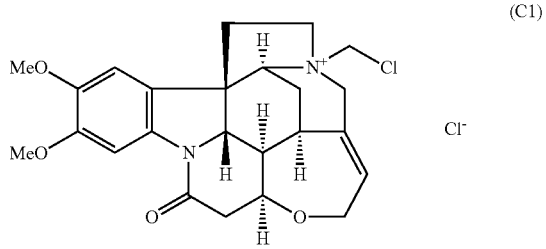

(C1)

Non-Patent Document 2 discloses that WIN 62,577 represented by the following formula is a rat NK1 receptor antagonist and, at the same time, an allosteric enhancer of a muscarinic receptor.

[Chem. 4]

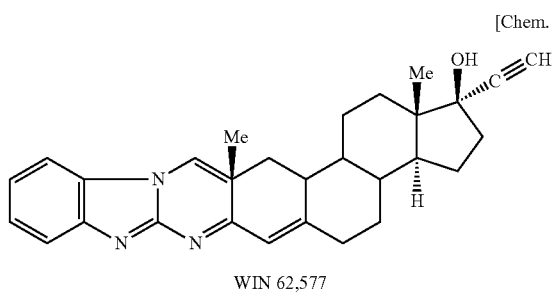

WIN 62,577

RELATED ART

Patent Document

[Patent Document 1] WO 2005/007651
[Patent Document 2] WO 2012/016217
[Non-Patent Document 1] Molecular Pharmacology, 55: pp 778-786 (1999)

[Non-Patent Document 2] Molecular Pharmacology, 62: pp 1492-1505 (2002)

DISCLOSURE OF INVENTION

Problems to be Solved by the Invention

The present invention provides a novel compound which is expected as an active ingredient for a pharmaceutical composition, in particular, for a pharmaceutical composition for preventing or treating bladder/urinary tract diseases associated with bladder contractions via a muscarinic M$_3$ receptor, which acts as a muscarinic M$_3$ receptor-positive allosteric modulator.

Means for Solving the Problems

The present inventors have found that a thiazole derivative substituted with pyrazinylcarbonylamino at the 2-position is an excellent muscarinic M$_3$ receptor-positive allosteric modulator and is expected as an agent for preventing or treating bladder/urinary tract diseases associated with bladder contractions via a muscarinic M$_3$ receptor, thereby completing the present invention.

That is, the present invention relates to a compound of the formula (I) or a salt thereof, and a pharmaceutical composition comprising a compound of the formula (I) or a salt thereof and an excipient.

[Chem. 5]

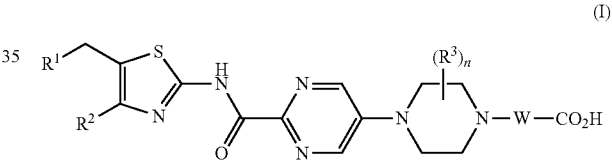

(I)

(wherein
R$^1$ is —N(—R$^{11}$)(—R$^{12}$), or cyclic amino which may be substituted,
R$^{11}$ is C$_{1-6}$ alkyl,
R$^{12}$ is C$_{1-6}$ alkyl which may be substituted, or C$_{3-8}$ cycloalkyl which may be substituted,
R$^2$ is aryl which may be substituted, monocyclic aromatic hetero ring which may be substituted, or bicyclic aromatic hetero ring which may be substituted,
R$^3$'s are the same as or different from each other, and are each C$_{1-6}$ alkyl,
W is C$_{1-6}$ alkylene, and
n is an integer of 0 to 4).

Further, unless specifically described otherwise, when symbols in one formula in the present specification are also used in other formulae, same symbols denote same meanings.

Further, Patent Document 1 does not disclose a specific compound which is a compound of the formula (A) wherein R$^3$ is pyrazinyl, and neither discloses nor suggests an action on a muscarinic receptor or an action on bladder/urethral diseases.

Furthermore, Patent Document 2 does not disclose a specific compound which is a compound of the formula (B) wherein ring B is thiazole, and neither discloses nor suggests an action on a muscarinic receptor or an action on bladder/urethral diseases.

Further, the present invention relates to a pharmaceutical composition comprising the compound of the formula (I) or a salt thereof, and a pharmaceutically acceptable excipient. Furthermore, the present invention relates to a pharmaceutical composition for preventing or treating bladder/urinary tract diseases associated with bladder contractions via a muscarinic $M_3$ receptor, comprising the compound of the formula (I) or a salt thereof. Furthermore, the present invention relates to an agent for preventing or treating bladder/urinary tract diseases associated with bladder contractions via a muscarinic $M_3$ receptor, comprising the compound of the formula (I) or a salt thereof.

Moreover, the present invention relates to use of the compound of the formula (I) or a salt thereof for the manufacture of a pharmaceutical composition for preventing or treating bladder/urinary tract diseases related to bladder contractions via a muscarinic $M_3$ receptor; use of the compound of the formula (I) or a salt thereof for preventing or treating bladder/urinary tract diseases related to bladder contractions via a muscarinic $M_3$ receptor, the compound of the formula (I) or a salt thereof for preventing or treating bladder/urinary tract diseases related to bladder contractions via a muscarinic $M_3$ receptor; and a method for preventing or treating bladder/urinary tract diseases related to bladder contractions via a muscarinic $M_3$ receptor, comprising administering to a subject an effective amount of the compound of the formula (I) or a salt thereof. Further, the "subject" is a human or a non-human animal in need of the prevention or treatment, and in one embodiment, a human in need of the prevention or treatment.

Effects of the Invention

The compound of the formula (I) or a salt thereof is a muscarinic $M_3$ receptor-positive allosteric modulator, and can thus be used as an agent for preventing or treating bladder/urinary tract diseases associated with bladder contractions via a muscarinic $M_3$ receptor.

EMBODIMENTS FOR CARRYING OUT THE INVENTION

Hereinafter, the present invention will be described in detail.

In general, the positive allosteric modulator is a compound which binds to an allosteric site different from a ligand binding site, and has an effect of increasing the affinity of an agonist to a receptor by mainly causing a structural change in a receptor, and thus changing the signal level of agonistic activity. In the living body, the positive allosteric modulator does not exhibit an agonistic effect by itself, and increases the effect of an endogenous agonist. Examples of the advantages of positive allosteric modulator over the agonists include (1) avoiding the side effects since the positive allosteric modulator exhibits an enhancement in the endogenous agonist stimulation dependently, (2) having a possibility of obtaining high subtype selectivity since the positive allosteric modulator binds to a site other than a ligand binding site, and (3) less probability of causing desensitization, which can be seen with the agonists (Pharmacological Reviews, 63: pp. 59-126 (2011)).

In the present specification, the muscarinic $M_3$ receptor-positive allosteric modulator means a compound which enhances an effect via the muscarinic $M_3$ receptor by an agonist stimulation-dependent or nerve stimulation-dependent manner. Accordingly, only during voiding, the effect on enhancing bladder contraction is expected and the muscarinic $M_3$ receptor-positive allosteric modulator is possibly useful as an agent for improving various symptoms associated with voiding dysfunction. Further, by such a specific action during voiding, it is expected that it is possible to avoid cholinergic side effects, known to be induced with bethanechol chloride and distigmine bromide. In addition, since the muscarinic $M_3$ receptor-positive allosteric modulator increases bladder contractile force during voiding, an effect in voiding dysfunction which is caused by an increase in urethral resistance can also be expected. A decrease in residual urine by such improvement of voiding dysfunction leads to an increase in the effective bladder capacity, and thus, it can be expected to improve urine storage functions as well as to avoid renal disorder. Thus, the muscarinic $M_3$ receptor-positive allosteric modulator is expected to be useful as an agent for preventing or treating bladder/urinary tract diseases related to bladder contractions via a muscarinic $M_3$ receptor. The present inventors have newly discovered a compound that acts as the modulator, thereby completing the present invention.

In the present specification, examples of the "bladder/urinary tract diseases associated with bladder contractions via a muscarinic $M_3$ receptor" include voiding dysfunction or urine storage dysfunction in underactive bladder, hypotonic bladder, acontractile bladder, detrusor underactivity, neurogenic bladder, urethra relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like, preferably, voiding dysfunction or urine storage dysfunction in underactivity bladder, hypotonic bladder, acontractile bladder, detrusor underactivity, and neurogenic bladder.

The "alkyl" is linear alkyl and branched alkyl. Accordingly, the "$C_{1-6}$ alkyl" is linear or branched alkyl having 1 to 6 carbon atoms, and specific examples thereof include methyl, ethyl, n-propyl, isopropyl, n-butyl, isobutyl, sec-butyl, tert-butyl, n-pentyl, or n-hexyl; in one embodiment, methyl, ethyl, n-propyl, isopropyl, n-butyl, isobutyl, sec-butyl, or tert-butyl, each of which is $C_{1-4}$ alkyl; in one embodiment, a group selected from the group consisting of methyl, ethyl, isopropyl, and isobutyl; and in one embodiment, a group selected from the group consisting of methyl and ethyl.

The "alkylene" is linear alkylene or branched alkylene. Accordingly, the "$C_{1-6}$ alkylene" is linear or branched alkylene having 1 to 6 carbon atoms, and examples thereof include methylene, ethylene, trimethylene, tetramethylene, pentamethylene, hexamethylene, propylene, methylmethylene, ethylethylene, 1,2-dimethylethylene, or 1,1,2,2-tetramethylethylene; in one embodiment, $C_{1-3}$ alkylene; in one embodiment, methylene or ethylene; in one embodiment, methylene; and in another embodiment, ethylene.

The "halogeno-$C_{1-6}$ alkyl" is $C_{1-6}$ alkyl substituted with at least one halogen atom; in one embodiment, $C_{1-6}$ alkyl substituted with 1 to 5 halogen atoms; in one embodiment, difluoromethyl or trifluoromethyl; and in one embodiment, trifluoromethyl.

The "cycloalkyl" is a saturated hydrocarbon cyclic group. Accordingly, the "$C_{3-8}$ cycloalkyl" is a saturated hydrocarbon cyclic group having 3 to 8 ring members, and specific examples thereof include cyclopropyl, cyclobutyl, cyclopentyl, cyclohexyl, cycloheptyl, or cyclooctyl; in one embodiment, cyclopropyl, cyclobutyl, cyclopentyl, or cyclohexyl, each of which is $C_{3-6}$ cycloalkyl; and in one embodiment, cyclopropyl.

The "aryl" is a $C_{6-14}$ monocyclic to tricyclic aromatic hydrocarbon cyclic group and includes a partially hydrogenated cyclic group thereof, and specific examples thereof include phenyl, naphthyl, tetrahydronaphthyl, indanyl, or indenyl; and in one embodiment, phenyl.

The "monocyclic aromatic hetero ring" is a monocyclic aromatic hetero ring group having 5 to 7 ring members, which has 1 to 4 hetero atoms selected from the group consisting of a nitrogen atom, an oxygen atom, and a sulfur atom as a ring-constituting atom, and specific examples thereof include pyrrolyl, pyrazolyl, imidazolyl, triazolyl, furyl, thienyl, oxazolyl, oxadiazolyl, thiazolyl, thiadiazolyl, pyridyl, pyridazinyl, pyrimidinyl, pyrazinyl, or azepanyl; in one embodiment, thienyl or pyridyl; and in one embodiment, thienyl.

The "bicyclic aromatic hetero ring" is a bicyclic aromatic hetero ring group in which the monocyclic aromatic hetero ring is fused with a benzene ring or monocyclic aromatic hetero ring and includes a partially hydrogenated ring group thereof, and specific examples thereof include indolyl, isoindolyl, indazolyl, benzotriazolyl, benzofuranyl, benzothienyl, benzooxazolyl, benzothiazolyl, quinolyl, isoquinolyl, cinnolinyl, quinazolinyl, quinoxalinyl, naphthyridinyl, furopyridyl, thienopyridyl, indolinyl, dihydrobenzofuranyl, dihydrobenzothienyl, dihydroquinolyl, tetrahydroquinolyl, dihydroisoquinolyl, tetrahydroisoquinolyl, dihydrofuropyridyl, or dihydrothienopyridyl; and in one embodiment, benzothienyl.

The "saturated hetero ring" is a 3- to 8-membered saturated ring group, which has 1 to 4 hetero atoms selected from the group consisting of a nitrogen atom, an oxygen atom, and a sulfur atom as a ring-constituting atom, and may be bridged with $C_{1-6}$ alkylene, in which a sulfur atom as the ring-constituting atom may be oxidized. Specific examples thereof include azepanyl, diazepanyl, oxazepanyl, thiazepanyl, aziridinyl, azetidinyl, pyrrolidinyl, imidazolidinyl, piperidinyl, pyrazolidinyl, piperazinyl, azocanyl, thiomorpholinyl, thiazolindinyl, isothiazolindinyl, oxazolindinyl, morpholinyl, thiomorpholinyl, tetrahydrothiopyranyl, oxathioranyl, oxiranyl, oxetanyl, dioxiranyl, tetrahydrofuranyl, tetrahydropyranyl, and 1,4-dioxanyl.

The "cyclic amino" is a 4- to 7-membered group having a bond at a ring-constituting nitrogen atom in the saturated hetero ring. Specific examples thereof include aziridin-1-yl, azetidin-1-yl, pyrrolidin-1-yl, piperidin-1-yl, azepan-1-yl, azocan-1-yl, morpholin-4-yl, thiomorpholin-4-yl, piperazin-1-yl, 1,4-diazepan-1-yl, 1,4-oxazepan-4-yl, or 1,4-thiazepan-4-yl; in one embodiment, pyrrolidin-1-yl, piperidin-1-yl, azetidin-1-yl, morpholin-4-yl, or piperazin-1-yl; and in one embodiment, pyrrolidin-1-yl or piperidin-1-yl.

The "halogen" means fluoro, chloro, bromo, or iodo; in one embodiment, fluoro, chloro, or bromo; in one embodiment, fluoro or chloro; in one embodiment, fluoro; and in another embodiment, chloro.

In the present specification, the expression "which may be substituted" means "which is not substituted" or "which is substituted with 1 to 5 substituents". Further, if it has a plurality of substituents, the substituents may be the same as or different from each other.

Examples of the acceptable substituent in the "cyclic amino which may be substituted", the "$C_{3-8}$ cycloalkyl which may be substituted", the "aryl which may be substituted", the "monocyclic aromatic hetero ring which may be substituted", and the "bicyclic aromatic hetero ring which may be substituted" include substituents in the following Group G.

Group G
(a) $C_{1-6}$ alkyl which may be substituted with at least one group selected from the group consisting of —OH, —O—($C_{1-6}$ alkyl), —CN, —SO$_2$—($C_{1-6}$ alkyl), and halogen,
(b) —OH,
(c) —O—($C_{1-6}$ alkyl which may be substituted with at least one group selected from the group consisting of —OH, —O—($C_{1-6}$ alkyl), —CN, —SO$_2$—($C_{1-6}$ alkyl), and halogen),
(d) $C_{3-8}$ cycloalkyl,
(e) —O—($C_{3-8}$ cycloalkyl),
(f) halogen,
(g) —CN,
(h) —SO$_2$—($C_{1-6}$ alkyl),
(i) —CO$_2$—($C_{1-6}$ alkyl) and —COOH,
(j) —CO—N($C_{1-6}$ alkyl)$_2$, —CO—NH($C_{1-6}$ alkyl), and —CONH$_2$,
(k) —CO—($C_{1-6}$ alkyl),
(l) —SO$_2$—N($C_{1-6}$ alkyl)$_2$, —SO$_2$—NH($C_{1-6}$ alkyl), and —SO$_2$NH$_2$,
(m) —N($C_{1-6}$ alkyl)$_2$, —NH($C_{1-6}$ alkyl), and —NH$_2$,
(n) a saturated hetero ring, and
(o) —O-saturated hetero ring.

Examples of the substituent in the "cyclic amino which may be substituted" further include oxo (=O).

In addition, the preferable substituents in the "$C_{1-6}$ alkyl which may be substituted" are the substituents described in (b) to (o) of Group G above.

Examples of the preferable substituents for the "cyclic amino which may be substituted" in $R^1$ include, in one embodiment, the substituents described in (a) to (c), (f), and (g) of Group G above; in one embodiment, $C_{1-6}$ alkyl which may be substituted with at least one group selected from the group consisting of —OH, —O—($C_{1-6}$ alkyl), —CN, —SO$_2$—($C_{1-6}$ alkyl), and halogen; in one embodiment, a group selected from the group consisting of $C_{1-6}$ alkyl and halogeno-$C_{1-6}$ alkyl; and in one embodiment, a group selected from the group consisting of methyl and ethyl.

Examples of the preferable substituents for the "$C_{1-6}$ alkyl which may be substituted" in $R^{12}$ include, in one embodiment, the substituents described in (b) to (g), and (n) of Group G above; in one embodiment, a group selected from the group consisting of $C_{3-8}$ cycloalkyl, —O—($C_{1-6}$ alkyl), —O—($C_{3-8}$ cycloalkyl), halogen, —CN, and cyclic amino; in one embodiment, a group selected from the group consisting of $C_{3-8}$ cycloalkyl and —O—($C_{1-6}$ alkyl); and in one embodiment, a group selected from the group consisting of cyclopropyl and methoxy.

Examples of the preferable substituents for the "$C_{3-8}$ cycloalkyl which may be substituted" in $R^{12}$ include, in one embodiment, the substituents described in (a) to (c), (f), and (g) of Group G above; and in one embodiment, $C_{1-6}$ alkyl which may be substituted with —O—($C_{1-6}$ alkyl).

Examples of the preferable substituents for the "aryl which may be substituted" in $R^2$ include, in one embodiment, the substituents described in (a) to (d), (f), (g), and (n) of Group G above; in one embodiment, a group selected from the group consisting of $C_{1-6}$ alkyl, halogeno-$C_{1-6}$ alkyl, —O—($C_{1-6}$ alkyl), —O-(halogeno-$C_{1-6}$ alkyl), halogen, $C_{3-8}$ cycloalkyl, and —CN; in one embodiment, a group selected from the group consisting of halogeno-$C_{1-6}$ alkyl and halogen; and in one embodiment, a group selected from the group consisting of trifluoromethyl and fluoro.

Examples of the preferable substituents for the "monocyclic aromatic hetero ring which may be substituted" and "bicyclic aromatic hetero ring which may be substituted" in $R^2$ include, in one embodiment, the substituents described in (a) to (d), (f), (g), and (n) of Group G above; in one embodiment, a group selected from the group consisting of $C_{1-6}$ alkyl, halogeno-$C_{1-6}$ alkyl, —O—($C_{1-6}$ alkyl), —O-(halogeno-$C_{1-6}$ alkyl), halogen, $C_{3-8}$ cycloalkyl, and —CN; in one embodiment, a group selected from the group consisting of $C_{1-6}$ alkyl, halogeno-$C_{1-6}$ alkyl, —O—($C_{1-6}$ alkyl), $C_{3-8}$ cycloalkyl, and halogen; in one embodiment, a group selected from the group consisting of halogeno-$C_{1-6}$ alkyl, —O—($C_{1-6}$ alkyl), and halogen; and in one embodiment, a group selected from the group consisting of trifluoromethyl, methoxy, and chloro.

One embodiment of the compound of the formula (I) or a salt thereof is shown below.

(1-1)
The compound of the formula (I) or a salt thereof, in which
$R^1$ is
i. cyclic amino which may be substituted with 1 to 5 substituents selected from the group consisting of Group G and oxo, or
ii. —N(—$R^{11}$)(—$R^{12}$),
$R^{11}$ is $C_{1-6}$ alkyl, and
$R^{12}$ is $C_{1-6}$ alkyl which may be substituted with 1 to 5 substituents selected from the substituents described in (b) to (o) of Group G, or $C_{3-8}$ cycloalkyl which may be substituted with 1 to 5 substituents selected from Group G.

(1-2)
The compound of the formula (I) or a salt thereof, in which
$R^1$ is
i. cyclic amino which may be substituted with 1 to 5 substituents selected from the group consisting of Group G and oxo, or
ii. —N(—$R^{11}$)(—$R^{12}$),
$R^{11}$ is $C_{1-6}$ alkyl, and
$R^{12}$ is $C_{1-6}$ alkyl which may be substituted with 1 to 3 substituents selected from the substituents described in (b) to (g), and (n) of Group G.

(1-3)
The compound of the formula (I) or a salt thereof, in which
$R^1$ is
i. pyrrolidin-1-yl or piperidin-1-yl, in which pyrrolidin-1-yl and piperidin-1-yl are each substituted with 1 to 2 substituents selected from the group consisting of $C_{1-6}$ alkyl and halogeno-$C_{1-6}$ alkyl, or
ii. —N(—$R^{11}$)(—$R^{12}$), in which
$R^{11}$ is $C_{1-6}$ alkyl, and
$R^{12}$ is $C_{1-6}$ alkyl which may be substituted with one group selected from the group consisting of $C_{3-8}$ cycloalkyl and —O—($C_{1-6}$ alkyl).

(1-4)
The compound of the formula (I) or a salt thereof, in which $R^1$ is cyclic amino substituted with 1 to 2 groups selected from the group consisting of $C_{1-6}$ alkyl and halogeno-$C_{1-6}$ alkyl.

(1-5)
The compound of the formula (I) or a salt thereof, in which $R^1$ is pyrrolidin-1-yl or piperidin-1-yl, in which pyrrolidin-1-yl and piperidin-1-yl may be substituted with 1 to 3 substituents selected from Group G.

(1-6)
The compound of the formula (I) or a salt thereof, in which $R^1$ is pyrrolidin-1-yl or piperidin-1-yl, in which pyrrolidin-1-yl and piperidin-1-yl are each substituted with 1 to 2 groups selected from the group consisting of $C_{1-6}$ alkyl and halogeno-$C_{1-6}$ alkyl.

(1-7)
The compound of the formula (I) or a salt thereof, in which $R^1$ is pyrrolidin-1-yl substituted with 1 to 2 groups selected from the group consisting of methyl and ethyl.

(1-8)
The compound of the formula (I) or a salt thereof, in which
$R^1$ is —N(—$R^{11}$)(—$R^{12}$),
$R^{11}$ is $C_{1-6}$ alkyl, and
$R^{12}$ is $C_{1-6}$ alkyl which may be substituted with a group selected from the group consisting of $C_{3-8}$ cycloalkyl and —O—($C_{1-6}$ alkyl).

(1-9)
The compound of the formula (I) or a salt thereof, in which
$R^1$ is —N(—$R^{11}$)(—$R^{12}$),
$R^{11}$ is methyl, ethyl, or isopropyl, and
$R^{12}$ is methyl, ethyl, isopropyl, isobutyl, cyclopropylmethyl, or methoxyethyl.

(2-1)
The compound of the formula (I) or a salt thereof, in which
$R^2$ is
i. aryl which may be substituted with 1 to 5 substituents selected from Group G,
ii. monocyclic aromatic hetero ring which may be substituted with 1 to 5 substituents selected from Group G, or
iii. bicyclic aromatic hetero ring which may be substituted with 1 to 5 substituents selected from Group G.

(2-2)
The compound of the formula (I) or a salt thereof, in which
$R^2$ is
i. phenyl which may be substituted with 1 to 5 substituents selected from Group G,
ii. thienyl which may be substituted with 1 to 3 substituents selected from Group G
iii. pyridyl which may be substituted with 1 to 3 substituents selected from Group G, or
iv. benzothienyl which may be substituted with 1 to 5 substituents selected from Group G.

(2-3)
The compound of the formula (I) or a salt thereof, in which
$R^2$ is
i. phenyl which may be substituted with 1 to 3 groups selected from the group consisting of $C_{1-6}$ alkyl, halogeno-$C_{1-6}$ alkyl, —O—($C_{1-6}$ alkyl), —O-(halogeno-$C_{1-6}$ alkyl), halogen, $C_{3-8}$ cycloalkyl, and —CN,
ii. thienyl which may each be substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen,
iii. pyridyl which may each be substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen, or
iv. benzothienyl.

(2-4)
The compound of the formula (I) or a salt thereof, in which
$R^2$ is
i. phenyl di-substituted with trifluoromethyl and fluoro,
ii. thienyl mono-substituted with trifluoromethyl or chloro, or
iii. pyridyl di-substituted with trifluoromethyl and methoxy.

(2-5)
The compound of the formula (I) or a salt thereof, in which $R^2$ is a monocyclic aromatic hetero ring which may be substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen.

(2-6)
The compound of the formula (I) or a salt thereof, in which
$R^2$ is
i. thienyl which may be substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen, or
ii. pyridyl which may be substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen.

(2-7)
The compound of the formula (I) or a salt thereof, in which $R^2$ is thienyl which may be substituted with 1 to 3 groups selected from the group consisting of $C_{1-6}$ alkyl, halogeno-$C_{1-6}$ alkyl, $C_{3-8}$ cycloalkyl, and halogen.

(2-8)
The compound of the formula (I) or a salt thereof, in which $R^2$ is thienyl which may be substituted with 1 or 2 substituents selected from the group consisting of halogeno-$C_{1-6}$ alkyl and halogen.

(2-9)
The compound of the formula (I) or a salt thereof, in which $R^2$ is thienyl which may be substituted with 1 or 2 substituents selected from the group consisting of trifluoromethyl and chloro.

(2-10)
The compound of the formula (I) or a salt thereof, in which $R^2$ is thienyl mono-substituted with trifluoromethyl or chloro.

(2-11)
The compound of the formula (I) or a salt thereof, in which $R^2$ is pyridyl which may be substituted with 1 to 3 groups selected from the group consisting of halogeno-$C_{1-6}$ alkyl and —O—($C_{1-6}$ alkyl).

(2-12)
The compound of the formula (I) or a salt thereof, in which $R^2$ is phenyl which may be substituted with 1 to 5 groups selected from the group consisting of $C_{1-6}$ alkyl, halogeno-$C_{1-6}$ alkyl, —O—($C_{1-6}$ alkyl), —O-(halogeno-$C_{1-6}$ alkyl), halogen, $C_{3-8}$ cycloalkyl, and —CN.

(2-13)
The compound of the formula (I) or a salt thereof, in which $R^2$ is phenyl which may be substituted with 1 or 2 substituents selected from the group consisting of halogeno-$C_{1-6}$ alkyl and halogen.

(2-14)
The compound of the formula (I) or a salt thereof, in which
$R^2$ is
i. thienyl which may be substituted with 1 or 2 substituents selected from the group consisting of halogeno-$C_{1-6}$ alkyl and halogen, or
ii. phenyl which may be substituted with 1 or 2 substituents selected from the group consisting of halogeno-$C_{1-6}$ alkyl and halogen.

(3-1)
The compound of the formula (I) or a salt thereof, in which $R^3$'s are the same as or different from each other, and are each $C_{1-6}$ alkyl.

(3-2)
The compound of the formula (I) or a salt thereof, in which $R^3$ is methyl.

(4-1)
The compound of the formula (I) or a salt thereof, in which W is $C_{1-6}$ alkylene.

(4-2)
The compound of the formula (I) or a salt thereof, in which W is $C_{1-3}$ alkylene.

(4-3)
The compound of the formula (I) or a salt thereof, in which W is methylene or ethylene.

(4-4)
The compound of the formula (I) or a salt thereof, in which W is methylene.

(4-5)
The compound of the formula (I) or a salt thereof, in which W is ethylene.

(5-1)
The compound of the formula (I) or a salt thereof, in which n is an integer of 0 to 4.

(5-2)
The compound of the formula (I) or a salt thereof, in which n is an integer of 0 to 2.

(5-3)
The compound of the formula (I) or a salt thereof, in which n is 0 or 1.

(6) The compound of the formula (I) or a salt thereof, which is a combination of any two or more of the groups, which are not inconsistent with each other, among some embodiments of each group described in (1-1) to (5-3) above. Examples thereof include the compounds or salts thereof shown below.

(6-1)
The compound of the formula (I) or a salt thereof, in which
$R^1$ is as described in (1-2) above,
$R^2$ is as described in (2-2) above,
$R^3$ is as described in (3-1) above,
W is as described in (4-1) above, and
n is as described in (5-1) above.

(6-2)
The compound or a salt thereof as described in (6-1) above, in which
$R^1$ is as described in (1-3) above,
$R^2$ is as described in (2-3) above,
W is as described in (4-2) above, and
n is as described in (5-3) above.

(6-3)
The compound or a salt thereof as described in (6-2) above, in which
$R^2$ is as described in (2-4) above, and
W is as described in (4-3) above.

(6-4)
The compound or a salt thereof as described in (6-2) above, in which
$R^1$ is as described in (1-6) above,
$R^2$ is as described in (2-14) above, and
W is as described in (4-3) above.

Examples of the specific compounds included in the present invention include the following compounds or salts thereof:
3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid, 3-[(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]propanoic acid,

[(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]acetic acid, 3-(4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}piperazin-1-yl)propanoic acid, 3-[(2R)-4-(5-{[4-(4-chlorothiophen-2-yl)-5-{[(2R)-2-ethylpyrrolidin-1-yl]methyl}-1,3-thiazol-2-yl]carbamoyl}pyrazin-2-yl)-2-methylpiperazin-1-yl]propanoic acid, 3-[(3R)-3-methyl-4-{5-[(5-{[(2R)-2-methylpyrrolidin-1-yl]methyl)}-4-[4-(trifluoromethyl)thiophen-2-yl]-1,3-thiazol-2-yl)carbamoyl]pyrazin-2-yl}piperazin-1-yl]propanoic acid, 3-(4-{5-[(5-{[(2R,5R)-2,5-dimethylpyrrolidin-1-yl]methyl}-4-[3-fluoro-5-(trifluoromethyl)phenyl]-1,3-thiazol-2-yl)carbamoyl]pyrazin-2-yl}piperazin-1-yl)propanoic acid, and 3-{(2R)-4-[5-({5-[(diethylamino)methyl]-4-[3-fluoro-5-(trifluoromethyl)phenyl]-1,3-thiazol-2-yl}carbamoyl)pyrazin-2-yl]-2-methylpiperazin-1-yl}propanoic acid.

In another embodiment, examples of the specific compounds included in the present invention include the following compounds or salts thereof:

3-[(3S)-4-(5-{[4-(4-chlorothiophen-2-yl)-5-{[(2R)-2-ethylpyrrolidin-1-yl]methyl}-1,3-thiazol-2-yl]carbamoyl}pyrazin-2-yl)-3-methylpiperazin-1-yl]propanoic acid, 3-(4-{5-[(4-[6-methoxy-5-(trifluoromethyl)pyridin-3-yl]-5-{[(2R)-2-methylpyrrolidin-1-yl]methyl}-1,3-thiazol-2-yl)carbamoyl]pyrazin-2-yl}piperazin-1-yl)propanoic acid, 3-[4-(5-{[4-(4-chlorothiophen-2-yl)-5-{[(2R)-2-methylpyrrolidin-1-yl]methyl}-1,3-thiazol-2-yl]carbamoyl}pyrazin-2-yl)piperazin-1-yl]propanoic acid,

[(3R)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-3-methylpiperazin-1-yl]acetic acid, 3-[4-(5-{[4-(4-chlorothiophen-2-yl)-5-{[(2R)-2-ethylpyrrolidin-1-yl]methyl}-1,3-thiazol-2-yl]carbamoyl}pyrazin-2-yl)piperazin-1-yl]propanoic acid, 3-(4-{5-[(4-[3-fluoro-5-(trifluoromethyl)phenyl]-5-{[isobutyl(methyl)amino]methyl}-1,3-thiazol-2-yl)carbamoyl]pyrazin-2-yl}piperazin-1-yl)propanoic acid, 3-[(2R)-4-(5-{[4-(4-chlorothiophen-2-yl)-5-{[(cyclopropylmethyl)(methyl)amino]methyl}-1,3-thiazol-2-yl]carbamoyl}pyrazin-2-yl)-2-methylpiperazin-1-yl]propanoic acid, 3-(4-{5-[(5-{[(2R,5R)-2,5-dimethylpyrrolidin-1-yl]methyl}-4-[4-(trifluoromethyl)-thiophen-2-yl]-1,3-thiazol-2-yl)carbamoyl]pyrazin-2-yl}piperazin-1-yl)propanoic acid, {(3R)-4-[5-({5-[(diethylamino)methyl]-4-[3-fluoro-5-(trifluoromethyl)phenyl]-1,3-thiazol-2-yl}carbamoyl)pyrazin-2-yl]-3-methylpiperazin-1-yl}acetic acid, and (4-{5-[(5-{[(2R,5R)-2,5-dimethylpyrrolidin-1-yl]methyl}-4-[3-fluoro-5-(trifluoromethyl)phenyl]-1,3-thiazol-2-yl)carbamoyl]pyrazin-2-yl}piperazin-1-yl)acetic acid.

With regard to the compound of the formula (I), tautomers or geometrical isomers thereof may exist, depending on the kinds of the substituents. In the present specification, the compound of the formula (I) may be described in only one form of isomers in some cases, but the present invention includes other isomers, isolated forms of the isomers, or a mixture thereof.

Furthermore, some of the compounds of the formula (I) may have asymmetric carbon atoms or asymmetries in some cases, and correspondingly, the optical isomers thereof can exist. The present invention includes the isolated form of the optical isomer of the compound of the formula (I) or a mixture thereof.

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198.

Moreover, the salt of the compound of the formula (I) is a pharmaceutically acceptable salt of the compound of the formula (I), and the compounds of the formula (I) may form an acid addition salt or a salt with a base, depending on the kinds of the substituents in some cases. Specifically, examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propanoic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, and glutamic acid, and salts with metal anions such as sodium, potassium, magnesium, calcium, and aluminum, and with organic bases such as methylamine, ethylamine, and ethanolamine, salts with various amino acids such as acetyl leucine, lysine, and ornithine, or derivatives of amino acids, ammonium salts, and others.

In addition, the present invention also includes various hydrates or solvates, and crystal polymorph substances of the compound of the formula (I) and a salt thereof. In addition, the present invention also includes the compounds labeled with various radioactive or non-radioactive isotopes.

(Production Process)

The compound of the formula (I) or a salt thereof can be prepared by applying various known synthetic methods, using the characteristics based on their basic structures or the kinds of the substituents. At this time, depending on the types of the functional groups, it is in some cases effective from the viewpoint of the preparation techniques to protect the functional group with an appropriate protective group (a group which is capable of being easily converted into the functional group), during the steps from starting materials to intermediates. Examples of the protective group include the protective groups as described in "Greene's Protective Groups in Organic Synthesis (4th edition, 2006)", edited by P. G. M. Wuts and T. W. Greene, and the like, which may be appropriately selected and used depending on the reaction conditions. In these methods, a desired compound can be obtained by introducing the protective group to carry out the reaction, and then, if desired, removing the protective group.

In addition, the prodrug of the compound of the formula (I) can be prepared by introducing a specific group during the steps from starting materials to intermediates, in the same manner as for the above protective groups, or by further carrying out the reaction using the obtained compound of the formula (I). The reaction can be carried out by applying a method known to a person skilled in the art, such as common esterification, amidation, and dehydration.

Hereinbelow, typical preparation methods of the compound of the formula (I) and the compound of the formula (a) which is the starting compound will be described. Each of the production processes can also be carried out with reference to the documents appended to the description herein. Further, the preparation methods of the present invention are not limited to the examples as shown below.

(Production Process 1)

[Chem. 6]

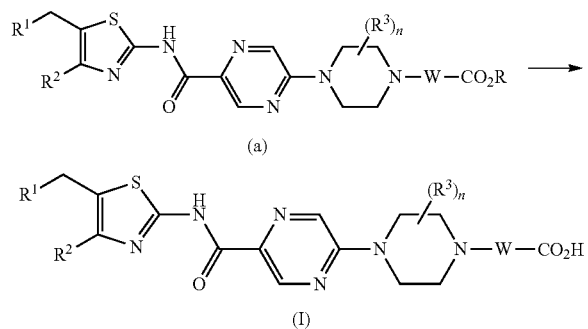

(in which, R represents $C_{1-6}$ alkyl, which shall apply hereinafter).

This reaction is a method for producing a compound of the formula (I) which is a compound of the present invention, by deprotecting a compound of the formula (a).

This reaction is carried out using the compound of the formula (a) and a deprotecting reagent in equivalent amounts, or either thereof in an excess amount, by stirring the mixture under the temperature condition ranging from under cooling to heating to reflux, usually for 0.1 hours to 5 days, in a solvent which is inert to the reaction or without a solvent. Examples of the solvent used herein are not particularly limited, but include alcohols such as methanol, ethanol, n-propanol and the like, N,N-dimethylformamide, tetrahydrofuran, and the like. Further, there are some cases where a mixed solvent of the solvent and water is highly suitable for the reaction. Examples of the deprotecting reagent are not particularly limited, but include bases such as an aqueous sodium hydroxide solution, an aqueous potassium hydroxide solution and the like, and acids such as hydrochloric acid, trifluoroacetic acid and the like.

(Production Process 2)

[Chem. 7]

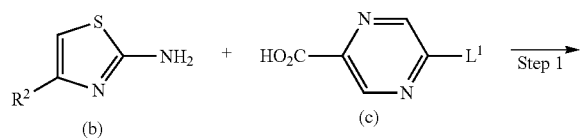

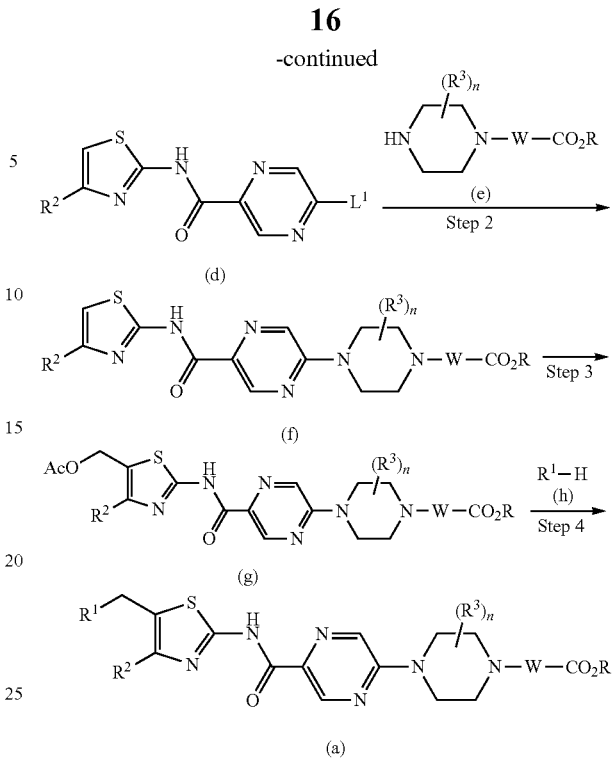

(in which, $L^1$ represents a leaving group, which shall apply hereinafter).

This production process is a method for producing the compound of the formula (a) which is a starting material of the compound of the formula (I). Here, examples of $L^1$ include chloro and the like.

(Step 1)

This step is a step of preparing a compound of the formula (d) by subjecting a compound of the formula (b) and a compound of the formula (c) to an amidation reaction.

The reaction is carried out using the formula (b) and the compound of the formula (c) in equivalent amounts, or either thereof in an excess amount, by stirring the mixture under the temperature condition ranging from under cooling to under heating, preferably at −20° C. to 60° C., usually for 0.1 hours to 5 days, in a solvent which is inert to the reaction, in the presence of a condensing agent. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran, dioxane, 1,2-dimethoxyethane, cyclopentylmethyl ether and the like, N,N-dimethylformamide, dimethylsulfoxide, ethyl acetate, acetonitrile, water, and a mixture thereof. Examples of the condensing reagent include 1-(3-dimethylamino propyl)-3-ethylcarbodiimide or a hydrochloride thereof, dicyclohexylcarbodiimide, 1,1'-carbonyldiimidazole, diphenylphosphoric azide, phosphorous oxychloride, N-[({[(1Z)-1-cyano-2-ethoxy-2-oxoethylidene]amino}oxy)morpholin-4-yl)methylene]-N-methylmethanaminium hexafluorophosphate (COMU), and the like, but are not limited thereto. It may be preferable in some cases for the reaction to use an additive (for example, 1-hydroxybenzotriazole), and it may be advantageous in some cases for the smooth progress of the reaction to carry out the reaction in the presence of an organic base such as triethylamine, N,N-diisopropylethylamine, N-methylmorpholine and the like, or an inorganic base such as potassium carbonate, sodium carbonate, potassium hydroxide and the like.

Furthermore, a method in which the carboxylic acid (c) is converted to a reactive derivative thereof, and then the reactive derivative is reacted with the amine (b) can also be used. Examples of the reactive derivative of the carboxylic acid include acid halides obtained by the reaction with a halogenating agent such as phosphorus oxychloride, thionyl chloride or the like, mixed acid anhydrides obtained by the reaction with isobutyl chloroformate or the like, and active esters obtained by condensation with 1-hydroxybenzotriazole or the like. The reaction of these reactive derivatives and the compound (b) can be carried out under the temperature condition ranging from under cooling to under heating, preferably at −20° C. to 60° C., in a solvent which is inert to the reaction, such as halogenated hydrocarbons, aromatic hydrocarbons, ethers and the like.

References

"Organic Functional Group Preparations" written by S. R. Sandler and W. Karo, $2^{nd}$ edition, Vol. 1, Academic Press Inc., 1991

"Courses in Experimental Chemistry ($5^{th}$ edition)" edited by The Chemical Society of Japan, Vol. 16 (2005) (Maruzen).

(Step 2)

This step is a step of preparing a compound of the formula (f) by reacting a compound of the formula (d) with a compound of the formula (e).

This reaction is carried out using the formula (d) and the compound of the formula (e) in equivalent amounts, or either thereof in an excess amount, by stirring the mixture under the temperature condition ranging from under cooling to under heating to reflux, preferably at 0° C. to 80° C., usually for 0.1 hours to 5 days, in a solvent which is inert to the reaction or without a solvent. Examples of the solvent used herein are not particularly limited, but include aromatic hydrocarbons such as benzene, toluene, xylene and the like, ethers such as diethyl ether, tetrahydrofuran, dioxane, 1,2-dimethoxyethane and the like, halogenated hydrocarbons such as dichloromethane, 1,2-dichloroethane, chloroform and the like, N,N-dimethylformamide, N-methylpyrrolidone, dimethylsulfoxide, ethyl acetate, acetonitrile, and a mixture thereof. It may be advantageous in some cases for the smooth progress of the reaction to carry out the reaction in the presence of an organic base such as triethylamine, N,N-diisopropylethylamine, N-methylmorpholine and the like, or an inorganic base such as potassium carbonate, sodium carbonate, potassium hydroxide and the like.

References

"Organic Functional Group Preparations" written by S. R. Sandler and W. Karo, $2^{nd}$ edition, Vol. 1, Academic Press Inc., 1991

"Courses in Experimental Chemistry ($5^{th}$ edition)" edited by The Chemical Society of Japan, Vol. 14 (2005) (Maruzen).

(Step 3)

This step is a step of preparing a compound of the formula (g) by introducing an acetoxymethyl group into the 5-position of thiazole in the compound of the formula (f). The compound of the formula (f) is reacted with an aqueous formaldehyde solution or paraformaldehyde in the presence of an acetic acid solvent, which can be carried out under the temperature condition ranging from at room temperature to under heating to reflux. Further, the reaction can also be carried out by adding acetic acid into a solvent which is inert to the reaction, such as halogenated hydrocarbons, aromatic hydrocarbons, ethers and the like, instead of the acetic acid solvent. In addition, the reaction can also be carried out by further adding acetic anhydride.

(Step 4)

This step is a step of preparing a compound of the formula (a) by reacting a compound of the formula (g) with a compound of the formula (h) under a basic condition. The present reaction can be carried out by reacting the compound of the formula (g) with the compound of the formula (h) in the presence of an organic base such as triethylamine and N,N-diisopropylethylamine, in an organic solvent which is inert to the reaction, such as halogenated hydrocarbons, aromatic hydrocarbons, ethers, esters, acetonitrile, N,N-dimethylformamide, dimethylsulfoxide, N-methylpyrrolidone and the like. Further, the compound of the formula (h) may also used in an excess amount instead of the organic base. The reaction can be carried out under the temperature condition ranging from under cooling to at room temperature; from at room temperature to under heating; or from at room temperature to under refluxing.

In addition, the compound of the formula (a) can be directly obtained while not isolating the compound of the formula (g) by adding the compound of the formula (h) into the reaction mixture of Step 3.

(Production Process 3)

[Chem. 8]

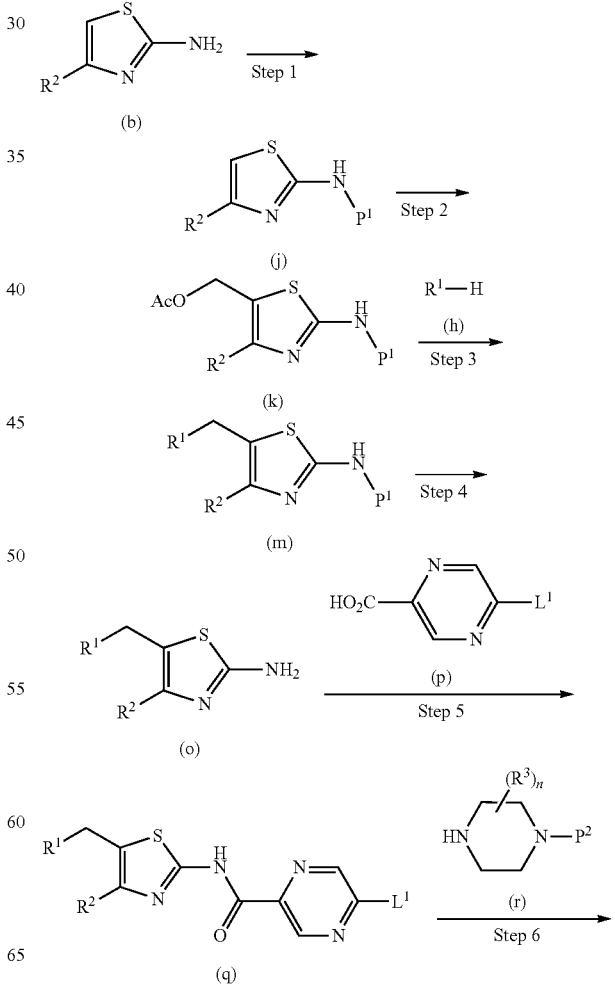

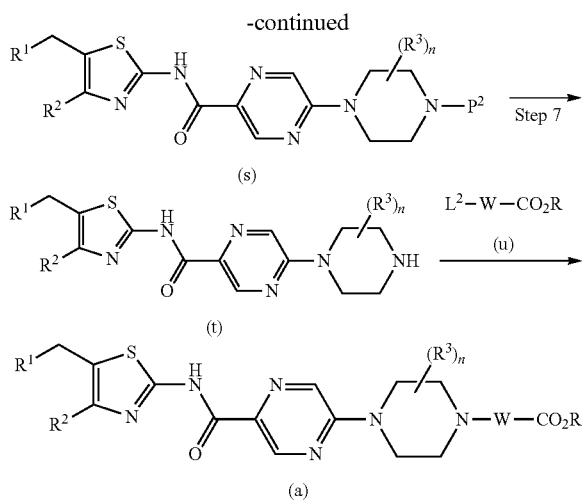

(in which, P¹ and P² each represent a protective group, and L² represents a leaving group).

This production process is another preparation method for the compound of the formula (a), which is a starting material of the compound of the formula (I). Here, as the protective groups represented by P¹ and P², the groups of amino groups described in "Protective Groups in Organic Synthesis" written by Wuts and Greene, 4th edition, John Wiley & Sons Inc., 2006, and the like can be used. Examples of the P¹ include acetyl, trifluoroacetyl and the like, examples of P² include t-butoxycarbonyl and the like, and examples of L² include bromo and the like.

(Step 1)

This step is a step of protecting the amino group of the compound (b). Here, the present reaction can be carried out with reference to "Protective Groups in Organic Synthesis" written by Wuts and Greene, 4th edition, John Wiley & Sons Inc., 2006.

(Step 2)

This step is a step of preparing a compound of the formula (k) by introducing an acetoxymethyl group into the 5-position of thiazole in a compound of the formula (j). The reaction conditions are the same as in Step 3 of Production Process 2.

(Step 3)

This step is a step of preparing a compound of the formula (m) by reacting a compound of the formula (h) and a compound of the formula (k) under a basic condition. The reaction conditions are the same as in Step 4 of Production Process 2.

(Step 4)

This step is a step of deprotecting a protective group P¹ of an amino group of the compound (m). Here, the present reaction can be carried out with reference to "Protective Groups in Organic Synthesis" written by Wuts and Greene, 4th edition, John Wiley & Sons Inc., 2006.

(Step 5)

This step is a step of obtaining a compound of the formula (q) by subjecting a compound of the formula (o) and a compound of the formula (p) to an amidation reaction. The reaction conditions are the same as in Step 1 of Production Process 2.

(Step 6)

This step is a step of preparing a compound of the formula (s) by reacting a compound of the formula (q) with a compound of the formula (r). The reaction conditions are the same as in Step 2 of Production Process 2.

(Step 7)

This step is a step of deprotecting a protective group P² of a compound of the formula (s).

This step can be carried out with reference to "Protective Groups in Organic Synthesis" written by Wuts and Greene, 4th edition, John Wiley & Sons Inc., 2006".

(Step 8)

This step is a step of obtaining the compound of the formula (a) by reacting a compound of the formula (t) and a compound of the formula (u). The present reaction is carried out using the compound (t) and the compound (u) in equivalent amounts, or either thereof in an excess amount, and stirring the mixture under the temperature condition ranging from under cooling to under heating to reflux, preferably at 0° C. to 100° C., usually for 0.1 hours to 5 days, in a solvent which is inert to the reaction, or without a solvent. Examples of the solvent used herein are not particularly limited, but include aromatic hydrocarbons such as benzene, toluene, xylene and the like, ethers such as diethyl ether, tetrahydrofuran, dioxane, 1,2-dimethoxyethane and the like, halogenated hydrocarbons such as dichloromethane, 1,2-dichloroethane, chloroform and the like, N,N-dimethylformamide, dimethylsulfoxide, N-methylpyrrolidone, ethyl acetate, acetonitrile, and a mixture thereof. It may be advantageous in some cases for the smooth progress of the reaction to carry out the reaction in the presence of an organic base such as triethylamine, N,N-diisopropylethylamine, N-methylmorpholine and the like, or an inorganic base such as potassium carbonate, sodium carbonate, potassium hydroxide and the like.

References

"Organic Functional Group Preparations" written by S. R. Sandler and W. Karo, 2nd edition, Vol. 1, Academic Press Inc., 1991

"Courses in Experimental Chemistry (5th edition)" edited by The Chemical Society of Japan, Vol. 14 (2005) (Maruzen).

The compound of the formula (I) is isolated and purified as its free compound, or a salt, a hydrate, a solvate, or crystal polymorph substance thereof. The salt of the compound of the formula (I) can also be prepared by a conventional method.

Isolation and purification are carried out by employing general chemical operations such as extraction, fractional crystallization, and various types of fractional chromatography.

Various isomers can be prepared by selecting appropriate starting compound, or separated by separation using differences in the physicochemical properties among the isomers. For example, the optical isomers can be obtained by means of general optical resolution methods of racemic compounds (for example, fractional crystallization introducing the compound into a diastereomer salt with an optically active base or acid; chromatography using a chiral column or the like; and others), or can also be prepared from appropriate optically active starting compound.

The pharmacological activity of the compound of the formula (I) was confirmed by the following test.

Test Example 1: Evaluation of Muscarinic $M_3$ Receptor Positive Allosteric Modulator Activity a) Construction of Vector Expressing Human Muscarinic $M_3$ Receptor A human muscarinic $M_3$ receptor gene (GenBank Accession No.: NM_000740.2) was introduced into an expression vector pcDNA3.1™ (Life Technologies).

b) Construction of Cells Stably Expressing Human Muscarinic $M_3$ Receptor

A vector expressing a human muscarinic $M_3$ receptor was introduced into a CHO—K1 cell (ATCC No.: CCL-61). The introduction was carried out according to the attached instructions, using a transfection reagent, Lipofectoamine (registered trademark) 2000 Reagent (Life Technologies). The cells were incubated in an alpha Modified Eagle Minimum Essential Medium (α-MEM) including 2 mM glutamine, 10% fetal bovine serum, and 2.0 mg/mL Geneticin (registered trademark) (Life Technologies) for 4 weeks to acquire a drug-resistant clone.

c) Measurement of Intracellular $Ca^{2+}$ Concentration

The cells obtained in b) above were suspended in an α-MEM including 2 mM glutamine, 10% fetal bovine serum, and 0.2 mg/mL Geneticin (registered trademark) to the amount from 1.2 to $1.5\times10^4$ cells/well the day before the experiment, dispensed into a 384-well plate (Model No. 355962, BD Biosciences), and incubated overnight at 37° C. and 5% $CO_2$. The medium was replaced with a loading buffer (an assay buffer (Hank's balanced salt solution (HBSS), 1 g/L BSA, 20 mM HEPES (pH 7.5), and 2.5 mM probenecid), including 3.1 μM Fluo 4-AM (Dojindo Laboratories) and incubated for about 2 hours at room temperature. Thereafter, the cells were washed with a plate washer ELx405™ (BIO-TEK Instrument, Inc.) set with the assay buffer, and set in an intracellular $Ca^{2+}$ concentration measuring system (FLIPR$^{tetra}$ (registered trademark), Molecular Device Co.). The test substances (final concentration of 1 μM or 10 μM) and carbachol (Sigma, final concentration of 0.0024 nM to 10 μM) which had each been dissolved in the assay buffer in advance were set in a FLIPR$^{tetra}$ (registered trademark). The test substances were added to the cells in the device and after about 5 minutes, carbachol was added to the cells. An increase rate of the intracellular $Ca^{2+}$ concentration by carbachol was measured (excitement wavelength of 470 nm to 495 nm and a fluorescence wavelength of 515 nm to 575 nm).

For the muscarinic $M_3$ receptor-positive allosteric modulator activity, a shift toward a lower concentration side of a carbachol concentration-response curve by the test substance was used as an index. That is, a minimum value in the carbachol response was taken as 0%; a maximum value in the carbachol response was taken as 100% from the concentration-response curve of carbachol; the carbachol concentration exhibiting a 50% response was calculated as an $EC_{50}$ value, using a Sigmoid-Emax model non-linear regression method, and thus, the muscarinic $M_3$ receptor-positive allosteric modulator activity was determined by dividing the $EC_{50}$ value of carbachol in the absence of the test substance by the $EC_{50}$ value of carbachol in the presence of the test substance. For example, when the $EC_{50}$ value of carbachol in the absence of the test substance was 0.1 μM and the $EC_{50}$ value of carbachol in the presence of the test substance was 0.01 μM, the value of the muscarinic $M_3$ receptor-positive allosteric modulator activity becomes 10, showing that the test substance causes a 10-fold shift in the $EC_{50}$ value toward to the low concentration side. In Tables below, the columns of 10 μM (-fold shift) show the values in a case where the test substance is added to a final concentration of 10 μM and the columns of 1 μM (-fold shift) show the values in a case where the test substance is added to a final concentration of 1 μM.

Test Example 2: Evaluation of Human c-Mpl-Introduced Ba/F3 Cell Proliferative Activity The human c-Mpl-introduced Ba/F3 cell proliferation action was measured by the following method.

As a positive control, 1-(5-{[4-(4-chlorothiophen-2-yl)-5-{[(2R)-2-methylpyrrolidin-1-yl]methyl}-1,3-thiazol-2-yl]carbamoyl}-3-fluoropyridin-2-yl)piperidine-4-carboxylic acid hydrochloride disclosed as Example 315 in Patent Document 1, represented by the formula (A1) above, was used. Further, it is known that the compound has a good human c-Mpl-introduced Ba/F3 cell proliferative activity as disclosed in Table 1 in Patent Document 1.

a) Construction of Vector Expressing Human c-Mpl Receptor

A human c-Mpl receptor gene (GenBank Accession No.: M90102.1) was transfected into an expression vector pEF-BOS (Nucleic Acids Research, 18: pp 5322 (1990)).

b) Construction of Cell Stably Expressing Human c-Mpl Receptor

A vector expressing a human c-Mpl receptor was introduced into a Ba/F3 cell (RIKEN BRC: RCB0805). For the introduction, an electroporation method was used. pEF-BOS-c-mpl (10 μg), pSV2bsr (1 μg, Kaken Pharmaceutical Co., Ltd.) and $1\times10^7$ of Ba/F3 cells were put into cuvettes with a gap width of 0.4 cm and electroporated under a condition of 1.5 kV (25 μF) in a Gene Pulser (registered trademark) (BioRad). The cells were incubated in an RPMI-1640 medium supplemented with a 0.5% WEHI conditioned medium (BD Biosciences) and 10% fetal bovine serum for 3 days, and thereafter, and the cells were incubated for 30 days in an RPMI-1640 medium, to which 10 μg/mL blasticidin had been further added, thereby acquiring a drug-resistant clone.

c) Measurement of Cell Proliferative Activity

The cells obtained in b) above were dispensed into an RPMI-1640 medium supplemented with a 0.5% WEHI conditioned medium and 10% fetal bovine serum, and used. The day before the experiment, the test substances (final concentration of 100 nM to 10 μM) which had been dissolved in a medium for assay (an RPMI-1640 medium supplemented with 10% fetal bovine serum) were added to a 384-well plate (Model No. 781185, Greiner bio-one). The cells after the medium had been replaced with the medium for assay were dispensed to a 384-well plate to which the test substance had been added, to $1\times10^4$ cells/well, and incubated overnight at 37° C. and 5% $CO_2$. On the experiment day, a solution of a Cell counting kit (Dojindo Laboratories) was added to each well of the 384-well plate, and the cells were incubated for about 5 hours at 37° C. and 5% $CO_2$. Thereafter, the absorbance (an absorbance wavelength of 450 nm) of each well was measured using Safire$^2$ (registered trademark) (TECAN), and used as an index for the number of cells. Further, as a negative control, a well to which the test substances had not been added was prepared.

By taking the absorbance of the well to which the test substance had been not added as 0% and taking the absorbance in a case where the positive control had been added to a final concentration of 1 μM as 100%, a cell proliferation rate (%) was calculated from the absorbance of the well to which the test substance had been added. From the obtained results, the test substance concentration exhibiting 30% proliferation by a Sigmoid-Emax model non-linear regression method was calculated as an $EC_{30}$ value.

Combinations of the muscarinic $M_3$ receptor-positive allosteric modulator activity (-fold shift) and the human c-Mpl-introduced Ba/F3 cell proliferative activity ($EC_{30}$ value, nM) of some Example compounds of the present invention are shown in Tables 1 and 2. However, Ex represents Example Compound Nos. as described later (this shall apply hereinafter).

TABLE 1

|    | Test Example 1 | | Test Example 2 |
|----|---|---|---|
| Ex | 10 μM (-fold shift) | 1 μM (-fold shift) | $EC_{30}$ (nM) |
| 3  | 253 | 101 | 780 |
| 4  | 200 | 25  | >3000 |
| 10 | 87  | 21  | >10000 |
| 11 | 226 | 33  | >10000 |
| 12 | 178 | 33  | >10000 |
| 13 | 326 | 43  | >10000 |
| 15 | 159 | 31  | >10000 |
| 17 | 109 | 15  | >10000 |
| 21 | 149 | 25  | >10000 |
| 27 | 330 | 31  | >10000 |
| 28 | 108 | 36  | 5300 |
| 33 | 182 | 40  | >10000 |
| 34 | 116 | 18  | >10000 |
| 41 | 160 | 43  | >10000 |
| 42 | 141 | 39  | >10000 |
| 43 | 224 | 76  | >10000 |
| 46 | 199 | 29  | >10000 |
| 48 | 113 | 27  | >10000 |
| 49 | 224 | 67  | >10000 |
| 50 | 190 | 108 | 2300 |
| 51 | 287 | 102 | 2600 |
| 52 | 196 | 36  | >10000 |
| 54 | 134 | 36  | >10000 |
| 60 | 235 | 33  | 9700 |
| 61 | 229 | 35  | 1300 |
| 62 | 195 | 37  | >10000 |
| 63 | 186 | 39  | >10000 |
| 64 | 128 | 23  | >10000 |
| 65 | 90  | 24  | >10000 |
| 67 | 114 | 40  | >10000 |
| 69 | 177 | 27  | >10000 |

TABLE 2

|    | Test Example 1 | | Test Example 2 |
|----|---|---|---|
| Ex | 10 μM (-fold shift) | 1 μM (-fold shift) | $EC_{30}$ (nM) |
| 71 | 151 | 28 | >10000 |
| 72 | 152 | 31 | >10000 |
| 79 | 171 | 60 | 1800 |
| 81 | 94  | 89 | 500 |
| 82 | 43  | 11 | >10000 |
| 91 | 139 | 19 | >10000 |
| 92 | 203 | 30 | >10000 |
| 95 | 233 | 91 | 3000 |
| 97 | 121 | 55 | 2800 |
| 100 | 229 | 82 | 3200 |
| 101 | 112 | 64 | 2700 |
| 103 | 307 | 202 | 1700 |
| 104 | 195 | 75 | >10000 |
| 106 | 270 | 41 | >10000 |
| 107 | 318 | 73 | >10000 |
| 108 | 169 | 56 | >10000 |
| 109 | 191 | 30 | >10000 |
| 111 | 627 | 203 | 5000 |
| 118 | 167 | 57 | >10000 |
| 119 | 503 | 110 | >10000 |
| 124 | 101 | 28 | >10000 |

TABLE 2-continued

|    | Test Example 1 | | Test Example 2 |
|----|---|---|---|
| Ex | 10 μM (-fold shift) | 1 μM (-fold shift) | $EC_{30}$ (nM) |
| 126 | 318 | 79 | >10000 |
| 128 | 192 | 73 | 8000 |
| 129 | 148 | 67 | >10000 |
| 130 | 151 | 95 | >10000 |
| 132 | 41  | 15 | >10000 |
| 133 | 164 | 30 | >10000 |
| 135 | 204 | 25 | >10000 |
| 140 | 158 | 28 | >10000 |
| 141 | 159 | 45 | >10000 |
| 142 | 160 | 52 | 4700 |
| 143 | 81  | 65 | 7800 |

In Test Example 1, a substantial number of the Example compounds which had been subjected to the present test shifted the $EC_{50}$ values to almost 100-fold or more toward a lower concentration side when added at 10 μM, and shifted the $EC_{50}$ values to almost 10-fold or more toward a lower concentration side when added at 1 μM. In addition, for some Example compounds of the present invention, from the viewpoint that the compounds alone do not change the intracellular $Ca^{2+}$ concentration, it was found that these compounds have no muscarinic $M_3$ receptor agonistic activity.

Furthermore, in Test Example 2, it was found that a substantial number of the Example compounds which had been subjected to the present test have a weak human c-Mpl-introduced Ba/F3 cell proliferative activity or have none.

The compound of the present invention is used as an agent for preventing or treating bladder/urinary tract diseases associated with bladder contractions via a muscarinic $M_3$ receptor, as a muscarinic $M_3$ receptor-positive allosteric modulator, and thus preferably has a weak or none increased platelet action based on c-Mpl-introduced Ba/F3 cell proliferative activity.

On the other hand, Table 1 of Patent Document 1 above discloses that the compound of Example 315 represented by the formula (A1) above has 3.2 nM of $EC_{30}$ value of c-Mpl-introduced Ba/F3 cell proliferation action.

Test Example 3: Effect on Electrical Field Stimulation-Induced Contraction in Rat Isolated Bladder As an effect on the nerve stimulation-dependent bladder contraction in in vitro, the effect of the Example compounds of the present invention in the electrical field stimulation-induced contraction of the rat isolated bladder was measured by the following method. That is, a bladder specimen having a width of about 2 mm and a length of about 10 mm in the longitudinal direction from the bladder isolated from a Sprague-Dawley (SD) female rat (Japan SLC, Inc.) was prepared. The prepared bladder specimen was suspended in an organ bath filled with 10 mL of a Krebs-Henseleite solution. The Krebs-Henseleite solution was aerated at 95% $O_2$ and 5% $CO_2$, and kept at 37° C. After carrying out stabilization at an initial tension of 1 g, the contraction was caused twice with 60 mM KCl. After stabilization of the specimen with a Krebs-Henseleite solution, the contraction was caused by carrying out electrical field stimulation at 20 V with an electrical stimulation device (Nihon Kohden) (a stimulation frequency of 8 Hz, a pulse width of 0.3 msec, and a stimulation time of 10 seconds). By repeating the transmural electrical stimulation at an interval of 2 minutes, a voltage was adjusted to obtain a contraction height of approximately 50% of the contractile response at 20 V. After the contraction by electrical field stimulation had been stabilized, 10 μL of the test substances dissolved in 100% dimethyl sulfoxide in advance (final concentrations of 3 μM, 10 μM, and 30 μM) was added thereto. The test substances were cumulatively administered at the following concentrations after the low-concentration contractile response had been stabilized. The response was taken into a personal computer through a PowerLab (registered trademark) (AD Instruments, Inc.), and analyzed by LabChart (registered trademark) (AD Instruments, Inc.). When the area under the response (area under curve, AUC) in each contraction response was calculated and the value before treatment with the test substance was taken as 100%, the enhancement rate (% of pre) of the isolated bladder contractions after treatment with the test substance was calculated.

The enhancement rates of the isolated bladder contractions by 10 μM of some Example compounds are shown in Table 3.

Furthermore, it was confirmed that all the Example compounds which have been subjected to the present test do not cause contraction in a state in which there is no electrical stimulation and the compounds alone do not show a bladder contraction action.

TABLE 3

| Ex. | Enhancement rate (% of pre) of isolated bladder contractions |
|---|---|
| 3 | 152 |
| 10 | 161 |
| 11 | 123 |
| 13 | 126 |
| 15 | 124 |
| 21 | 141 |
| 28 | 123 |
| 34 | 137 |
| 42 | 158 |
| 43 | 179 |
| 46 | 132 |
| 48 | 143 |
| 49 | 153 |
| 50 | 183 |
| 51 | 151 |
| 52 | 132 |
| 60 | 144 |
| 61 | 176 |
| 64 | 162 |
| 65 | 127 |
| 67 | 116 |
| 72 | 157 |
| 82 | 158 |
| 95 | 150 |
| 109 | 183 |
| 119 | 154 |
| 124 | 132 |
| 133 | 151 |
| 135 | 139 |
| 140 | 161 |
| 141 | 121 |
| 142 | 196 |
| 143 | 140 |

From the above, it was confirmed that the Example compounds alone, which have been subjected to the present test, do not cause a contraction action in the isolated rat bladder, but have an action of enhancing electrical field stimulation-induced contraction.

Test Example 4: Effect on Pelvic Nerve Stimulation-Induced Elevation of Intravesical Pressure in Anesthetized Rats The effect of the Example compounds of the present invention in the pelvic nerve electrical stimulation-induced elevation of intravesical pressure using rats as an action of nerve stimulation-dependent bladder contraction in vivo was measured by the following method. That is, SD female rats (Japan SLC, Inc.) were used and its lower abdomen was dissected at the midline under pentobarbital anesthesia (50 mg/kg ip). After ligating and cutting the ureter on both sides, a cannula (PE-50) for measuring the intravesical pressure was inserted into the bladder from the external urethral opening and fixed by a clip. After injecting about 200 μL of saline through the cannula that had been inserted into the bladder, the other side was connected to a pressure transducer to measure the intravesical pressure. Under a stereoscopic microscope observation, the pelvic nerve in the vicinity of the bladder was peeled and an electrode for nerve stimulation (unique Medical) was placed. The abdominal cavity was filled with mineral oil (MP BIOMEDICALS). After placing in a post-operative stabilization period, the pelvic nerve was subjected to electrical stimulation (stimulation voltage: 10 V, stimulation frequency: 8 Hz, pulse width: 0.3 msec, and stimulation time: 10 seconds) to elicit the elevation of intravesical pressure, using an electrical stimulator (Nihon Kohden). By repeating the electrical stimulation at an interval of 2 minutes while adjusting the voltage, the voltage was adjusted to elicit about 50% to 70% elevation of intravesical pressure elicited at 10 V. Thereafter, by repeating the electrical stimulation at an interval of 10 minutes, the increase in the intravesical pressure by electrical stimulation was stabilized three times or more, and the test substance (an administration amount of 3 mg/kg) was then administered from the catheter detained in the vein at a volume of 1 mL/kg, thus measuring an effect of the elevation of the intravesical pressure of the test substance for 1 hour. The test substance was dissolved in water supplemented with 10% dimethylsulfoxide and 10% Cremophor.

The response was applied to a personal computer through a PowerLab (registered trademark) and analyzed by LabChart (registered trademark). The AUC of each elevation of the intravesical pressure was calculated, the intravesical pressure elevation rate (% of pre) after the treatment with the test substance was calculated by taking an average value of the values measured three times before the treatment with the test substance as 100%, and the maximum effect during a period within one hour after administration of the compound was considered as the effect of the test substance.

The elevation rates (% of pre) of the intravesical pressure when some Example compounds were administered at 3 mg/kg are shown in Table 4.

TABLE 4

| Ex. | Increase rate (% of pre) of intravesical pressure |
|---|---|
| 3 | 251 |
| 10 | 145 |
| 11 | 132 |
| 13 | 132 |
| 15 | 142 |
| 21 | 155 |
| 28 | 184 |
| 34 | 134 |
| 42 | 149 |

TABLE 4-continued

| Ex. | Increase rate (% of pre) of intravesical pressure |
|---|---|
| 43 | 125 |
| 46 | 126 |
| 48 | 121 |
| 49 | 172 |
| 50 | 207 |
| 51 | 223 |
| 52 | 129 |
| 60 | 130 |
| 61 | 129 |
| 64 | 135 |
| 65 | 128 |
| 67 | 126 |
| 72 | 155 |
| 82 | 138 |
| 95 | 239 |
| 109 | 180 |
| 119 | 173 |
| 124 | 143 |
| 133 | 150 |
| 135 | 168 |
| 140 | 148 |
| 141 | 175 |
| 142 | 199 |
| 143 | 172 |

In addition, it was confirmed that the Example compounds evaluated in the present test do not cause an elevation of the intravesical pressure in a state in which electrical stimulation is not given, and the compounds alone do not show elevation of the intravesical pressure.

From the above, it was confirmed that the Example compounds listed in Table 4 alone do not show elevation of the intravesical pressure but have an action of enhancing effect on the pelvic nerve electrical stimulation-induced elevation of intravesical pressure in the anesthetized rats.

As shown in the results of each the tests above, it was confirmed that the compound of the formula (I) has a muscarinic $M_3$ receptor-positive allosteric modulator activity, and further, it enhances the bladder contraction in a nerve stimulation-dependent manner in in vitro, as well as enhances an elevation in the intravesical pressure in a nerve stimulation-dependent manner in in vivo. Accordingly, the compound of the formula (I) can be used to prevent or treat bladder/urinary tract diseases associated with bladder contractions via a muscarinic $M_3$ receptor, in particular, voiding dysfunction or urine storage dysfunction in the bladder/urethral diseases. The compound of the formula (I) can be used for preventing or treating, for example, voiding dysfunction or urine storage dysfunction in underactive bladder, hypotonic bladder, acontractile bladder, detrusor underactivity, neurogenic bladder, urethra relaxation failure, detrusor-external urethral sphincter dyssynergia, overactive bladder, urinary frequency, nocturia, urinary incontinence, benign prostatic hyperplasia, interstitial cystitis, chronic prostatitis, and urinary tract stones. In particular, the compound of the formula (I) can be used for preventing or treating voiding dysfunction or urine storage dysfunction in underactive bladder, hypotonic bladder, acontractile bladder, detrusor underactivity, and neurogenic bladder.

In addition, the compound of formula (I) can become a therapeutic drug that is more excellent in safety from the viewpoint that the compound alone does not show an agonistic effect on a muscarinic $M_3$ receptor, but shows an effect on enhancing the nerve stimulation-dependent bladder contraction, and accordingly, cholinergic side effects that have been reported in the existing drugs can be avoided.

A pharmaceutical composition including one or two or more kinds of the compound of the formula (I) as an active ingredient can be prepared using an excipient which is usually used in the art, that is, an excipient for a pharmaceutical preparation, a carrier for a pharmaceutical preparation, and the like, according to a method usually used.

Administration can be accomplished either by oral administration via tablets, pills, capsules, granules, powders, solutions, and the like, or parenteral administration via injections, such as intraarticular, intravenous, and intramuscular injections, suppositories, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one kind or two or more kinds of the active ingredients are mixed with at least one inactive excipient. In a conventional method, the composition may contain inactive additives such as a lubricant, a disintegrating agent, a stabilizer, or a solubilization assisting agent. If necessary, tablets or pills may be coated with a sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. The liquid composition may also include auxiliary agents such as a solubilization assisting agent, a moistening agent, and a suspending agent, sweeteners, flavors, aromatics, and antiseptics, in addition to the inert diluent.

The injections for parenteral administration include sterile aqueous or non-aqueous solution preparations, suspensions, or emulsions. The aqueous solvent includes, for example, distilled water for injection and saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

Examples of the agent for external use include ointments, hard plasters, creams, jellies, cataplasms, sprays, and lotions. The agent further contains generally used ointment bases, lotion bases, aqueous or non-aqueous liquid preparations, suspensions, emulsions, or the like.

As the transmucosal agents such as an inhaler and a transnasal agent, those in the form of a solid, liquid, or semi-solid state are used, and can be prepared in accordance with a method known in the related art. For example, a known excipient, and also a pH adjusting agent, an antiseptic, a surfactant, a lubricant, a stabilizing agent, a thickening agent, or the like may be appropriately added thereto. For the administration, an appropriate device for inhalation or blowing can be used. For example, a compound may be administered alone or as a powder of formulated mixture, or as a solution or suspension in combination with a pharmaceutically acceptable carrier, using a known device or sprayer such as a metered administration inhalation device. A dry powder inhaler or the like may be for single or multiple administration use, and a dry powder or a powder-containing capsule may be used. Alternatively, this may be in a form such as a pressurized aerosol spray that uses an appropriate propellant agent, for example, a suitable gas such as chlorofluoroalkanes, and carbon dioxide, or other forms.

Usually, in the case of oral administration, the daily dose is from about 0.001 mg/kg to 100 mg/kg, preferably from 0.1 mg/kg to 30 mg/kg, and more preferably from 0.1 mg/kg to 10 mg/kg, per body weight, administered in one portion or in 2 to 4 divided portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the present invention comprises 0.01% by weight to 100% by weight of, as an embodiment, 0.01% by weight to 50% by weight of, one or more of the compound of the formula (I) or a salt thereof which is the active ingredient.

The compound of the formula (I) may be used in combination with various agents for treating or preventing diseases on which the compound of the formula (I) is considered to show the effect. Such combined preparations may be administered simultaneously, or separately and continuously, or at a desired time interval. The preparations to be co-administered may be a blend, or may be prepared individually.

EXAMPLES

Hereinbelow, the production process for the compound of the formula (I) will be described in more detail with reference to Examples. Further, the present invention is not limited to the compounds described in the Examples below. Further, the production processes for the starting compounds will be described in Preparation Examples. In addition, the production processes for the compound of the formula (I) are not limited to the production processes of the specific Examples shown below, but the compound of the formula (I) can be prepared by a combination of these production processes or a method that is apparent to a person skilled in the art.

Further, in the present specification, nomenclature software such as ACD/Name (registered trademark, Advanced Chemistry Development, Inc.) may be used for nomenclature of compounds in some cases.

The powder X-ray diffraction is measured using RINT-TTRII under the conditions of a tube: Cu, a tube current: 300 mA, a tube voltage: 50 kV, a sampling width: 0.020°, a scanning speed: 4°/min, a wavelength: 1.54056 angstroms, and a measurement diffraction angle (2θ): 2.5° to 40°. Further, a device including data processing was handled in accordance with the method and procedure instructed in each device.

The values obtained from various spectra may cause some errors according to the direction of the crystal growth, particle sizes, measurement conditions, and the like in some cases. Accordingly, considering these errors, in the present specification, the description of diffraction angles (2θ (°)) in the powder X-ray diffraction patterns is measured value, but depending on the measuring conditions, these diffraction angles mean that error ranges which are usually acceptable may occur and mean that they are approximate values. Usually, the error range of the diffraction angle (2θ (°)) in the powder X-ray diffraction is ±0.2°. However, for the powder X-ray diffraction patterns, in terms of the properties of data, crystal lattice spacing and general patterns are important in the certification of crystal identity, and the diffraction angle and the diffraction intensity may vary slightly depending on the direction of crystal growth, the particle size, and the measurement condition, and they should not be strictly construed.

Moreover, the following abbreviations may be used in Examples, Preparation Examples, and Tables below in some cases.

PEx: Preparation Example No., Ex: Example No., PSyn: Preparation Example No. prepared by the same method, Syn: Example No. prepared by the same method, Structure: Structural chemical formula (Me represents methyl, Et represents ethyl, Ac represents acetyl, nPr represents n-propyl, iPr represents isopropyl, cPr represents cyclopropyl, iBu represents isobutyl, Boc represents tert-butoxycarbonyl, Ts represents 4-methylphenyl sulfonyl, COMU represents N-[({[(1Z)-1-cyano-2-ethoxy-2-oxoethylidene]amino}oxy) (morpholin-4-yl)methylene]-N-methylmethaminium hexafluorophosphate, WSCD.HCl represents N-[3-(dimethylamino)propyl]-N'-ethylcarbodiimide monohydrochloride, and ODS represents octadecylsilyl), Data: Physicochemical data, ESI+: m/z values in mass spectroscopy (Ionization method ESI, representing [M+H]$^+$ unless otherwise specified), ESI−: m/z values in mass spectroscopy (Ionization method ESI, representing [M−H]$^−$ unless otherwise specified), APCI/ESI+: APCI/ESI-MS (atmospheric pressure chemical ionization method APCI, representing [M+H]$^+$ unless otherwise specified; in which APCI/ESI means simultaneous measurement of APCI and ESI), EI: m/z values in mass spectroscopy (Ionization method EI, representing [M]$^+$ unless otherwise specified), CI: m/z values in mass spectroscopy (Ionization method CI, representing [M+H]$^+$ unless otherwise specified), NMR-DMSO-d: δ (ppm) of peaks in $^1$H-NMR in DMSO-d$_6$, s: singlet (spectrum), d: doublet (spectrum), t: triplet (spectrum), br: broad line (spectrum) (e.g.: brs), m: multiplet (spectrum). Further, HCl in the structural formula indicates that the compound is a monohydrochloride; 2HCl indicates that the compound is a dihydrochloride; 3HCl indicates that the compound is a trihydrochloride, and 2 maleic acid indicates that the compound is a dimalate.

In addition, for the sake of convenience, a concentration of mol/L is represented by M. For example, a 1 M aqueous sodium hydroxide solution means a 1 mol/L aqueous sodium hydroxide solution.

Preparation Example 1

A mixture of 4-[3-fluoro-5-(trifluoromethyl)phenyl]-5-{[(2R)-2-methylpyrrolidin-1-yl]methyl}-1,3-thiazol-2-amine (1.0 g), 5-chloropyrazine-2-carboxylic acid (685 mg), COMU (1.9 g), dioxane (10 mL), and N,N-diisopropylethylamine (1.5 mL) was stirred at room temperature for 1 hour. The reaction mixture was diluted with ethyl acetate, washed with water and saturated brine, dried over anhydrous magnesium sulfate, and concentrated under reduced pressure. The residue was purified by silica gel column chromatography (hexane-ethyl acetate) to obtain 5-chloro-N-(4-[3-fluoro-5-(trifluoromethyl)phenyl]-5-{[(2R)-2-methylpyrrolidin-1-yl]methyl}-1,3-thiazol-2-yl)pyrazine-2-carboxamide (800 mg) as a solid.

Preparation Example 2

To a mixture of 5-{[(2R)-2-methylpyrrolidin-1-yl]methyl}-4-[4-(trifluoromethyl)thiophen-2-yl]-1,3-thiazol-2- amine (2.9 g) and dichloromethane (60 mL) were added 5-chloropyrazine-2-carboxylic acid (1.7 g), N,N-dimethyl-4-aminopyridine (340 mg), and WSCD.HCl (2.1 g), followed by stirring at 40° C. for 15 minutes. The reaction mixture was cooled to room temperature, diluted with chloroform, and washed with a saturated aqueous sodium hydrogen carbonate solution. The aqueous layer was extracted with chloroform/methanol and the organic layer was combined and concentrated under reduced pressure. The residue was purified by silica gel column chromatography (chloroform-ethyl acetate) to obtain 5-chloro-N-(5-{[(2R)-2-methylpyrrolidin-1-yl]methyl}-4-[4-(trifluoromethyl)thiophen-2-yl]-1,3-thiazol-2-yl)pyrazine-2-carboxamide (2.4 g) as a solid.

Preparation Example 3

To a mixture of 5-chloropyrazine-2-carboxylic acid (30.5 g) and ethyl acetate (500 mL) were added thionyl chloride (55 mL) and N,N-dimethylformamide (0.57 mL), followed by stirring at 75° C. for 1.5 hours. The reaction mixture was concentrated under reduced pressure and toluene was added thereto, followed by carrying out a concentration operation.

A mixture of 4-(4-chlorothiophen-2-yl)-1,3-thiazol-2-amine (32.0 g) and cyclopentylmethyl ether (500 mL) was ice-cooled, and triethylamine (62 mL), and a mixture of the previously obtained compound and cyclopentylmethyl ether (100 mL) were slowly added thereto. The reaction mixture was stirred at room temperature for 2 days. To the reaction mixture was added water, followed by extraction with ethyl acetate/tetrahydrofuran. The organic layer was washed with water and saturated brine, dried over anhydrous magnesium sulfate, and concentrated under reduced pressure. The residue was mixed with diisopropyl ether and the solid was collected by filtration to obtain 5-chloro-N-[4-(4-chlorothiophen-2-yl)-1,3-thiazol-2-yl]pyrazine-2-carboxamide (46.6 g) as a solid.

Preparation Example 4

To a mixture of 6-methoxy-5-(trifluoromethyl)nicotinic acid (7.8 g) and dichloromethane (80 mL) were added N,O-dimethylhydroxylamine hydrochloride (4.3 g), WSCD.HCl (9.5 g), and N,N-diisopropylethylamine (30 mL) under ice-cooling. The reaction mixture was stirred at room temperature for 17 hours. The reaction mixture was concentrated under reduced pressure, and to the residue were added ethyl acetate and water, followed by stirring for 30 minutes. The organic layer was separated, the aqueous layer was extracted with ethyl acetate, and the organic layer was combined, dried over anhydrous magnesium sulfate, and then concentrated under reduced pressure. The residue was purified by silica gel column chromatography (hexane-ethyl acetate) to obtain N,6-dimethoxy-N-methyl-5-(trifluoromethyl)nicotinamide (5.0 g) as an oil.

Preparation Example 5

A mixture of N-(4-[3-fluoro-5-(trifluoromethyl)phenyl]-5-{[(2R)-2-methylpyrrolidin-1-yl]methyl}-1,3-thiazol-2-yl)acetamide (1.4 g), ethanol (10 mL), and a 6 M aqueous sodium hydroxide solution (5 mL) was stirred at 120° C. for 15 minutes under microwave irradiation. To the reaction mixture was added water, followed by extraction with ethyl acetate. The organic layer was washed with saturated brine, dried over anhydrous magnesium sulfate, and then concentrated under reduced pressure. The residue was purified by silica gel column chromatography (hexane-ethyl acetate) to obtain 4-[3-fluoro-5-(trifluoromethyl)phenyl]-5-{[(2R)-2-methylpyrrolidin-1-yl]methyl}-1,3-thiazol-2-amine (1.0 g) as an oil.

Preparation Example 6

A mixture of N-(5-{[(2R,5R)-2,5-dimethylpyrrolidin-1-yl]methyl}-4-[3-fluoro-5-(trifluoromethyl)phenyl]-1,3-thiazol-2-yl)acetamide (916 mg) and 80% sulfuric acid (10 mL) was stirred at 100° C. for 1 hour. The reaction mixture was cooled to 5° C. and alkalified by the addition of a 5 M aqueous sodium hydroxide solution and a saturated aqueous sodium hydrogen carbonate solution. The mixture was extracted with chloroform, and the organic layer was dried over anhydrous magnesium sulfate and then concentrated under reduced pressure. The residue was purified by basic silica gel column chromatography (hexane-ethyl acetate) to obtain 5-{[(2R,5R)-2,5-dimethylpyrrolidin-1-yl]methyl}-4-[3-fluoro-5-(trifluoromethyl)phenyl]-1,3-thiazol-2-amine (685 mg) as a solid.

Preparation Example 7

To a mixture of N-{5-[(diethylamino)methyl]-4-[3-fluoro-5-(trifluoromethyl)phenyl]-1,3-thiazol-2-yl}acetamide (392 mg) and ethanol (4 mL) was added a 6 M aqueous sodium hydroxide solution (2 mL), followed by heating to reflux for 5 hours. The reaction mixture was cooled to room temperature and water was added thereto, followed by extraction with chloroform. The organic layer was dried over anhydrous magnesium sulfate and then concentrated under reduced pressure. The residue was purified by basic silica gel column chromatography (hexane-ethyl acetate) to obtain 5-[(diethylamino)methyl]-4-[3-fluoro-5-(trifluoromethyl)phenyl]-1,3-thiazol-2-amine (264 mg) as a solid.

Preparation Example 8

To a mixture of tert-butyl (3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazine-1-carboxylate (19.9 g) and methanol (60 mL) was added hydrogen chloride (4 M dioxane solution, 180 mL), followed by stirring at room temperature for 1 hour. The reaction mixture was concentrated under reduced pressure. To the residue was added ethyl acetate (250 mL), followed by stirring at room temperature for 30 minutes. The solid was collected by filtration to obtain N-(4-[3-fluoro-5-(trifluoromethyl)phenyl]-5-{[(2R)-2-methylpyrrolidin-1-yl]methyl}-1,3-thiazol-2-yl)-5-[(2R)-2-methylpiperazin-1-yl]pyrazine-2-carboxamide trihydrochloride (20.1 g) as a solid.

Preparation Example 9

To a mixture of tert-butyl (3S)-4-(3-ethoxy-3-oxopropyl)-3-methylpiperazine-1-carboxylate (1.2 g) and ethanol (6 mL) was added hydrogen chloride (4 M ethyl acetate solution, 6 mL), followed by stirring at 80° C. for 1.5 hours. The reaction mixture was cooled to room temperature and stirred overnight. The solid was collected by filtration to obtain ethyl 3-[(2S)-2-methylpiperazin-1-yl]propanoate dihydrochloride (995 mg) as a solid.

Preparation Example 10

To a mixture of tert-butyl (2R)-2-ethylpyrrolidine-1-carboxylate (3.4 g) and dioxane (25 mL) was added hydrogen chloride (4 M dioxane solution, 25 mL), followed by stirring at room temperature for 1 hour. The reaction mixture was concentrated under reduced pressure, and to the residue were added diethyl ether, followed by stirring. The solid was collected by filtration to obtain (2R)-2-ethylpyrrolidine hydrochloride (2.1 g) as a solid.

Preparation Example 11

A mixture of {2-acetamido-4-[3-fluoro-5-(trifluoromethyl)phenyl]-1,3-thiazol-5-yl}methyl acetate (500 mg), diethylamine (0.3 mL), N,N-diisopropylethylamine (0.7 mL), and N-methylpyrrolidone (5 mL) was stirred at 100° C. for 2 hours. To the reaction mixture was added ethyl acetate, followed by washing with water and saturated brine. The organic layer was dried over anhydrous magnesium sulfate and then concentrated under reduced pressure. The residue was purified by silica gel column chromatography (hexane-ethyl acetate) to obtain N-{5-[(diethylamino)methyl]-4-[3-fluoro-5-(trifluoromethyl)phenyl]-1,3-thiazol-2-yl}acetamide (397 mg) as a solid.

Preparation Example 12

To a mixture of {2-acetamido-4-[3-chloro-5-(trifluoromethyl)phenyl]-1,3-thiazol-5-yl}methyl acetate (900 mg) and N,N-dimethylformamide (4 mL) were added (2R)-2-methylpyrrolidine (293 mg) and N,N-diisopropylethylamine (0.78 mL), followed by stirring at 110° C. for 30 minutes under microwave irradiation. To the reaction mixture was added water, followed by extraction with ethyl acetate. The organic layer was washed with water and saturated brine, dried over anhydrous magnesium sulfate, and then concentrated under reduced pressure. The residue was purified by basic silica gel column chromatography (hexane-ethyl acetate) to obtain N-(4-[3-chloro-5-(trifluoromethyl)phenyl]-5-{[(2R)-2-methylpyrrolidin-1-yl]methyl}-1,3-thiazol-2-yl)acetamide (896 mg) as a solid.

Preparation Example 13

A mixture of N-{4-[3-fluoro-5-(trifluoromethyl)phenyl]-1,3-thiazol-2-yl}acetamide (6.0 g), acetic acid (30 mL), a 36% aqueous formaldehyde solution (7.5 mL), and acetic anhydride (9 mL) was stirred at 170° C. for 15 minutes under microwave irradiation. The reaction mixture was concentrated under reduced pressure, and to the residue was added ethyl acetate. The mixture was washed with a saturated aqueous sodium hydrogen carbonate solution, water, and saturated brine, dried over anhydrous magnesium sulfate, and then concentrated under reduced pressure. The residue was purified by silica gel column chromatography (chloroform-methanol) and the obtained solid was mixed with diisopropyl ether. The solid was collected by filtration to obtain {2-acetamido-4-[3-fluoro-5-(trifluoromethyl)phenyl]-1,3-thiazol-5-yl}methyl acetate (2.6 g) as a solid.

Preparation Example 14

A mixture of ethyl 3-[(2R)-4-(5-{[4-(4-chlorothiophen-2-yl)-1,3-thiazol-2-yl]carbamoyl}pyrazin-2-yl)-2-methylpiperazin-1-yl]propanoate (1.0 g), acetic acid (10 mL), a 37% aqueous formaldehyde solution (1.5 mL), and acetic anhydride (1.8 mL) was stirred at 80° C. for 7 hours. The reaction mixture was cooled to room temperature and concentrated under reduced pressure. To the residue were added water and a saturated aqueous sodium hydrogen carbonate solution, followed by extraction with chloroform/isopropanol. The organic layer was dried over anhydrous magnesium sulfate and then concentrated under reduced pressure. The residue was purified by silica gel column chromatography (chloroform-methanol).

The obtained compound and pyridine (10 mL) were mixed, and acetic anhydride (0.9 mL) was added thereto, followed by stirring at room temperature for 30 minutes. To the reaction mixture was added water, followed by extraction with ethyl acetate. The organic layer was washed with water and a saturated aqueous sodium hydrogen carbonate solution, dried over anhydrous magnesium sulfate, and then concentrated under reduced pressure. The residue was purified by silica gel column chromatography (hexane-ethyl acetate) to obtain ethyl 3-[(2R)-4-(5-{[5-(acetoxymethyl)-4-(4-chlorothiophen-2-yl)-1,3-thiazol-2-yl] carbamoyl}pyrazin-2-yl)-2-methylpiperazin-1-yl]propanoate (566 mg) as a solid.

Preparation Example 15

A mixture of N-{4-[4-methoxy-3-(trifluoromethyl)phenyl]-1,3-thiazol-2-yl}acetamide (3.0 g), 37% aqueous formaldehyde solution (7.2 mL), acetic anhydride (9 mL), and acetic acid (30 mL) was stirred at 100° C. for 5 hours. The reaction mixture was concentrated under reduced pressure, and to the residue was added diisopropyl ether. The solid was collected by filtration to obtain {2-acetamido-4-[4-methoxy-3-(trifluoromethyl)phenyl]-1,3-thiazol-5-yl}methyl acetate (2.0 g) as a solid.

Preparation Example 16

A mixture of N-{4-[3-fluoro-5-(trifluoromethyl)phenyl]-1,3-thiazol-2-yl}acetamide (2.8 g), acetic acid (20 mL), a 36% aqueous formaldehyde solution (3.6 mL), and acetic anhydride (4.4 mL) was stirred at 170° C. for 30 minutes under microwave irradiation. The reaction mixture was concentrated under reduced pressure, and then the obtained solid was washed with methanol and collected by filtration.

The obtained solid (1.8 g) was mixed with N-methylpyrrolidone (20 mL), (2R)-2-methylpyrrolidine (608 mg), and N,N-diisopropylethylamine (2.5 mL), followed by stirring at 100° C. for 30 minutes. The reaction mixture was cooled to room temperature, and water was added thereto, followed by extraction with ethyl acetate. The organic layer was washed with saturated brine, dried over anhydrous magnesium sulfate, and then concentrated under reduced pressure. The residue was purified by silica gel column chromatography (hexane-ethyl acetate) to obtain N-(4-[3-fluoro-5-(trifluoromethyl)phenyl]-5-{[(2R)-2-methylpyrrolidin-1-yl]methyl}-1,3-thiazol-2-yl)acetamide (1.4 g) as a solid.

Preparation Example 17

N-[4-(4-Chlorothiophen-2-yl)-1,3-thiazol-2-yl]-2,2,2-trifluoroacetamide (5.0 g), (2R)-2-ethylpyrrolidine hydrochloride (4.8 g), N,N-diisopropylethylamine (5.5 mL), acetic acid (50 mL), and a 36% aqueous formaldehyde solution (2.5 mL) were mixed, followed by stirring at 60° C. for 1 hour. The reaction mixture was concentrated under reduced pressure and diluted with ethyl acetate. The mixture was washed with a saturated aqueous sodium hydrogen carbonate solution and saturated brine, dried over anhydrous magnesium sulfate, and then concentrated under reduced pressure. A mixture of the obtained compound, ethanol (50 mL), and a 6 M aqueous sodium hydroxide solution (14 mL) was stirred at 90° C. for 2 hours. The reaction mixture was cooled to room temperature, and water was added thereto, followed by extraction with ethyl acetate. The organic layer was washed with saturated brine, dried over anhydrous magnesium sulfate, and then concentrated under reduced pressure. The residue was purified by basic silica gel column chromatography (hexane-ethyl acetate) to obtain 4-(4-chlorothiophen-2-yl)-5-{[(2R)-2-ethylpyrrolidin-1-yl]methyl}-1,3-thiazol-2-amine (2.7 g) as a solid.

Preparation Example 18

To a mixture of ethyl 3-[(2S)-4-(5-{[4-(4-chlorothiophen-2-yl)-1,3-thiazol-2-yl]carbamoyl}pyrazin-2-yl)-2-methylpiperazin-1-yl]propanoate (20 g) and acetic acid (200 mL) were added paraformaldehyde (3.5 g) and (2R)-2-methylpyrrolidine (6.6 g), followed by stirring at 75° C. for 3.5 hours. The reaction mixture was concentrated under reduced pressure. To the residue were added ethyl acetate (250 mL), toluene (125 mL), and water (200 mL), followed by neutralization by the addition of sodium carbonate. The organic layer was separated, the aqueous layer was extracted with ethyl acetate/toluene, the organic layers were dried over anhydrous sodium sulfate, and then amino silica gel (40 g) was added thereto. The mixture was stirred at room temperature for 30 minutes, the insoluble materials were separated by filtration and the filtrate was concentrated under reduced pressure. The residue was purified by basic silica gel column chromatography (hexane-ethyl acetate) to obtain ethyl 3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoate (19.5 g) as a solid.

Preparation Example 19

4-[3-Fluoro-5-(trifluoromethyl)phenyl]-1,3-thiazol-2-amine (2.8 g), pyridine (10 mL), and acetic anhydride (4 mL) were mixed, by stirring at 60° C. for 1 hour. The reaction mixture was cooled to room temperature, water was added thereto, and the generated solid was collected by filtration. The obtained solid was washed with methanol and the solid was collected by filtration to obtain N-{4-[3-fluoro-5-(trifluoromethyl)phenyl]-1,3-thiazol-2-yl}acetamide (2.9 g) as a solid.

Preparation Example 20

A mixture of 4-(4-chlorothiophen-2-yl)-1,3-thiazol-2-amine (5.0 g), dichloromethane (100 mL), and triethylamine (5.0 mL) was stirred and ice-cooled, and trifluoroacetic anhydride (5 mL) was added thereto, followed by stirring at room temperature for 1 hour. The reaction mixture was diluted with chloroform, washed with water and saturated brine, dried over anhydrous magnesium sulfate, and then concentrated under reduced pressure. The residue was purified by silica gel column chromatography (hexane-ethyl acetate). The obtained solid was washed with hexane and the solid was collected by filtration to obtain N-[4-(4-chlorothiophen-2-yl)-1,3-thiazol-2-yl]-2,2,2-trifluoroacetamide (6.0 g) as a solid.

Preparation Example 21

A mixture of tert-butyl (3S)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazine-1-carboxylate (410 mg), hydrogen chloride (4 M dioxane solution, 4 mL), and methanol (2 mL) was stirred at room temperature for 1 hour. To the reaction mixture was added ethyl acetate, followed by concentration under reduced pressure. A mixture of the obtained compound, N-methylpyrrolidone (6 mL), ethyl 3-bromopropanoate (0.4 mL), and potassium carbonate (683 mg) was stirred at 100° C. for 2 hours. The reaction mixture was cooled to room temperature and diluted with ethyl acetate. The mixture was washed with water and saturated brine, dried over anhydrous magnesium sulfate, and then concentrated under reduced pressure. The residue was purified by silica gel column chromatography (hexane-ethyl acetate) to obtain ethyl 3-[(3S)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]propanoate (205 mg).

Preparation Example 22

A mixture of tert-butyl (3R)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-3-methylpiperazine-1-carboxylate (271 mg), hydrogen chloride (4 M dioxane solution, 4 mL), and methanol (2 mL) was stirred at room temperature for 1 hour. To the reaction mixture was added ethyl acetate, followed by concentration under reduced pressure. A mixture of the residue, N,N-dimethylformamide (4 mL), ethyl bromoacetate (0.05 mL), and N,N-diisopropylethylamine (0.3 mL) was stirred at room temperature overnight. The reaction mixture was diluted with ethyl acetate, washed with water and saturated brine, dried over anhydrous magnesium sulfate, and then concentrated under reduced pressure. The residue was purified by silica gel column chromatography (hexane-ethyl acetate) and purified by basic silica gel column chromatography (hexane-ethyl acetate) to obtain ethyl [(3R)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-3-methylpiperazin-1-yl]acetate (154 mg) as a solid.

Preparation Example 23

A mixture of 1-[4-hydroxy-3-(trifluoromethyl)phenyl]ethanone (1 g), iodoethane (1.2 mL), cesium carbonate (1.9 g), and N,N-dimethylformamide (15 mL) was stirred at 60° C. for 3 hours. The reaction mixture was cooled to room temperature, and water was added thereto, followed by extraction with ethyl acetate. The organic layer was washed with water and saturated brine, dried over anhydrous sodium sulfate, and then concentrated under reduced pressure. The residue was purified by silica gel column chromatography (hexane-ethyl acetate) to obtain 1-[4-ethoxy-3-(trifluoromethyl)phenyl]ethanone (1.1 g) as a solid.

Preparation Example 24

To a mixture of 4-(4,5-dimethylthiophen-2-yl)-1,3-thiazol-2-amine (500 mg) and dichloromethane (10 mL) were added 5-chloropyrazine-2-carboxylic acid (530 mg), WSCD.HCl (730 mg), and N,N-dimethyl-4-aminopyridine (100 mg), followed by stirring at 40° C. for 30 minutes. The reaction mixture was cooled to room temperature, and ethyl acetate, water, and a saturated aqueous sodium hydrogen carbonate solution were added thereto. The insoluble materials were separated by filtration over Celite and the filtrate was extracted with ethyl acetate. The organic layer was washed with saturated brine, dried over anhydrous magnesium sulfate, and then concentrated under reduced pressure. To a mixture of the obtained compound and N-methylpyrrolidone (16 mL) were added ethyl 3-(piperazin-1-yl)propanoate dihydrochloride (1.0 g) and N,N-diisopropylethylamine (3 mL), followed by stirring at 80° C. for 2 hours. The reaction mixture was cooled to room temperature, and water and ethyl acetate were added thereto. The organic layer was washed with water and saturated brine, dried over anhydrous magnesium sulfate, and then concentrated under reduced pressure. The residue was purified by silica gel column chromatography (chloroform-ethyl acetate). The obtained compound was washed with diisopropyl ether (4 mL) and hexane (20 mL), and the solid was collected by filtration to obtain ethyl 3-[4-(5-{[4-(4,5-dimethylthiophen-2-yl)-1,3-thiazol-2-yl]carbamoyl}pyrazin-2-yl)piperazin-1-yl]propanoate (954 mg) as a solid.

Preparation Example 25

To a mixture of N-(4-[3-fluoro-5-(trifluoromethyl)phenyl]-5-{[(2R)-2-methylpyrrolidin-1-yl]methyl}-1,3-thiazol-2-yl)-5-[(2R)-2-methylpiperazin-1-yl]pyrazine-2-carboxamide trihydrochloride (16.1 g) and N,N-dimethylformamide (400 mL) was added potassium carbonate (11.5 g), followed by stirring at room temperature for 5 minutes. To the reaction mixture was added ethyl bromoacetate (2.65 mL), followed by stirring at room temperature for 1 hour. To the reaction mixture was added ethyl bromoacetate (0.8 mL), followed by stirring at room temperature for 1.5 hours. The reaction mixture was poured into water, followed by extraction with ethyl acetate. The organic layer was washed with water and saturated brine, and anhydrous magnesium sulfate and activated carbon were added thereto. The insoluble materials were separated by filtration and the filtrate was concentrated under reduced pressure. The residue was purified by basic silica gel column chromatography (hexane-ethyl acetate) to obtain ethyl [(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]acetate (11.0 g) as a solid.

Preparation Example 26

To a mixture of 1-[4-hydroxy-3-(trifluoromethyl)phenyl]ethanone (1 g) and acetonitrile (10 mL) were added 1-bromopropane (0.9 mL), potassium carbonate (1.7 g), and tetrabutylammonium iodide (180 mg), followed by stirring at room temperature overnight. The insoluble materials were separated by filtration and the filtrate was concentrated under reduced pressure. The residue was purified by silica gel column chromatography (hexane-ethyl acetate) to obtain 1-[4-propoxy-3-(trifluoromethyl)phenyl]ethanone (1.2 g) as an oil.

Preparation Example 27

To a mixture of copper iodide (I) (9.4 g) and diethyl ether (180 mL) was added dropwise methyllithium (about 1 M diethyl ether solution, 100 mL) at an internal temperature of 0° C. to 5° C. over 30 minutes, followed by stirring for 15 minutes. To the reaction mixture was added dropwise a solution of tert-butyl (2S)-2-({[(4-methylphenyl)sulfonyl]oxy}methyl)pyrrolidine-1-carboxylate (7.0 g) in dichloromethane (30 mL) at an internal temperature of 5° C. or lower over 20 minutes, followed by stirring at room temperature for 2.5 hours. To the reaction mixture was added dropwise a saturated aqueous ammonium chloride solution, followed by extraction with ethyl acetate. The organic layer was dried over anhydrous sodium sulfate and then concentrated under reduced pressure. The residue was purified by silica gel column chromatography (hexane-ethyl acetate) to obtain tert-butyl (2R)-2-ethylpyrrolidine-1-carboxylate (3.5 g) as an oil.

Preparation Example 28

A mixture of tert-butyl (2R)-2-methylpiperazine-1-carboxylate (3.0 g), N,N-dimethylformamide (30 mL), ethyl bromoacetate (2 mL), and potassium carbonate (5.0 g) was stirred at room temperature for 1 hour. To the reaction mixture was added ethyl acetate, followed by washing with water and saturated brine. The organic layer was dried over anhydrous magnesium sulfate and then concentrated under reduced pressure. The residue was purified by silica gel column chromatography (chloroform-methanol) to obtain tert-butyl (2R)-4-(2-ethoxy-2-oxoethyl)-2-methylpiperazine-1-carboxylate (4.0 g) as an oil.

Preparation Example 29

To a mixture of 5-chloro-N-[4-(4-chlorothiophen-2-yl)-1,3-thiazol-2-yl]pyrazine-2-carboxamide (25.0 g) and N-methylpyrrolidone (150 mL) were added N,N-diisopropylethylamine (50 mL) and ethyl 3-[(2S)-2-methylpiperazin-1-yl]propanoate dihydrochloride (21.2 g), followed by stirring at 60° C. for 1.5 hours. The reaction mixture was cooled to room temperature, and ethyl acetate and water were added thereto, followed by extraction with ethyl acetate. The organic layer was washed with water and saturated brine, and anhydrous magnesium sulfate and activated carbon were added thereto. The insoluble materials were separated by filtration and the filtrate was concentrated under reduced pressure. The residue was purified by silica gel column chromatography (chloroform-ethyl acetate). The obtained compound was mixed with diisopropyl ether (40 mL) and hexane (120 mL), followed by stirring at room temperature for 15 minutes. The solid was collected by filtration to obtain ethyl 3-[(2S)-4-(5-{[4-(4-chlorothiophen-2-yl)-1,3-thiazol-2-yl]carbamoyl}pyrazin-2-yl)-2-methylpiperazin-1-yl]propanoate (29.7 g) as a solid.

Preparation Example 30

To a mixture of 1-[3-fluoro-5-(trifluoromethyl)phenyl]ethanone (78 g) and tetrahydrofuran (625 mL) was added phenyltrimethylammonium tribromide (143 g), followed by stirring at room temperature for 1 hour. The insoluble materials were separated by filtration and the filtrate was concentrated under reduced pressure.

The obtained compound and ethanol (625 mL) were mixed, and thiourea (35 g) was added thereto, followed by stirring at 65° C. to 75° C. for 2 hours. The reaction mixture was ice-cooled, and water (625 mL) was added thereto. To the mixture was added a 1 M sodium hydroxide (600 mL), followed by stirring for 30 minutes. The solid was collected by filtration, and ethanol (30% aqueous, 600 mL) was added thereto and dissolved at 76° C. The obtained solution was cooled to room temperature and stirred overnight. The mixture was ice-cooled and stirred for 2 hours, and then the precipitated solid was collected by filtration to obtain 4-[3-fluoro-5-(trifluoromethyl)phenyl]-1,3-thiazol-2-amine (56.9 g) as a solid.

Preparation Example 31

To a mixture of 1-(4-bromothiophen-2-yl)ethanone (20 g) and N-methylpyrrolidone (400 mL) were added sodium trifluoroacetate (140 g) and copper iodide (I) (100 g), followed by stirring at 200° C. for 2.5 hours. The reaction mixture was cooled to room temperature, water and ethyl acetate were added thereto, and the insoluble materials were separated by filtration over Celite. The organic layer of the filtrate was separated, washed with water and saturated brine, dried over anhydrous magnesium sulfate, and then concentrated under reduced pressure. The residue was purified by silica gel column chromatography (hexane-ethyl acetate) and purified by basic silica gel column chromatography (hexane-ethyl acetate) to obtain 1-[4-(trifluoromethyl)thiophen-2-yl]ethanone (4.1 g) as an oil.

Preparation Example 32

To a mixture of N,6-dimethoxy-N-methyl-5-(trifluoromethyl)nicotinamide (3.7 g) and tetrahydrofuran (40 mL) was added methylmagnesium bromide (3 M tetrahydrofuran solution, 7 mL) under ice-cooling, followed by stirring for 1 hour. To the reaction mixture was added a saturated aqueous ammonium chloride solution, followed by extraction with ethyl acetate. The organic layer was dried over anhydrous magnesium sulfate and then concentrated under reduced pressure. The residue was purified by silica gel column chromatography (hexane-ethyl acetate) to obtain 1-[6-methoxy-5-(trifluoromethyl)pyridin-3-yl]ethanone (3.0 g) as an oil.

Preparation Example 33

A mixture of 1-(3,5-dichloro-4-hydroxyphenyl)ethanone (10.0 g), N,N-dimethylformamide (100 mL), potassium carbonate (8.1 g), and methyl iodide (6.1 mL) was stirred at room temperature overnight. To the reaction mixture was added water, followed by extraction with ethyl acetate. The organic layer was washed with 1 M hydrochloric acid and saturated brine, and dried over anhydrous magnesium sulfate. The mixture was filtered using a basic silica gel and the filtrate was concentrated under reduced pressure to obtain 1-(3,5-dichloro-4-methoxyphenyl)ethanone (7.6 g) as a solid.

Preparation Example 34

To a mixture of ethyl 6-methoxy-5-(trifluoromethyl)nicotinate (5.5 g) and ethanol (40 mL) were added a 3 M aqueous sodium hydroxide solution (40 mL), followed by stirring at 60° C. for 30 minutes. The reaction mixture was cooled to room temperature and concentrated under reduced pressure. To the residue was added 1 M hydrochloric acid (120 mL) and the mixture was stirred for 1 hour. The precipitated solid was collected by filtration to obtain 6-methoxy-5-(trifluoromethyl)nicotinic acid (4.4 g) as a solid.

Preparation Example 35

A mixture of 5-bromo-2-methoxy-3-(trifluoromethyl)pyridine (7.8 g), palladium acetate (II) (170 mg), 1,1'-bis(diphenylphosphino)ferrocene (840 mg), N,N-diisopropylethylamine (10 mL), ethanol (80 mL), and N,N-dimethylformamide (80 mL) was stirred at 90° C. for 19 hours under a carbon monoxide atmosphere. The reaction mixture was cooled to room temperature, and poured into water (500 mL) and ethyl acetate (500 mL), followed by stirring for 30 minutes. The organic layer was separated, washed with water and saturated brine, dried over anhydrous sodium sulfate, and then concentrated under reduced pressure. The residue was purified by silica gel column chromatography (hexane-ethyl acetate) to obtain ethyl 6-methoxy-5-(trifluoromethyl)nicotinate (5.5 g) as a solid.

Preparation Example 36

2-Methoxy-3-(trifluoromethyl)pyridine (8 g), 1,3-dibromo-5,5-dimethylimidazolidine-2,4-dione (17 g), and trifluoroacetic acid (32 mL) were mixed, followed by stirring at room temperature for 22 hours. The reaction mixture was concentrated under reduced pressure, and to the residue was added diisopropyl ether. The precipitated solid was separated by filtration and the filtrate was concentrated under reduced pressure. The residue was purified by silica gel column chromatography (hexane-ethyl acetate) to obtain 5-bromo-2-methoxy-3-(trifluoromethyl)pyridine (9.4 g) as an oil.

Preparation Example 37

To a mixture of 1-[4-hydroxy-3-(trifluoromethyl)phenyl]ethanone (1 g) and tetrahydrofuran (10 mL) were added 2-propanol (0.46 mL), a 40% diethylazodicarboxylate solution in toluene (2.3 mL) and triphenylphosphine (1.6 g), followed by stirring at room temperature overnight. The reaction mixture was concentrated under reduced pressure and the residue was purified by silica gel column chromatography (hexane-ethyl acetate) to obtain 1-[4-isopropoxy-3-(trifluoromethyl)phenyl]ethanone (1.0 g) as an oil.

Preparation Example 38

A mixture of 1-[4-chloro-3-(trifluoromethyl)phenyl]ethanone (1.0 g), cyclopropylboronic acid (780 mg), dicyclohexyl (2',6'-dimethoxybiphenyl-2-yl)phosphine (185 mg), tripotassium phosphate (3.0 g), palladium acetate (II) (51 mg), toluene (10 mL), and water (1 mL) was stirred at 100° C. for 3 hours under an argon atmosphere. The reaction mixture was cooled to room temperature, ethyl acetate and water were added thereto, and the insoluble materials were separated by filtration. The filtrate was extracted with ethyl acetate and the organic layer was washed with saturated brine, dried over anhydrous magnesium sulfate, and then concentrated under reduced pressure. The residue was purified by silica gel column chromatography (hexane-ethyl acetate) to obtain 1-[4-cyclopropyl-3-(trifluoromethyl)phenyl]ethanone (1.0 g) as an oil.

Preparation Example 39

To a mixture of 1-(4-bromothiophen-2-yl)ethanone (9.4 g), toluene (200 mL) and water (100 mL) were added cyclopropylboronic acid (12.0 g), tetrakis(triphenylphosphine) palladium (0) (5.34 g), cesium carbonate (73.6 g), and tri-tert-butylphosphine (2.3 mL), followed by stirring at 80° C. for 3 hours. The reaction mixture was filtrated over Celite, and to the filtrate were added water and diethyl ether. The organic layer was separated, dried over anhydrous magnesium sulfate, and then concentrated under reduced pressure. The residue was purified by silica gel column chromatography (hexane-ethyl acetate) to obtain 1-(4-cyclopropylthiophen-2-yl)ethanone (6.7 g) as an oil.

Preparation Example 40

A mixture of 3-bromo-5-(trifluoromethyl)benzoic acid (10.0 g), thionylchloride (40 mL), and N,N-dimethylformamide (1 droplet) was stirred at 80° C. for 2 hours. The reaction mixture was concentrated under reduced pressure, followed by carrying out a concentration operation with toluene twice and then drying under reduced pressure.

To a mixture of toluene (150 mL) and magnesium chloride (3.6 g) were added dimethyl malonate (5.1 mL) and triethylamine (12 mL), followed by stirring at room temperature for 1.5 hours. To the reaction mixture was first added dropwise a mixture of the obtained compound and toluene (50 mL) under stirring, followed by stirring at room temperature for 18 hours. To the reaction mixture was added 6 M hydrochloric acid (50 mL), and then water (300 mL) was added thereto, followed by extraction with ethyl acetate. The organic layer was washed with saturated brine, dried over anhydrous magnesium sulfate, and then concentrated under reduced pressure. The residue was mixed with dimethylsulfoxide (50 mL) and water (5 mL), followed by stirring at 160° C. for 1 hour. The reaction mixture was cooled to room temperature, and water (300 mL) was added thereto, followed by extraction with ethyl acetate. The organic layer was washed with water and saturated brine, dried over anhydrous magnesium sulfate, and then concentrated under reduced pressure to obtain 1-[3-bromo-5-(trifluoromethyl)phenyl]ethanone (10.0 g) as an oil.

Preparation Example 41

To a mixture of zinc powder (2.0 g), cobalt bromide (II) (600 mg), and acetonitrile (30 mL) was added trifluoroacetic acid (0.15 mL) under an argon atmosphere, followed by stirring at room temperature for 15 minutes. To the reaction mixture were added 5-bromo-1-fluoro-2-methoxy-3-(trifluoromethyl)benzene (5.0 g) and acetic anhydride (2.1 mL), followed by stirring at room temperature for 17 hours. To the reaction mixture was added 1 M hydrochloric acid (30 mL), followed by extraction with diethyl ether. The organic layer was washed with water and saturated brine, and concentrated under reduced pressure. The residue was purified by silica gel column chromatography (hexane-diethyl ether) to obtain 1-[3-fluoro-4-methoxy-5-(trifluoromethyl)phenyl]ethanone (1.6 g) as an oil.

Preparation Example 42

To a mixture of 1-[4-hydroxy-3-(trifluoromethyl)phenyl]ethanone (3.0 g), N,N-dimethylformamide (36 mL), and water (3.6 mL) were added sodium chloro(difluoro)acetate (5.8 g) and cesium carbonate (7.2 g), followed by stirring at 100° C. for 3 hours. To the reaction mixture was added water, followed by extraction with ethyl acetate. The organic layer was washed with water and saturated brine, and concentrated under reduced pressure. The residue was purified by silica gel column chromatography (hexane-ethyl acetate). To a mixture of the obtained compound (3.8 g) and tetrahydrofuran (50 mL) was added phenyltrimethylammonium tribromide (5.7 g), followed by stirring at room temperature for 45 minutes. The precipitated insoluble materials were separated by filtration and the filtrate was concentrated under reduced pressure. To a mixture of the residue and ethanol (50 mL) was added thiourea (1.5 g), followed by stirring at 80° C. for 2 hours. The reaction mixture was cooled to room temperature, and water (30 mL) and a 1 M aqueous sodium hydroxide solution (30 mL) were added thereto, followed by extraction with ethyl acetate. The organic layer was washed with saturated brine, dried over anhydrous magnesium sulfate, and then concentrated under reduced pressure. To the residue was added diisopropyl ether and hexane, and the generated solid was collected by filtration to obtain 4-[4-(difluoromethoxy)-3-(trifluoromethyl)phenyl]-1,3-thiazol-2-amine (3.5 g) as a solid.

Preparation Example 43

To a mixture of 5-chloro-N-(4-[4-ethoxy-3-(trifluoromethyl)phenyl]-5-{[(2R)-2-methylpyrrolidin-1-yl]methyl}-1,3-thiazol-2-yl)pyrazine-2-carboxamide (407 mg) and N-methylpyrrolidone (6 mL) were added tert-butyl (3R)-3-methylpiperazine-1-carboxylate (400 mg) and N,N-diisopropylethylamine (0.7 mL), followed by stirring at 80° C. for 4 hours. The reaction mixture was cooled to room temperature, and water was added thereto, followed by extraction with ethyl acetate. The organic layer was dried over anhydrous magnesium sulfate and then concentrated under reduced pressure. The residue was purified by silica gel column chromatography (hexane-ethyl acetate).

A mixture of the obtained compound, hydrogen chloride (4 M dioxane solution, 6 mL), and methanol (2 mL) was stirred at room temperature for 4 hours. To the reaction mixture was added ethyl acetate (20 mL), and the solid was collected by filtration to obtain N-(4-[4-ethoxy-3-(trifluoromethyl)phenyl]-5-{[(2R)-2-methylpyrrolidin-1-yl]methyl}-1,3-thiazol-2-yl)-5-[(2R)-2-methylpiperazin-1-yl]pyrazine-2-carboxamide trihydrochloride (623 mg) as a solid.

Preparation Example 44

To a mixture of tert-butyl (2S)-2-(hydroxymethyl)pyrrolidine-1-carboxylate (17 g), triethylamine (17.7 mL), 1-methyl-1H-imidazole (10.1 mL), and dichloromethane (255 mL) was added p-toluenesulfonyl chloride (17.7 g) under ice-cooling, followed by stirring at the same temperature for 1 hour. To the reaction mixture was added water, followed by extraction with dichloromethane. The organic layer was washed with saturated brine, dried over anhydrous sodium sulfate, and then concentrated under reduced pressure. The residue was purified by silica gel column chromatography (hexane-ethyl acetate) to obtain tert-butyl (2S)-2-({[(4-methylphenyl)sulfonyl]oxy}methyl)pyrrolidine-1-carboxylate (29.5 g) as an oil.

Preparation Example 45

A mixture of tert-butyl (3S)-3-methylpiperazine-1-carboxylate (5 g), ethyl acrylate (7.2 mL), and ethanol (15 mL) was heated and refluxed for 24 hours. The reaction mixture was concentrated under reduced pressure, and to the residue was added diethyl ether, followed by extraction with 1 M hydrochloric acid. The aqueous layer was alkalified to pH 8 by the addition of a 1 M aqueous sodium hydroxide solution and sodium hydrogen carbonate, and extracted with ethyl acetate. The organic layer was dried over anhydrous sodium sulfate and then concentrated under reduced pressure. The residue was purified by silica gel column chromatography (chloroform-methanol) to obtain tert-butyl (3 S)-4-(3-ethoxy-3-oxopropyl)-3-methylpiperazine-1-carboxylate (7.5 g) as an oil.

Example 1

To a mixture of ethyl 3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl] propanoate (10.2 g), tetrahydrofuran (50 mL), and ethanol (50 mL) was added a 1 M aqueous sodium hydroxide solution (50 mL), followed by stirring at 50° C. for 30 minutes. The reaction mixture was cooled to room temperature, and 1 M hydrochloric acid (50 mL) and water (100 mL) were added thereto, followed by extraction with chloroform. The organic layer was dried over anhydrous magnesium sulfate and then concentrated under reduced pressure. The residue was purified by silica gel column chromatography (chloroform-methanol) to obtain a solid (6.0 g) of 3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid.

To a mixture of the obtained solid and tetrahydrofuran (100 mL) was added hydrogen chloride (4 M dioxane solution, 12 mL), and the mixture was concentrated under reduced pressure. To the residue were added acetonitrile (200 mL) and water (12 mL), followed by stirring at 70° C. for 15 minutes, and then cooling at room temperature. To the mixture was added acetonitrile (100 mL), followed by stirring at room temperature for 1 hour. The solid was collected by filtration and dried to obtain 3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid dihydrochloride (6.7 g) as a solid.

Example 2

Under an argon gas flow, to a mixture of ethyl 3-(4-{5-[(4-[3-bromo-5-(trifluoromethyl)phenyl]-5-{[(2S)-2-isopropylpyrrolidin-1-yl]methyl}-1,3-thiazol-2-yl)carbamoyl] pyrazin-2-yl}piperazin-1-yl)propanoate (660 mg), zinc powder (30 mg), biphenyl-2-yl(di-tert-butyl)phosphine (60 mg), and N,N-dimethylacetamide (13 mL) were added zinc cyanide (160 mg) and palladium trifluoroacetate (II) (30 mg), followed by stirring at 100° C. for 1 hour. The reaction mixture was cooled to room temperature, and ethyl acetate was added thereto. The organic layer was washed with saturated brine, dried over anhydrous magnesium sulfate, and then concentrated under reduced pressure. The residue was purified by silica gel column chromatography (hexane-ethyl acetate).

To a mixture of the obtained compound (401 mg), ethanol (5 mL), and tetrahydrofuran (5 mL) was added a 1 M aqueous sodium hydroxide solution (3 mL), followed by stirring at 50° C. for 30 minutes. The reaction mixture was concentrated under reduced pressure and the residue was purified by ODS column chromatography (acetonitrile-water). The obtained solid was mixed with hexane (20 mL) and diethyl ether (4 mL), and the solid was collected by filtration to obtain sodium 3-(4-{5-[(4-[3-cyano-5-(trifluoromethyl)phenyl]-5-{[(2S)-2-isopropylpyrrolidin-1-yl]methyl}-1,3-thiazol-2-yl)carbamoyl]pyrazin-2-yl}piperazin-1-yl)propanoate (149 mg) as a solid.

Example 3

To a mixture of 5-chloro-N-(5-{[(2R)-2-methylpyrrolidin-1-yl]methyl}-4-[4-(trifluoromethyl)thiophen-2-yl]-1,3-thiazol-2-yl)pyrazine-2-carboxamide (300 mg) and N-methylpyrrolidone (6 mL) were added ethyl 3-[(3R)-3-methylpiperazin-1-yl]propanoate dihydrochloride (500 mg) and N,N-diisopropylethylamine (0.64 mL), followed by stirring at 90° C. for 2 hours. The reaction mixture was cooled to room temperature, diluted with ethyl acetate, and washed with water and saturated brine. The organic layer was dried over anhydrous magnesium sulfate and concentrated under reduced pressure. The residue was purified by basic silica gel column chromatography (hexane-ethyl acetate).

To a mixture of the obtained compound, ethanol (6 mL), and tetrahydrofuran (6 mL) was added a 1 M aqueous sodium hydroxide solution (3.5 mL), followed by stirring at 60° C. for 30 minutes. The reaction mixture was cooled to room temperature and concentrated under reduced pressure. The residue was purified by ODS column chromatography (acetonitrile—0.1% aqueous formic acid solution) to obtain a solid (204 mg). To a mixture of the obtained solid and ethyl acetate was added hydrogen chloride (4 M ethyl acetate solution, 0.25 mL). The reaction mixture was concentrated under reduced pressure to obtain 3-[(3R)-3-methyl-4-{5-[(5-{[(2R)-2-methylpyrrolidin-1-yl]methyl}-4-[4-(trifluoromethyl)thiophen-2-yl]-1,3-thiazol-2-yl)carbamoyl]pyrazin-2-yl}piperazin-1-yl]propanoic acid dihydrochloride (155 mg) as a solid.

Example 4

To a mixture of 5-chloro-N-(5-{[(2R)-2-methylpiperidin-1-yl]methyl}-4-[3-methyl-5-(trifluoromethyl)phenyl]-1,3-thiazol-2-yl)pyrazine-2-carboxamide (300 mg) and N-methylpyrrolidone (6 mL) were added ethyl 3-(piperazin-1-yl) propanoate dihydrochloride (250 mg) and N,N-diisopropylethylamine (0.7 mL), followed by stirring at 80° C. for 2 hours. The reaction mixture was cooled to room temperature, and water and ethyl acetate were added thereto. The organic layer was separated, washed with water and saturated brine, dried over anhydrous magnesium sulfate, and then concentrated under reduced pressure. The residue was purified by silica gel column chromatography (hexane-ethyl acetate).

To a mixture of the obtained residue, ethanol (5 mL), and tetrahydrofuran (5 mL) was added a 1 M aqueous sodium hydroxide solution (3 mL), followed by stirring at 50° C. for 30 minutes. The reaction mixture was cooled to room temperature and concentrated under reduced pressure. The residue was purified by ODS column chromatography (acetonitrile-water) to obtain a solid (298 mg). The obtained solid was mixed with hexane (10 mL) and diethyl ether (2 mL), and the solid was collected by filtration to obtain sodium 3-(4-{5-[(5-{[(2R)-2-methylpiperidin-1-yl] methyl}-4-[3-methyl-5-(trifluoromethyl)phenyl]-1,3-thiazol-2-yl)carbamoyl]pyrazin-2-yl}piperazin-1-yl)propanoate (284 mg) as a solid.

Example 5

A mixture of ethyl 3-[(2R)-4-(5-{[5-(acetoxymethyl)-4-(4-chlorothiophen-2-yl)-1,3-thiazol-2-yl] carbamoyl}pyrazin-2-yl)-2-methylpiperazin-1-yl]propanoate (200 mg), dimethylamine (2M tetrahydrofuran solution, 2 mL), and N-methylpyrrolidone (4 mL) was stirred at 80° C. for 3 hours. The reaction mixture was cooled to room temperature, diluted with ethyl acetate, and washed with water and saturated brine. The organic layer was dried over anhydrous magnesium sulfate and then concentrated under reduced pressure. The residue was purified by basic silica gel column chromatography (hexane-ethyl acetate) and purified by silica gel column chromatography (hexane-ethyl acetate). The obtained compound was mixed with ethanol (2 mL) and tetrahydrofuran (2 mL), and a 1 M aqueous sodium hydroxide solution (1 mL) was added thereto, followed by stirring at room temperature for 1 hour. To the reaction mixture were added 1 M hydrochloric acid (1 mL) and water, the mixture was extracted with chloroform/isopropanol, and the organic layer was washed with water and saturated brine. The organic layer was dried over anhydrous magnesium sulfate and then concentrated under reduced pressure. To a mixture of the obtained compound and ethyl acetate was added hydrogen chloride (4 M ethyl acetate solution, 1 mL). The reaction mixture was concentrated under reduced pressure, and to the residue was added ethyl acetate. The solid was collected by filtration to obtain 3-{(2R)-4-[5-({4-(4-chlorothiophen-2-yl)-5-[(dimethylamino)methyl]-1,3-thiazol-2-yl}carbamoyl)pyrazin-2-yl]-2-methylpiperazin-1-yl}propanoic acid dihydrochloride (33 mg) as a solid.

Example 6

A mixture of ethyl 3-[4-(5-{[4-(4,5-dimethylthiophen-2-yl)-1,3-thiazol-2-yl]carbamoyl}pyrazin-2-yl)piperazin-1-yl]propanoate (400 mg), (2R)-2-methylpyrrolidine (273 mg), a 36% aqueous formaldehyde solution (0.5 mL), and acetic acid (8 mL) was stirred at 60° C. for 1.5 hours. The reaction mixture was cooled to room temperature and concentrated under reduced pressure. To the residue was added a saturated aqueous sodium hydrogen carbonate solution, followed by extraction with ethyl acetate. The organic layer was dried over anhydrous magnesium sulfate and then concentrated under reduced pressure. The residue was purified by basic silica gel column chromatography (hexane-ethyl acetate).

To a mixture of the obtained compound (452 mg), ethanol (4 mL), and tetrahydrofuran (4 mL) was added a 1 M aqueous sodium hydroxide solution (4 mL), followed by stirring at 50° C. for 1 hour. The reaction mixture was cooled to room temperature, and 1 M hydrochloric acid (4 mL) and water were added thereto. The mixture was extracted from chloroform/isopropanol/tetrahydrofuran, and the organic layer was dried over anhydrous magnesium sulfate and then concentrated under reduced pressure. To a mixture of the obtained compound and tetrahydrofuran (20 mL) was added hydrogen chloride (4 M dioxane solution, 2 mL). The mixture was concentrated under reduced pressure, and to the residue was added diethyl ether (20 mL). The solid was collected by filtration to obtain 3-[4-(5-{[4-(4,5-dimethylthiophen-2-yl)-5-{[(2R)-2-methylpyrrolidin-1-yl]methyl}-1,3-thiazol-2-yl]carbamoyl}pyrazin-2-yl)piperazin-1-yl]propanoic acid trihydrochloride (440 mg) as a solid.

Example 7

To a mixture of N-(4-[4-ethoxy-3-(trifluoromethyl)phenyl]-5-{[(2R)-2-methylpyrrolidin-1-yl]methyl}-1,3-thiazol-2-yl)-5-[(2R)-2-methylpiperazin-1-yl]pyrazine-2-carboxamide trihydrochloride (300 mg) and N,N-dimethylformamide (5 mL) were added potassium carbonate (300 mg) and ethyl 3-bromopropanoate (0.25 mL), followed by stirring at 60° C. for 1.5 hours. Thereafter, to the reaction mixture were added potassium carbonate (300 mg) and ethyl 3-bromopropanoate (0.25 mL), followed by stirring at 60° C. for 1.5 hours. Again, to the reaction mixture were added potassium carbonate (300 mg) and ethyl 3-bromopropanoate (0.25 mL), followed by stirring at 60° C. for 1 hour. The reaction mixture was cooled to room temperature, and water was added thereto, followed by extraction with ethyl acetate. The organic layer was washed with saturated brine, dried over anhydrous magnesium sulfate, and then concentrated under reduced pressure. The residue was purified by basic silica gel column chromatography (hexane-ethyl acetate).

To a mixture of the obtained compound (151 mg), tetrahydrofuran (2 mL), and ethanol (2 mL) was added a 1 M aqueous sodium hydroxide solution (1 mL), followed by stirring at 50° C. for 30 minutes. The reaction mixture was cooled to room temperature, and 1 M hydrochloric acid (1 mL) and water (15 mL) were added thereto, followed by extracted with chloroform/isopropanol. The organic layer was dried over anhydrous magnesium sulfate and then concentrated under reduced pressure. To a mixture of the obtained compound and tetrahydrofuran (10 mL) was added hydrogen chloride (4 M dioxane solution, 2 mL). The reaction mixture was concentrated under reduced pressure, and to the residue was added diethyl ether. The solid was collected by filtration to obtain 3-[(3R)-4-{5-[(4-[4-ethoxy-3-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]propanoic acid trihydrochloride (142 mg) as a solid.

Example 8

To a mixture of N-(4-[4-ethoxy-3-(trifluoromethyl)phenyl]-5-{[(2R)-2-methylpyrrolidin-1-yl]methyl}-1,3-thiazol-2-yl)-5-[(2R)-2-methylpiperazin-1-yl]pyrazine-2-carboxamide trihydrochloride (381 mg) and N,N-dimethylformamide (8 mL) was added potassium carbonate (390 mg), followed by stirring at room temperature for 10 minutes. To the reaction mixture was added ethyl bromoacetate (0.09 mL), followed by stirring at room temperature for 1.5 hours. To the reaction mixture was added ethyl bromoacetate (0.09 mL), followed by stirring at room temperature for 30 minutes. To the reaction mixture was added water, followed by extraction with ethyl acetate. The organic layer was washed with saturated brine, dried over anhydrous magnesium sulfate, and then concentrated under reduced pressure. The residue was purified by basic silica gel column chromatography (hexane-ethyl acetate).

To a mixture of the obtained compound (211 mg), tetrahydrofuran (3 mL), and ethanol (3 mL) was added a 1 M aqueous sodium hydroxide solution (1.5 mL), followed by stirring at 50° C. for 30 minutes. The reaction mixture was cooled to room temperature, and 1 M hydrochloric acid (1.5 mL) and water (15 mL) were added thereto, followed by extraction with chloroform/isopropanol. The organic layer was dried over anhydrous magnesium sulfate and then concentrated under reduced pressure. The residue was mixed with tetrahydrofuran (10 mL), and hydrogen chloride (4 M dioxane solution, 2 mL) was added thereto. The mixture was concentrated under reduced pressure, and to the residue was added diethyl ether. The solid was collected by filtration to obtain [(3R)-4-{5-[(4-[4-ethoxy-3-(trifluoromethyl)phenyl]-5-{[(2R)-2-methylpyrrolidin-1-yl]methyl}-1, 3-thiazol-2-yl)carbamoyl]pyrazin-2-yl}-3-methylpiperazin-1-yl]acetic acid trihydrochloride (185 mg).

Example 9

To a mixture of 5-[(diethylamino)methyl]-4-[3-fluoro-5-(trifluoromethyl)phenyl]-1,3-thiazol-2-amine (820 mg), triethylamine (2 mL), and cyclopentylmethyl ether (16 mL) was added 5-chloropyrazine-2-carbonylchloride (590 mg), followed by stirring at room temperature for 20 hours. To the reaction mixture was added water (50 mL), followed by extraction with chloroform. The organic layer was dried over anhydrous magnesium sulfate and then concentrated under reduced pressure. The residue was purified by silica gel column chromatography (hexane-ethyl acetate) to obtain a solid (1.0 g). To a mixture of the obtained compound (200 mg) and N-methylpyrrolidone (4 mL) were added ethyl 3-[(2R)-2-methylpiperazin-1-yl]propanoate dihydrochloride (168 mg) and N,N-diisopropylethylamine (0.5 mL), followed by stirring at 80° C. for 2 hours. The reaction mixture was cooled to room temperature, and water and ethyl acetate were added thereto. The organic layer was separated, washed with water and saturated brine, dried over anhydrous magnesium sulfate, and then concentrated under reduced pressure. The obtained compound was purified by silica gel column chromatography (hexane-ethyl acetate).

To a mixture of the obtained compound (249 mg), ethanol (4 mL), and tetrahydrofuran (4 mL) was added a 1 M aqueous sodium hydroxide solution (2 mL), followed by stirring at 50° C. for 30 minutes. The reaction mixture was cooled to room temperature, and 1 M hydrochloric acid (2 mL) and water (20 mL) were added thereto. The mixture was extracted with chloroform/isopropanol, and the organic layer was dried over anhydrous magnesium sulfate and then concentrated under reduced pressure. The residue was mixed with tetrahydrofuran (10 mL), and hydrogen chloride (4 M dioxane solution, 2 mL) was added thereto. The mixture was concentrated under reduced pressure, and to the residue was added diethyl ether. The solid was collected by filtration to obtain 3-{(2R)-4-[5-({5-[(diethylamino)methyl]-4-[3-fluoro-5-(trifluoromethyl)phenyl]-1,3-thiazol-2-yl}carbamoyl)pyrazin-2-yl]-2-methylpiperazin-1-yl}propanoic acid dihydrochloride (251 mg) as a solid.

Example 144

3-[(2S)-4-(5-{[4-(4-Chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid (500 mg) and maleic acid (148 mg) were dissolved in 2-butanone (0.5 mL) and dimethylsulfoxide (0.5 mL) under stirring at 60° C. To the solution was added 2-butanone (4.0 mL), followed by stirring at 60° C. for 30 minutes. Thereafter, the mixture was left to be slowly cooled to room temperature and stirred at room temperature for 16 hours. The precipitated solid was collected by filtration and dried under reduced pressure to obtain 3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid dimalate (378 mg) as a white crystal.

The crystals obtained in the present Examples have peaks of powder X-ray diffraction at $2\theta$ (°) 5.7, 6.6, 10.5, 12.0, 13.3, 15.8, 16.6, 17.3, 19.0, and 26.2.

The compounds of Preparation Examples and Examples shown in Tables below were produced in the same manner as the methods in Preparation Examples or Examples as described above.

TABLE 5

| PEx | Structure |
| --- | --- |
| 1 | (structure: 5-[((2S)-2-methylpyrrolidin-1-yl)methyl]-4-[3-fluoro-5-(trifluoromethyl)phenyl]-1,3-thiazol-2-yl N-(5-chloropyrazine-2-carbonyl)amide) |
| 2 | (structure: 5-[((2S)-2-methylpyrrolidin-1-yl)methyl]-4-[4-(trifluoromethyl)thiophen-2-yl]-1,3-thiazol-2-yl N-(5-chloropyrazine-2-carbonyl)amide) |
| 3 | (structure: 4-(4-chlorothiophen-2-yl)-1,3-thiazol-2-yl N-(5-chloropyrazine-2-carbonyl)amide) |
| 4 | (structure: 5-trifluoromethyl-6-methoxy-pyridine-3-carboxylic acid N-methoxy-N-methylamide) |
| 5 | (structure: 5-[((2S)-2-methylpyrrolidin-1-yl)methyl]-4-[3-fluoro-5-(trifluoromethyl)phenyl]-1,3-thiazol-2-amine) |

TABLE 6
| PEx | Structure |
|---|---|
| 6 | 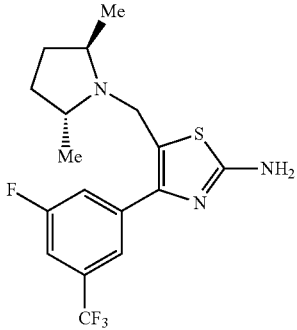 [SMILES: C[C@@H]1CC[C@@H](C)N1Cc1sc(N)nc1-c1cc(F)cc(C(F)(F)F)c1] |
| 7 | 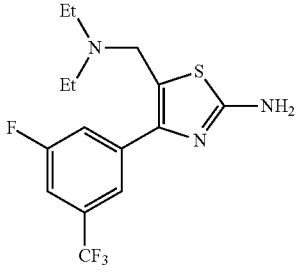 |
| 8 | 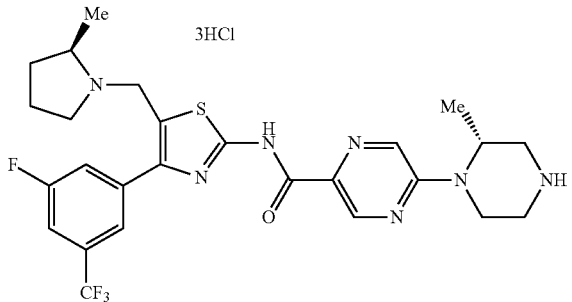 [SMILES: C[C@@H]1CCCN1Cc1sc(NC(=O)c2cnc(N3CCNC[C@H]3C)cn2)nc1-c1cc(F)cc(C(F)(F)F)c1] |
| 9 | 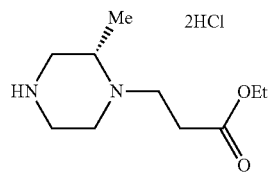 |
| 10 | 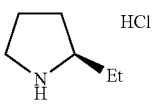 |

TABLE 7

| PEx | Structure |
|---|---|
| 11 | 5-((diethylamino)methyl)-4-(3-fluoro-5-(trifluoromethyl)phenyl)thiazol-2-yl acetamide |
| 12 | 4-(3-chloro-5-(trifluoromethyl)phenyl)-5-(((S)-2-methylpyrrolidin-1-yl)methyl)thiazol-2-yl acetamide |
| 13 | (2-acetamido-4-(3-fluoro-5-(trifluoromethyl)phenyl)thiazol-5-yl)methyl acetate |
| 14 | (2-(5-(4-(3-ethoxy-3-oxopropyl)-3-methylpiperazin-1-yl)pyrazine-2-carboxamido)-4-(4-chlorothiophen-2-yl)thiazol-5-yl)methyl acetate |
| 15 | (2-acetamido-4-(4-methoxy-3-(trifluoromethyl)phenyl)thiazol-5-yl)methyl acetate |

TABLE 8
| PEx | Structure |
|---|---|
| 16 | 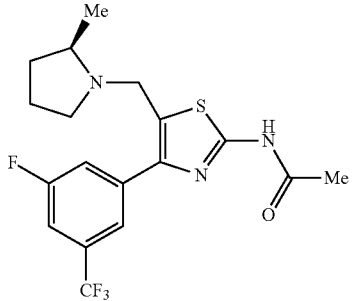 |
| 17 | 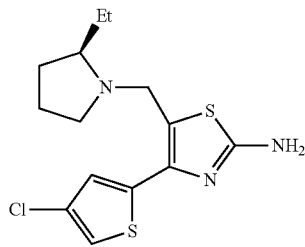 |
| 18 | 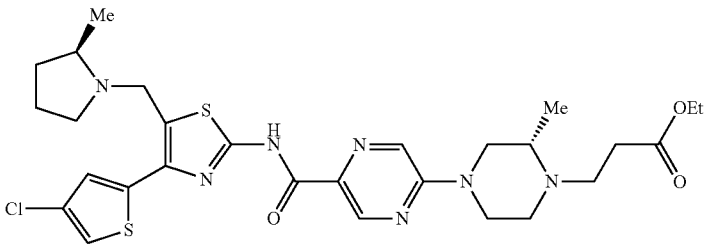 [SMILES: CCOC(=O)CCN1CCN(c2cnc(C(=O)Nc3nc(-c4cc(Cl)cs4)c(CN4CCC[C@H]4C)s3)cn2)C[C@@H]1C] |
| 19 | 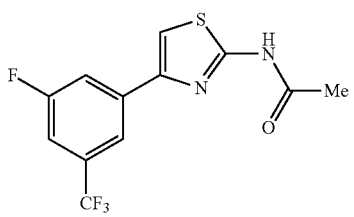 [SMILES: CC(=O)Nc1nc(-c2cc(F)cc(C(F)(F)F)c2)cs1] |
| 20 | 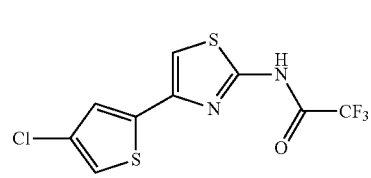 [SMILES: O=C(Nc1nc(-c2cc(Cl)cs2)cs1)C(F)(F)F] |

TABLE 9
| PEx | Structure |
|---|---|
| 21 | 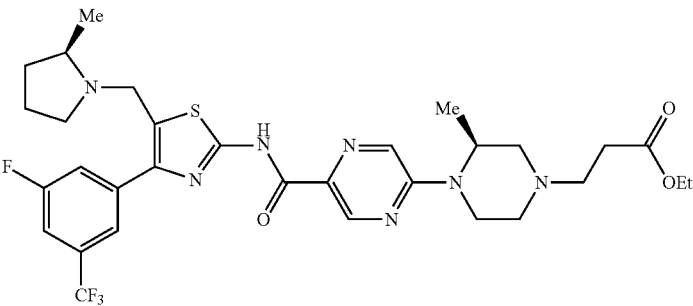 [SMILES: CCOC(=O)CCN1CCN(c2cnc(C(=O)Nc3nc(-c4cc(F)cc(C(F)(F)F)c4)c(CN4CCC[C@H]4C)s3)cn2)[C@@H](C)C1] |
| 22 | 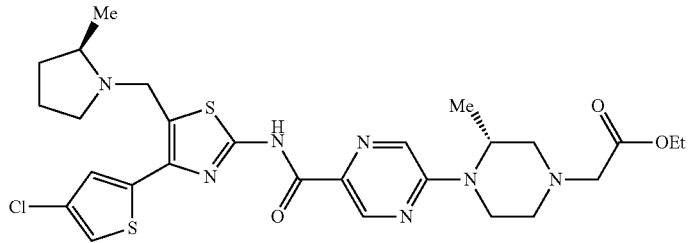 [SMILES: CCOC(=O)CN1CCN(c2cnc(C(=O)Nc3nc(-c4cc(Cl)cs4)c(CN4CCC[C@H]4C)s3)cn2)[C@H](C)C1] |
| 23 | 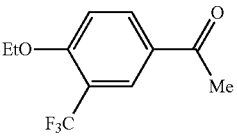 |
| 24 | 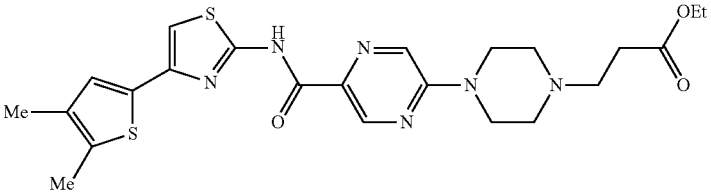 [SMILES: CCOC(=O)CCN1CCN(c2cnc(C(=O)Nc3nc(-c4cc(C)c(C)s4)cs3)cn2)CC1] |
| 25 | 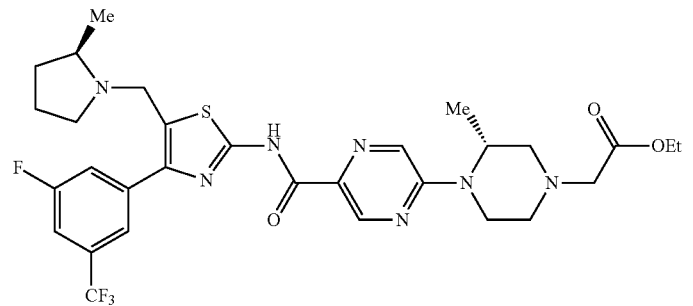 [SMILES: CCOC(=O)CN1CCN(c2cnc(C(=O)Nc3nc(-c4cc(F)cc(C(F)(F)F)c4)c(CN4CCC[C@H]4C)s3)cn2)[C@H](C)C1] |

TABLE 10

| PEx | Structure |
|---|---|
| 26 | 4-nPrO-3-CF₃-phenyl methyl ketone |
| 27 | (2S)-1-Boc-2-ethylpyrrolidine |
| 28 | ethyl 2-[(3S)-4-Boc-3-methylpiperazin-1-yl]acetate |
| 29 | ethyl 3-[(2S)-4-[5-[[4-(4-chlorothiophen-2-yl)thiazol-2-yl]carbamoyl]pyrazin-2-yl]-2-methylpiperazin-1-yl]propanoate |
| 30 | 4-[3-fluoro-5-(trifluoromethyl)phenyl]thiazol-2-amine |
| 31 | 1-[4-(trifluoromethyl)thiophen-2-yl]ethanone |
| 32 | 1-[6-methoxy-5-(trifluoromethyl)pyridin-3-yl]ethanone |

TABLE 11

| PEx | Structure |
|---|---|
| 33 | 3,5-dichloro-4-methoxyacetophenone |
| 34 | 5-methoxy-4-(trifluoromethyl)nicotinic acid (with OH, C=O, CF₃, OMe, pyridine N) |
| 35 | ethyl 6-methoxy-5-(trifluoromethyl)nicotinate (EtO-C(=O)-, CF₃, OMe, pyridine) |
| 36 | 5-bromo-3-(trifluoromethyl)-2-methoxypyridine |
| 37 | 1-(4-isopropoxy-3-(trifluoromethyl)phenyl)ethanone |
| 38 | 1-(4-cyclopropyl-3-(trifluoromethyl)phenyl)ethanone |
| 39 | 1-(4-cyclopropylthiophen-2-yl)ethanone |
| 40 | 1-(3-bromo-5-(trifluoromethyl)phenyl)ethanone |

TABLE 12

| PEx | Structure |
|---|---|
| 41 | 1-(3-fluoro-4-methoxy-5-(trifluoromethyl)phenyl)ethanone |
| 42 | 4-(4-(difluoromethoxy)-3-(trifluoromethyl)phenyl)thiazol-2-amine |
| 43 | N-(4-(4-ethoxy-3-(trifluoromethyl)phenyl)-5-(((2S)-2-methylpyrrolidin-1-yl)methyl)thiazol-2-yl)-5-((2S)-2-methylpiperazin-1-yl)pyrazine-2-carboxamide · 3HCl |

TABLE 12-continued
| PEx | Structure |
|---|---|
| 44 | 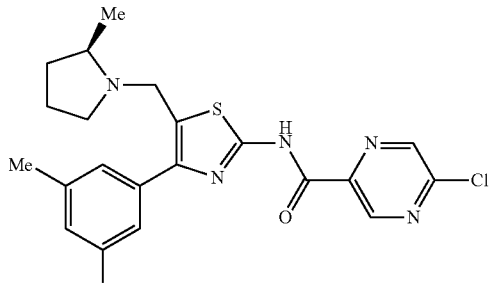 |
| 45 | 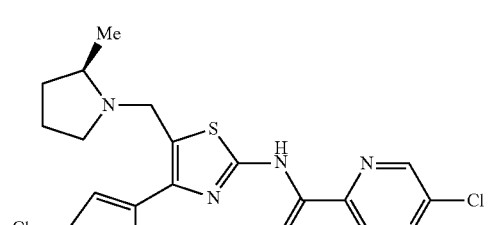 |
| 46 | 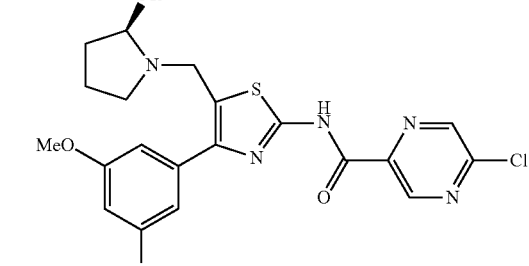 |
TABLE 13
| PEx | Structure |
|---|---|
| 47 | 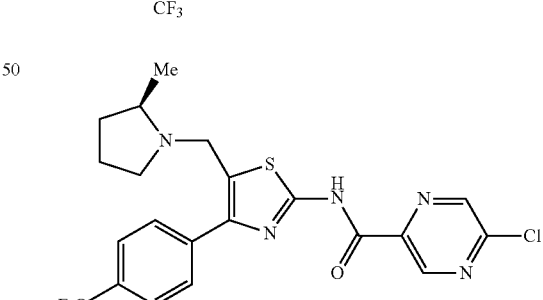 |
| 48 | 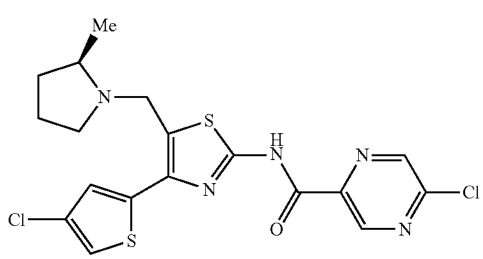 [SMILES: C[C@@H]1CCCN1Cc1sc(NC(=O)c2cnc(Cl)cn2)nc1-c1cc(Cl)cs1] |
| 49 | |
| 50 | |

TABLE 14
| PEx | Structure |
|---|---|
| 51 | 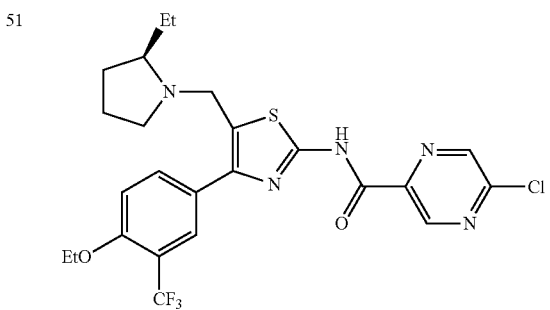 |
| 52 | 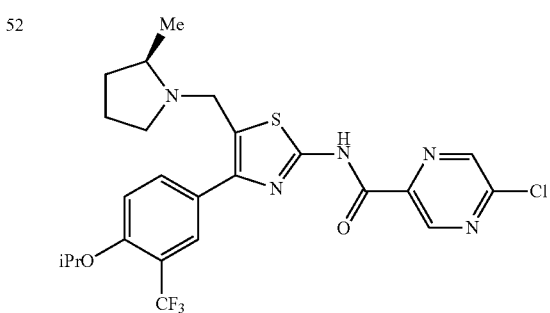 |
| 53 | 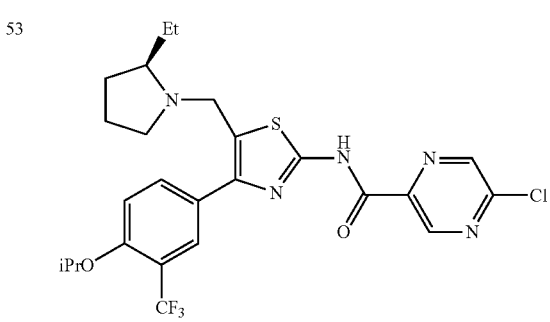 |
| 54 | 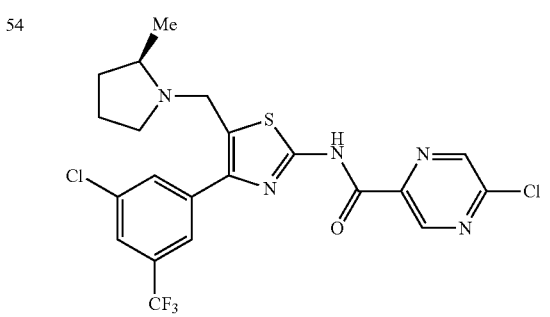 |
TABLE 15
| PEx | Structure |
|---|---|
| 55 | 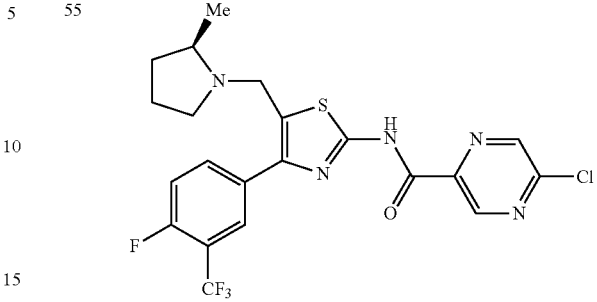 |
| 56 | 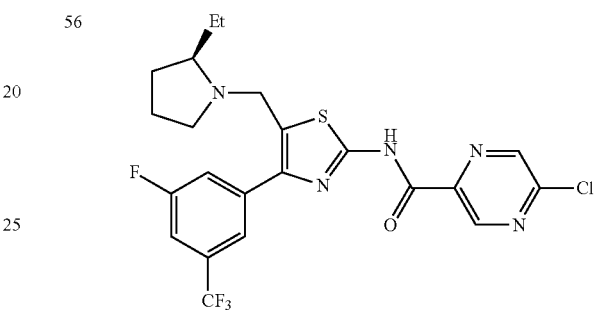 |
| 57 | 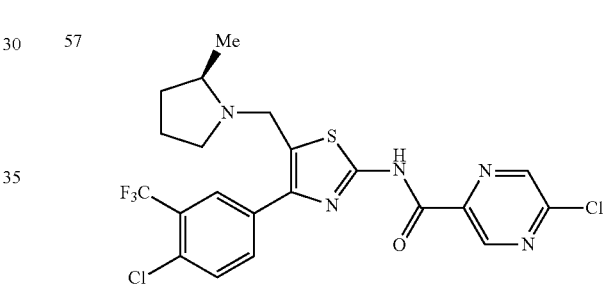 |
| 58 | 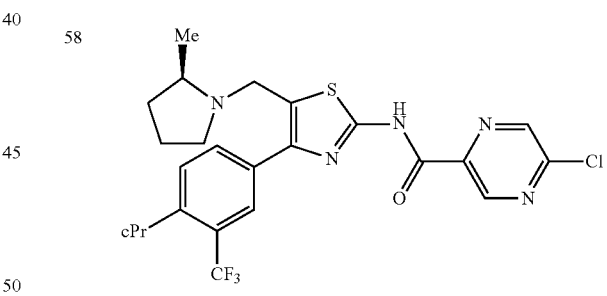 |
TABLE 16
| PEx | Structure |
|---|---|
| 59 | 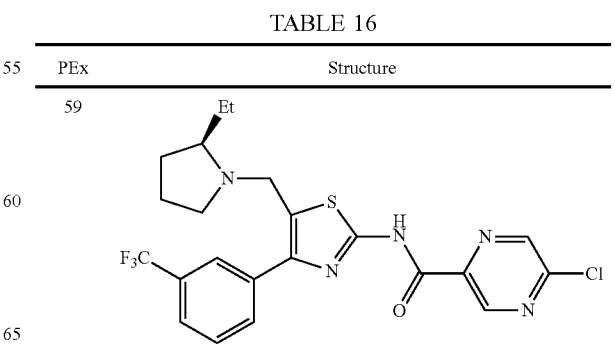 |

TABLE 16-continued

| PEx | Structure |
|---|---|
| 60 | (2-Me-pyrrolidinyl)methyl-thiazole with 3-cPr-5-CF3-phenyl, NH-C(O)-5-chloropyrazine |
| 61 | (2-Et-pyrrolidinyl)methyl-thiazole with 3-cPr-5-CF3-phenyl, NH-C(O)-5-chloropyrazine |
| 62 | (2-Me-pyrrolidinyl)methyl-thiazole with 3-Me-5-CF3-phenyl, NH-C(O)-5-chloropyrazine |

TABLE 17

| PEx | Structure |
|---|---|
| 63 | (2-nPr-pyrrolidinyl)methyl-thiazole with 4-MeO-3-CF3-phenyl, NH-C(O)-5-chloropyrazine |
| 64 | (2-Me-pyrrolidinyl)methyl-thiazole with 3-F-4-MeO-5-CF3-phenyl, NH-C(O)-5-chloropyrazine |
| 65 | (2-Me-pyrrolidinyl)methyl-thiazole with 3-F-4-MeO-5-Cl-phenyl, NH-C(O)-5-chloropyrazine |
| 66 | (2-Me-pyrrolidinyl)methyl-thiazole with 4-OCHF2-3-CF3-phenyl, NH-C(O)-5-chloropyrazine |

TABLE 18

| PEx | Structure |
|---|---|
| 67 | (2-Me-pyrrolidinyl)methyl-thiazole with 4-nPrO-3-CF3-phenyl, NH-C(O)-5-chloropyrazine |
| 68 | (2-Et-pyrrolidinyl)methyl-thiazole with 4-chlorothiophen-2-yl, NH-C(O)-5-chloropyrazine |

TABLE 18-continued
| PEx | Structure |
|---|---|
| 69 | 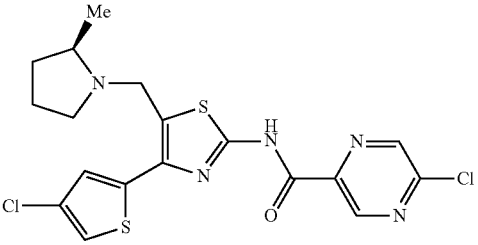 |
| 70 | 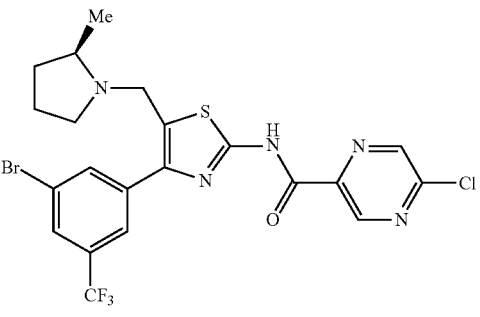 [SMILES: C[C@@H]1CCCN1Cc1sc(NC(=O)c2cnc(Cl)cn2)nc1-c1cc(Cl)cc(C(F)(F)F)c1] |
| 71 | 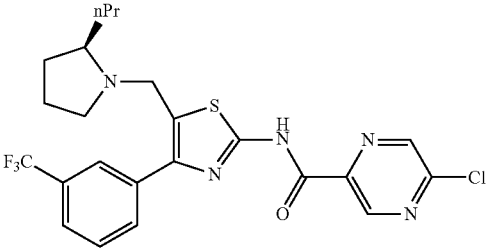 [SMILES: CC[C@@H]1CCCN1Cc1sc(NC(=O)c2cnc(Cl)cn2)nc1-c1cccc(C(F)(F)F)c1] |
TABLE 19
| PEx | Structure |
|---|---|
| 72 | 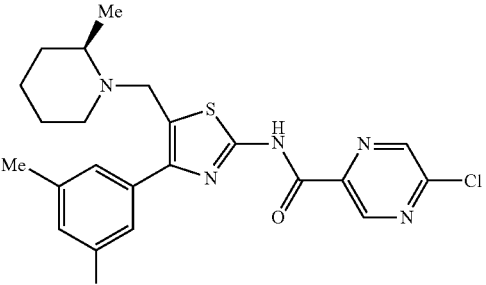 |
| 73 | 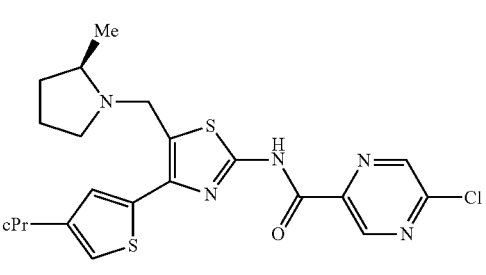 |
TABLE 19-continued
| PEx | Structure |
|---|---|
| 74 | 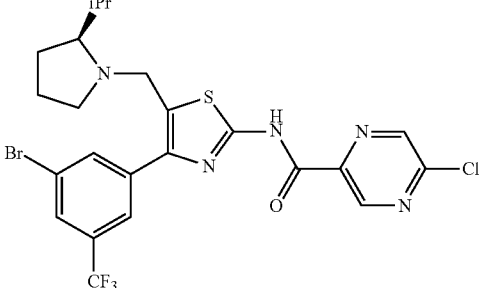 |
| 75 | 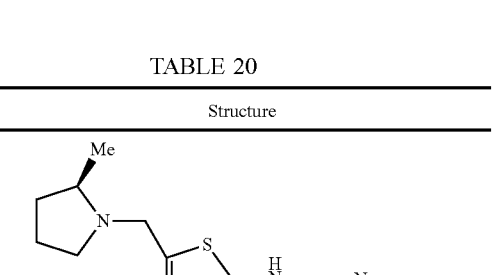 |
| 76 | 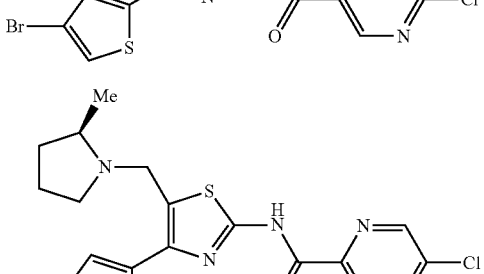 |
TABLE 20
| PEx | Structure |
|---|---|
| 77 | 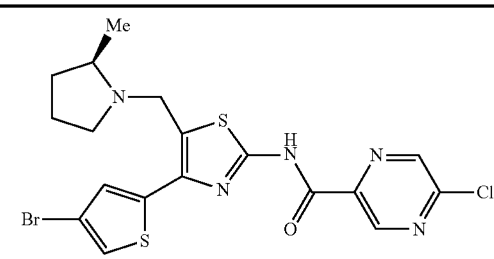 |
| 78 | 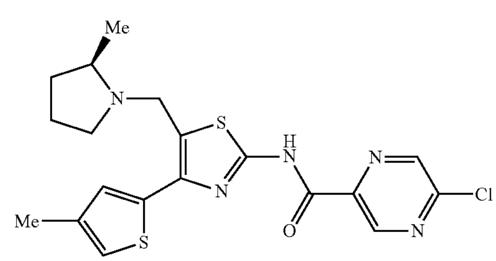 [SMILES: Cc1csc(-c2nc(NC(=O)c3cnc(Cl)cn3)sc2CN2CCC[C@H]2C)c1] |

TABLE 20-continued
| PEx | Structure |
|---|---|
| 79 | 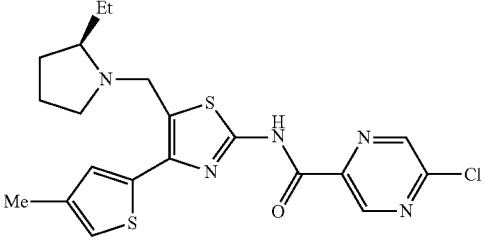 |
| 80 | 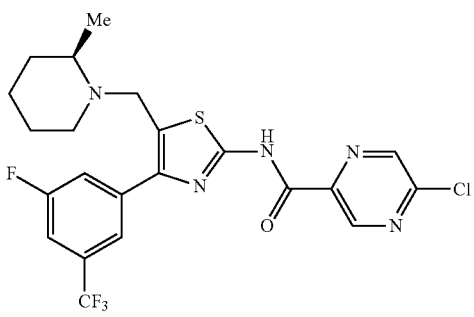 [SMILES: C[C@@H]1CCCCN1Cc1sc(NC(=O)c2cnc(Cl)cn2)nc1-c1cc(F)cc(C(F)(F)F)c1] |
| 81 | 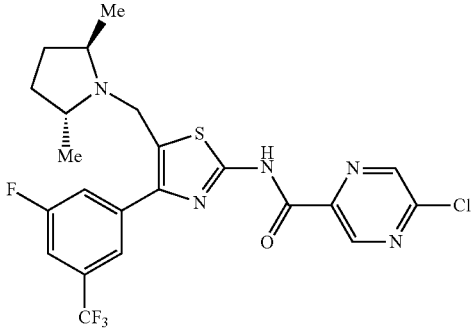 [SMILES: C[C@@H]1CC[C@@H](C)N1Cc1sc(NC(=O)c2cnc(Cl)cn2)nc1-c1cc(F)cc(C(F)(F)F)c1] |
TABLE 21
| PEx | Structure |
|---|---|
| 82 | 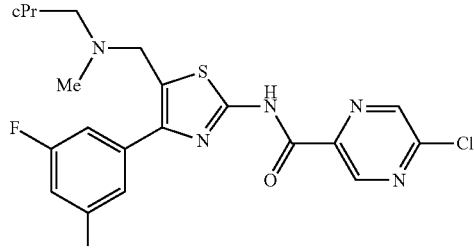 |
| 83 | 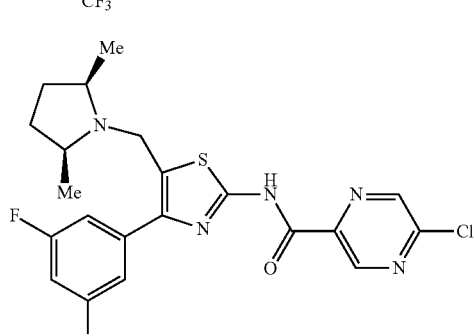 |
TABLE 21-continued
| PEx | Structure |
|---|---|
| 84 | 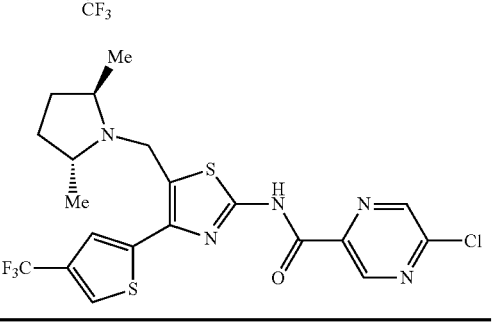 |
| 85 | 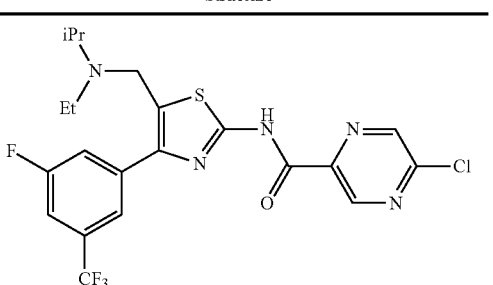 |
| 86 | 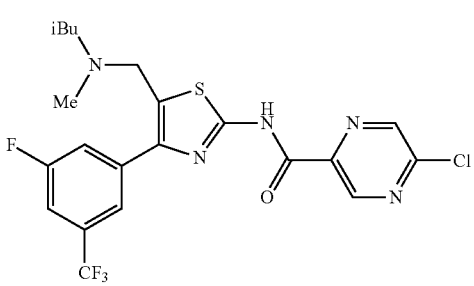 |
TABLE 22
| PEx | Structure |
|---|---|
| 87 | 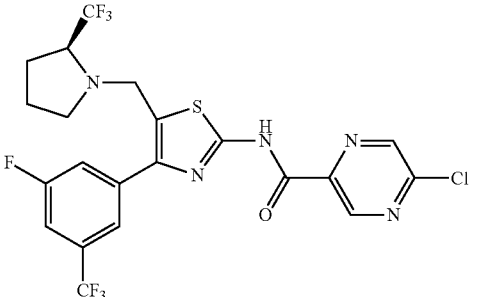 |
| 88 | 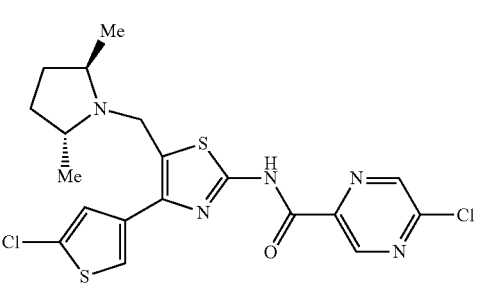 [SMILES: C[C@@H]1CC[C@@H](C)N1Cc1sc(NC(=O)c2cnc(Cl)cn2)nc1-c1csc(Cl)c1] |

TABLE 22-continued

| PEx | Structure |
|---|---|
| 89 | (structure: 4-(6-methoxy-5-(trifluoromethyl)pyridin-3-yl)-5-(((S)-2-methylpyrrolidin-1-yl)methyl)thiazol-2-yl 5-chloropyrazine-2-carboxamide) |
| 90 | (structure: 4-(4-methoxy-3-(trifluoromethyl)phenyl)thiazol-2-yl 5-chloropyrazine-2-carboxamide) |

TABLE 23

| PEx | Structure |
|---|---|
| 91 | (structure: 4-(3-methyl-5-(trifluoromethoxy)phenyl)-5-(((S)-2-methylpyrrolidin-1-yl)methyl)thiazol-2-amine) |
| 92 | (structure: 4-(4-chlorothiophen-2-yl)-5-(((S)-2-methylpyrrolidin-1-yl)methyl)thiazol-2-amine) |
| 93 | (structure: 4-(3-methoxy-5-(trifluoromethyl)phenyl)-5-(((S)-2-methylpyrrolidin-1-yl)methyl)thiazol-2-amine) |

TABLE 23-continued

| PEx | Structure |
|---|---|
| 94 | (structure: 4-(3-chloro-5-(trifluoromethyl)phenyl)-5-(((S)-2-methylpyrrolidin-1-yl)methyl)thiazol-2-amine) |

TABLE 24

| PEx | Structure |
|---|---|
| 95 | (structure: 4-(4-fluoro-3-(trifluoromethyl)phenyl)-5-(((S)-2-methylpyrrolidin-1-yl)methyl)thiazol-2-amine) |
| 96 | (structure: 5-(((S)-2-ethylpyrrolidin-1-yl)methyl)-4-(3-fluoro-5-(trifluoromethyl)phenyl)thiazol-2-amine) |
| 97 | (structure: 4-(4-methoxy-3-(trifluoromethyl)phenyl)-5-(((S)-2-propylpyrrolidin-1-yl)methyl)thiazol-2-amine) |

TABLE 24-continued
| PEx | Structure |
|---|---|
| 98 | 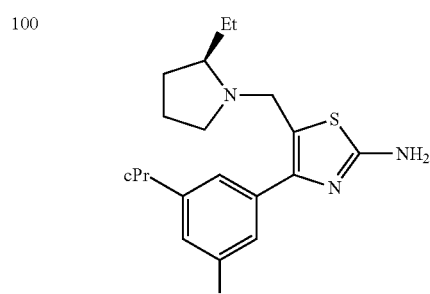 |
TABLE 25
| PEx | Structure |
|---|---|
| 99 | 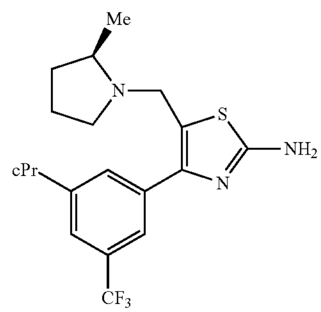 |
| 100 | 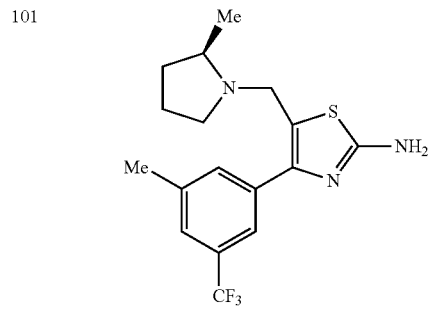 |
| 101 | 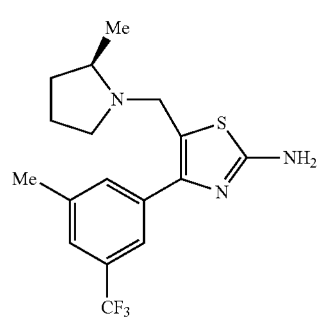 [SMILES: Cc1cc(-c2nc(N)sc2CN2CCC[C@H]2C)cc(C(F)(F)F)c1] |
TABLE 25-continued
| PEx | Structure |
|---|---|
| 102 | 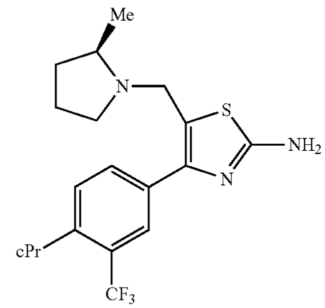 |
TABLE 26
| PEx | Structure |
|---|---|
| 103 | 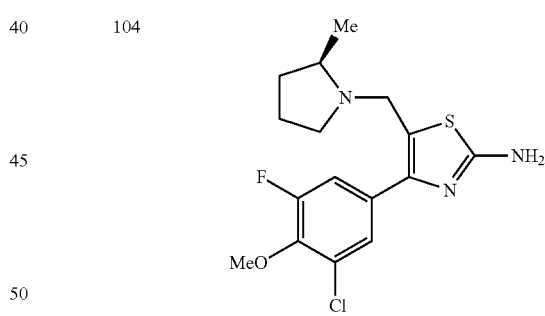 |
| 104 | 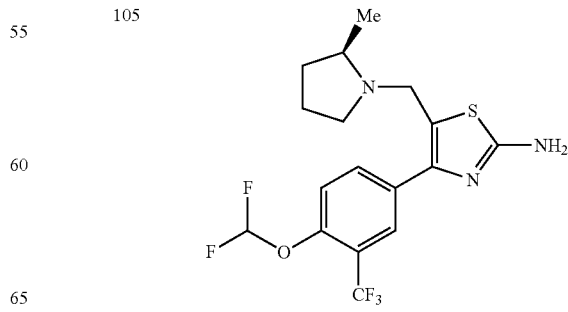 |
| 105 | 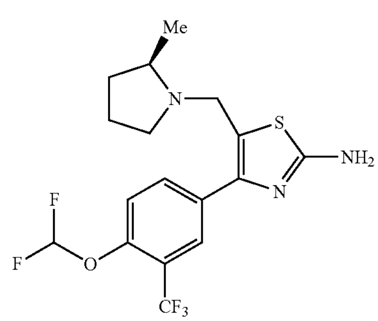 [SMILES: C[C@@H]1CCCN1Cc1sc(N)nc1-c1ccc(OC(F)F)c(C(F)(F)F)c1] |

TABLE 26-continued
| PEx | Structure |
|---|---|
| 106 | 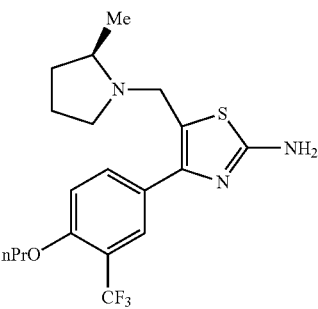 |
TABLE 27
| PEx | Structure |
|---|---|
| 107 | 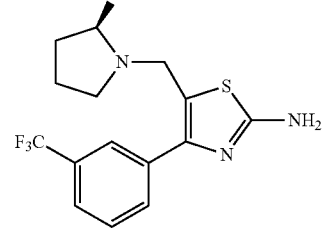 |
| 108 | 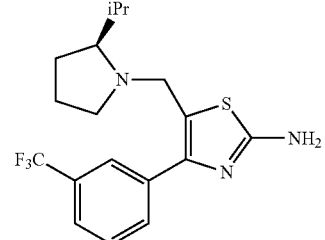 |
| 109 | 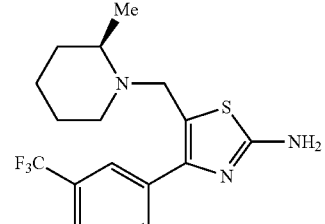 |
| 110 | 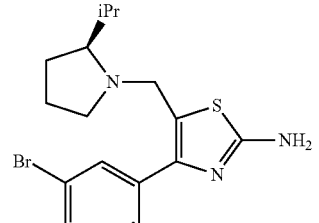 |
TABLE 27-continued
| PEx | Structure |
|---|---|
| 111 | 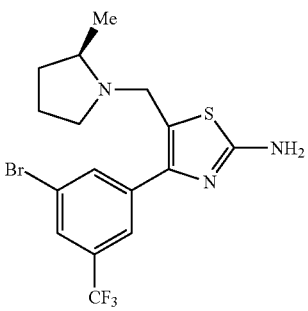 [SMILES: C[C@@H]1CCCN1Cc1sc(N)nc1-c1cc(Br)cc(C(F)(F)F)c1] |
TABLE 28
| PEx | Structure |
|---|---|
| 112 | 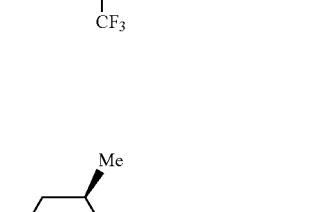 |
| 113 | 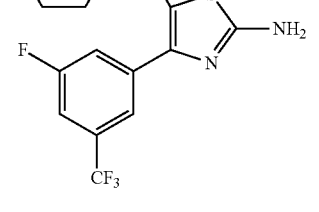 |
| 114 | 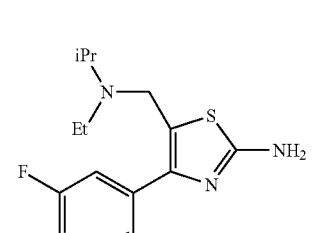 |

TABLE 28-continued
| PEx | Structure |
|---|---|
| 115 | 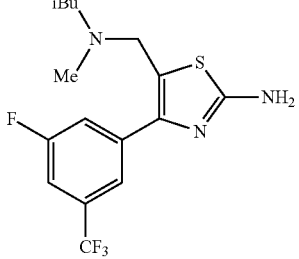 |
TABLE 29
| PEx | Structure |
|---|---|
| 116 | 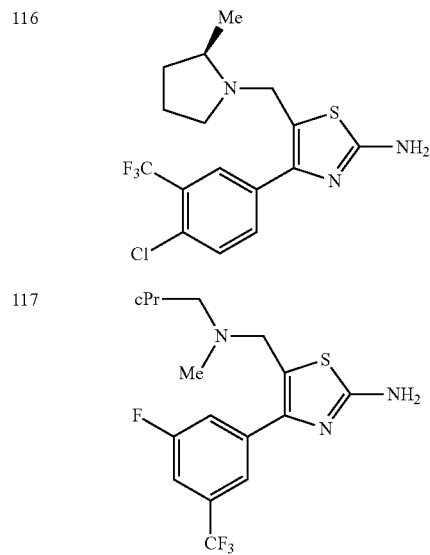 |
| 117 | 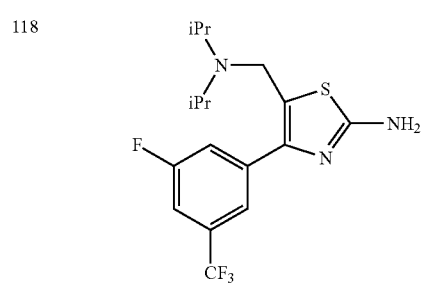 |
| 118 | 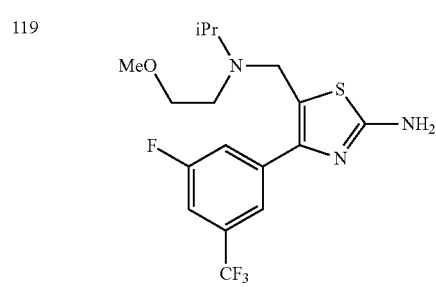 |
| 119 | 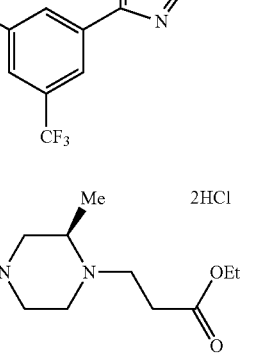 |
TABLE 29-continued
| PEx | Structure |
|---|---|
| 120 | 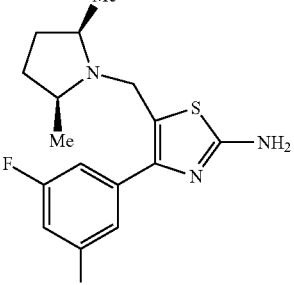 |
TABLE 30
| PEx | Structure |
|---|---|
| 121 | 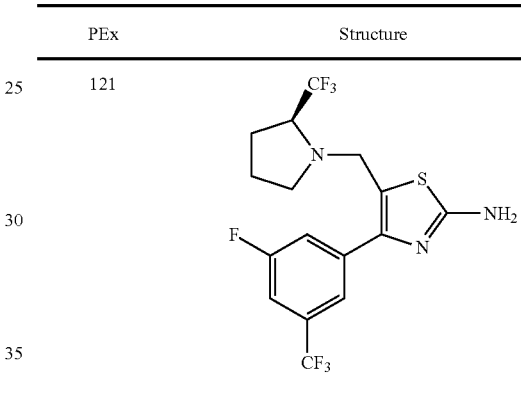 |
| 122 | 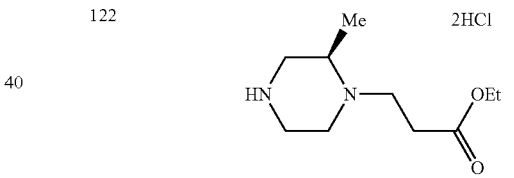 |
| 123 | 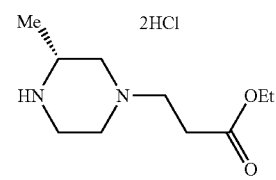 [SMILES: CCOC(=O)CCN1CCN[C@H](C)C1] |
| 124 | 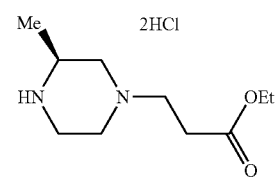 [SMILES: CCOC(=O)CCN1CCN[C@@H](C)C1] |
| 125 | 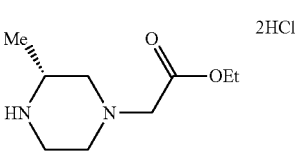 [SMILES: CCOC(=O)CN1CCN[C@H](C)C1] |

TABLE 30-continued

| PEx | Structure |
|---|---|
| 126 | (2-Me-pyrrolidinyl)CH2-thiazole-NHAc, 4-aryl = 3-Me-5-OCF3-phenyl |

TABLE 31

| PEx | Structure |
|---|---|
| 127 | (2-Me-pyrrolidinyl)CH2-thiazole-NHAc, 4-aryl = 4-Cl-thiophen-2-yl |
| 128 | (2-Me-pyrrolidinyl)CH2-thiazole-NHAc, 4-aryl = 3-MeO-5-CF3-phenyl |
| 129 | (2-Et-pyrrolidinyl)CH2-thiazole-NHAc, 4-aryl = 3-F-5-CF3-phenyl |
| 130 | (2-Et-pyrrolidinyl)CH2-thiazole-NHAc, 4-aryl = 3-CF3-phenyl |

TABLE 32

| PEx | Structure |
|---|---|
| 131 | (2-Me-pyrrolidinyl)CH2-thiazole-NHAc, 4-aryl = 3-cPr-5-CF3-phenyl |
| 132 | (2-Et-pyrrolidinyl)CH2-thiazole-NHAc, 4-aryl = 3-cPr-5-CF3-phenyl |
| 133 | (2-Me-pyrrolidinyl)CH2-thiazole-NHAc, 4-aryl = 3-Me-5-CF3-phenyl |
| 134 | (2-nPr-pyrrolidinyl)CH2-thiazole-NHAc, 4-aryl = 4-MeO-3-CF3-phenyl |

TABLE 33
| PEx | Structure |
|---|---|
| 135 | 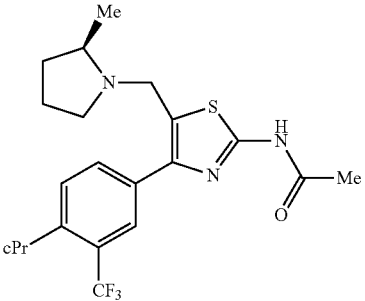 |
| 136 | 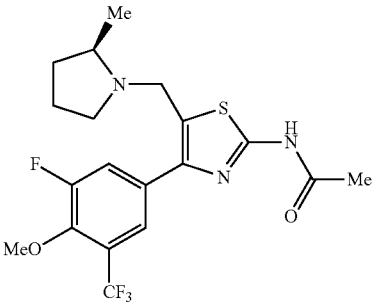 [SMILES: COc1c(F)cc(-c2nc(NC(C)=O)sc2CN2CCC[C@H]2C)cc1C(F)(F)F] |
| 137 | 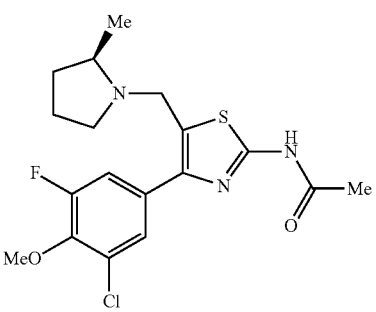 [SMILES: COc1c(F)cc(-c2nc(NC(C)=O)sc2CN2CCC[C@H]2C)cc1Cl] |
| 138 | 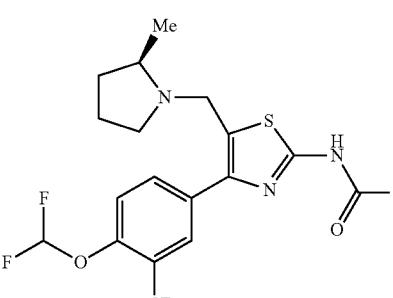 |
TABLE 34
| PEx | Structure |
|---|---|
| 139 | 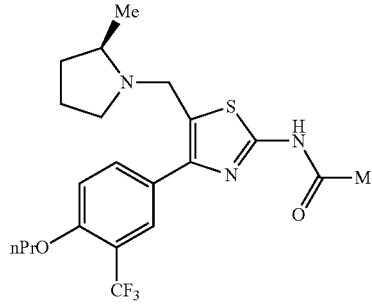 |
| 140 | 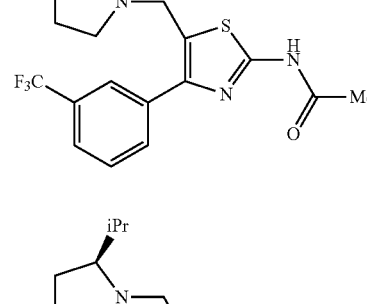 |
| 141 | 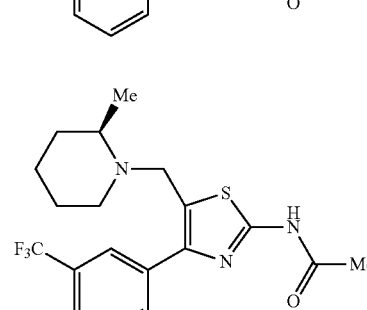 |
| 142 | 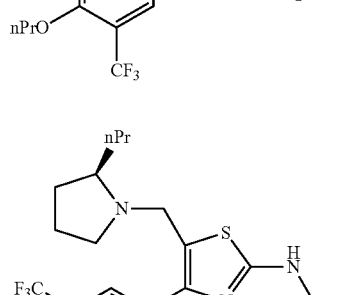 |
| 143 | 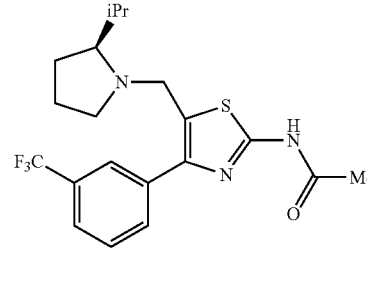 |

TABLE 35
| PEx | Structure |
|---|---|
| 144 | 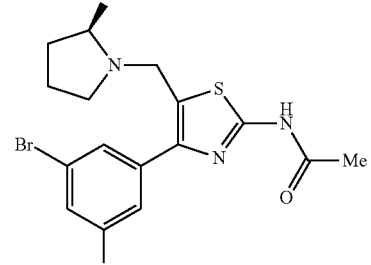 |
| 145 | 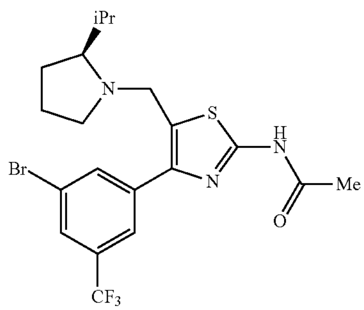 [SMILES: CC(=O)Nc1nc(-c2cc(Br)cc(C(F)(F)F)c2)c(CN2CCC[C@H]2C(C)C)s1] |
TABLE 35-continued
| PEx | Structure |
|---|---|
| 146 | 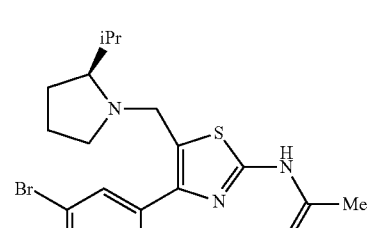 |
| 147 | 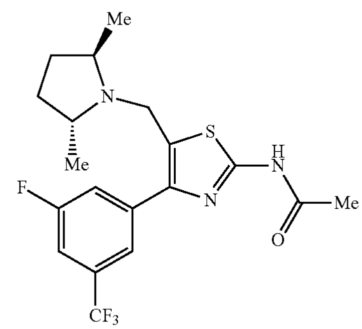 [SMILES: CC(=O)Nc1nc(-c2cc(F)cc(C(F)(F)F)c2)c(CN2[C@H](C)CC[C@H]2C)s1] |
TABLE 36
| PEx | Structure |
|---|---|
| 148 | 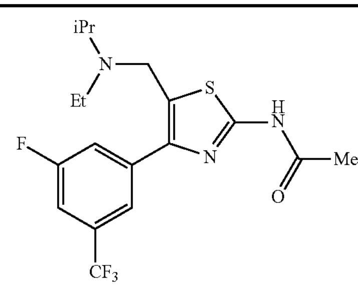 |
| 149 | 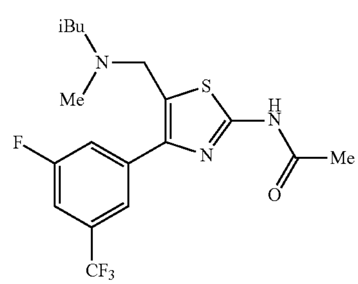 |
| 150 | 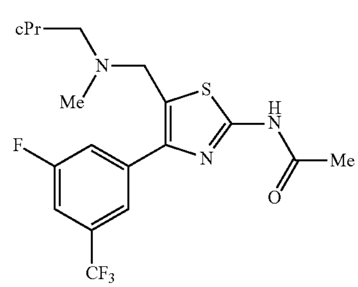 |

TABLE 36-continued

| PEx | Structure |
|---|---|
| 151 | (structure) |
| 152 | (structure) |

TABLE 37

| PEx | Structure |
|---|---|
| 153 | (structure) |
| 154 | (structure) |

TABLE 37-continued

| PEx | Structure |
|---|---|
| 155 | (structure) |
| 156 | (structure) |
| 157 | (structure) |

TABLE 38

| PEx | Structure |
|---|---|
| 158 | (5-chlorothiophen-2-yl thiazole with AcOCH2 and NHAc) |
| 159 | (3-MeO-5-CF3-phenyl thiazole with AcOCH2 and NHAc) |
| 160 | (4-Cl-3-CF3-phenyl thiazole with AcOCH2 and NHAc) |
| 161 | (3-CF3-phenyl thiazole with AcOCH2 and NHAc) |
| 162 | (3-cPr-5-CF3-phenyl thiazole with AcOCH2 and NHAc) |
| 163 | (3-Me-5-CF3-phenyl thiazole with AcOCH2 and NHAc) |

TABLE 39

| PEx | Structure |
|---|---|
| 164 | (4-cPr-3-CF3-phenyl thiazole with AcOCH2 and NHAc) |
| 165 | (3-F-4-MeO-5-CF3-phenyl thiazole with AcOCH2 and NHAc) |
| 166 | (3-F-4-MeO-5-Cl-phenyl thiazole with AcOCH2 and NHAc) |
| 167 | (4-OCHF2-3-CF3-phenyl thiazole with AcOCH2 and NHAc) |
| 168 | (4-OnPr-3-CF3-phenyl thiazole with AcOCH2 and NHAc) |

TABLE 40

| PEx | Structure |
|---|---|
| 169 | 4-(3-bromo-5-(trifluoromethyl)phenyl)-2-acetamido-thiazol-5-yl)methyl acetate |
| 170 | 4-(3-chloro-5-(trifluoromethyl)phenyl)-2-acetamido-thiazol-5-yl)methyl acetate |
| 171 | ethyl 3-((S)-4-(5-((4-(4-chlorothiophen-2-yl)-5-(acetoxymethyl)thiazol-2-yl)carbamoyl)pyrazin-2-yl)-2-methylpiperazin-1-yl)propanoate |
| 172 | N-(4-(4-fluoro-3-(trifluoromethyl)phenyl)-5-(((S)-2-methylpyrrolidin-1-yl)methyl)thiazol-2-yl)acetamide |
| 173 | 4-(3,5-dichloro-4-methoxyphenyl)-5-(((S)-2-methylpyrrolidin-1-yl)methyl)thiazol-2-amine |

TABLE 41

| PEx | Structure |
|---|---|
| 174 | (2-methylpyrrolidin-1-yl)methyl-thiazol-2-amine with 4-ethoxy-3-trifluoromethylphenyl |
| 175 | (2-ethylpyrrolidin-1-yl)methyl-thiazol-2-amine with 4-ethoxy-3-trifluoromethylphenyl |
| 176 | (2-methylpyrrolidin-1-yl)methyl-thiazol-2-amine with 4-isopropoxy-3-trifluoromethylphenyl |
| 177 | (2-ethylpyrrolidin-1-yl)methyl-thiazol-2-amine with 4-isopropoxy-3-trifluoromethylphenyl |

TABLE 42

| PEx | Structure |
|---|---|
| 178 | (2-methylpyrrolidin-1-yl)methyl-thiazol-2-amine with 4-methylthiophen-2-yl |
| 179 | (2-ethylpyrrolidin-1-yl)methyl-thiazol-2-amine with 4-methylthiophen-2-yl |
| 180 | (2-methylpyrrolidin-1-yl)methyl-thiazol-2-amine with 5-chlorothiophen-3-yl |
| 181 | (2-methylpyrrolidin-1-yl)methyl-thiazol-2-amine with 4-cyclopropylthiophen-2-yl |
| 182 | (2-methylpyrrolidin-1-yl)methyl-thiazol-2-amine with 4-(trifluoromethyl)thiophen-2-yl |

TABLE 43

| PEx | Structure |
|---|---|
| 183 | (structure) |
| 184 | (structure) |
| 185 | (structure) |
| 186 | (structure) |
| 187 | (structure) |

TABLE 44

| PEx | Structure |
|---|---|
| 188 | (structure) |
| 189 | (structure) |
| 190 | (structure) |
| 191 | (structure) |
| 192 | (structure) |
| 193 | (structure) |

TABLE 45

| PEx | Structure |
|---|---|
| 194 | 3-MeO, 5-CF3-phenyl-thiazol-2-yl-NHAc |
| 195 | 4-F, 3-CF3-phenyl-thiazol-2-yl-NHAc |
| 196 | 3-CF3-phenyl-thiazol-2-yl-NHAc |
| 197 | 3-cPr, 5-CF3-phenyl-thiazol-2-yl-NHAc |
| 198 | 3-Me, 5-CF3-phenyl-thiazol-2-yl-NHAc |
| 199 | 4-cPr, 3-CF3-phenyl-thiazol-2-yl-NHAc |

TABLE 46

| PEx | Structure |
|---|---|
| 200 | 3-F, 4-MeO, 5-CF3-phenyl-thiazol-2-yl-NHAc |
| 201 | 3-F, 4-MeO, 5-Cl-phenyl-thiazol-2-yl-NHAc |
| 202 | 4-OCHF2, 3-CF3-phenyl-thiazol-2-yl-NHAc |
| 203 | 4-OnPr, 3-CF3-phenyl-thiazol-2-yl-NHAc |
| 204 | 3-Br, 5-CF3-phenyl-thiazol-2-yl-NHAc |
| 205 | 3,5-diCl, 4-MeO-phenyl-thiazol-2-yl-NHC(O)CF3 |

TABLE 47

| PEx | Structure |
|---|---|
| 206 | 3-CF3, 4-EtO-phenyl-thiazol-2-yl-NHC(O)CF3 |

TABLE 47-continued
| PEx | Structure |
|---|---|
| 207 | ![structure] |
| 208 | ![structure] |
| 209 | ![structure] |
TABLE 47-continued
| PEx | Structure |
|---|---|
| 210 | ![structure] |
| 211 | ![structure] |
| 212 | ![structure] |
TABLE 48
| PEx | Structure |
|---|---|
| 213 | ![structure] |
| 214 | 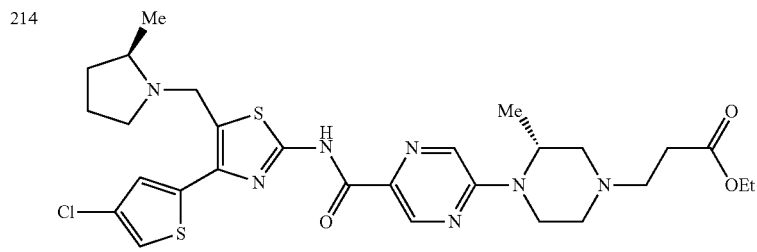 |
| 215 | 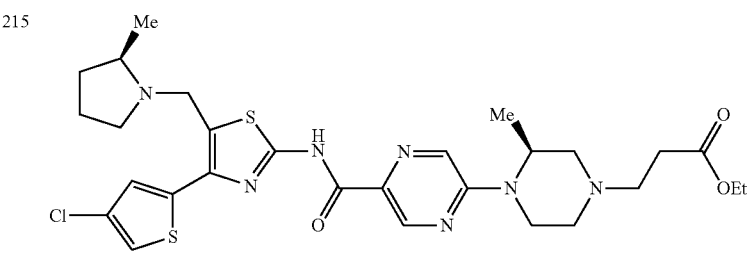 |

TABLE 48-continued
| PEx | Structure |
|---|---|
| 216 | 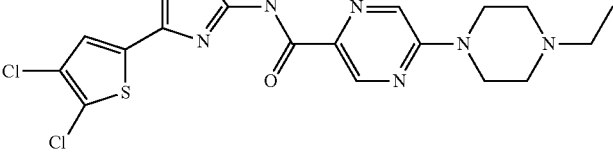 |
| 217 | 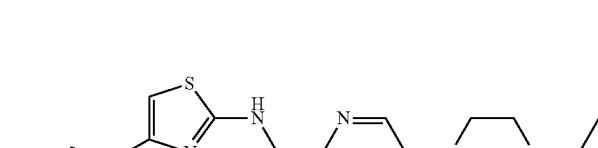 |
TABLE 49
| PEx | Structure |
|---|---|
| 218 | 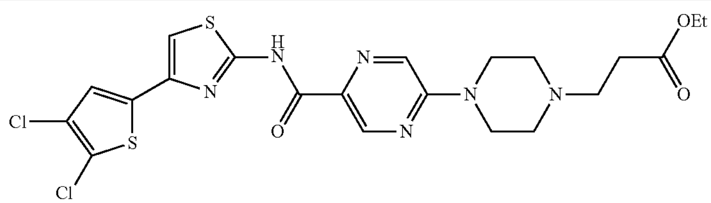 [SMILES: CCOC(=O)CCN1CCN(c2cnc(C(=O)Nc3nc(-c4cc(Cl)c(Cl)s4)cs3)cn2)CC1] |
| 219 | 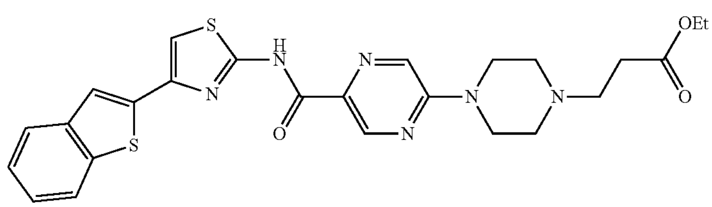 [SMILES: CCOC(=O)CCN1CCN(c2cnc(C(=O)Nc3nc(-c4cc5ccccc5s4)cs3)cn2)CC1] |
| 220 | 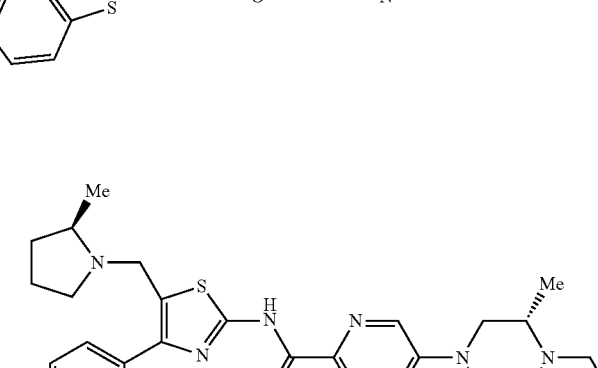 |

TABLE 49-continued
| PEx | Structure |
|---|---|
| 221 | 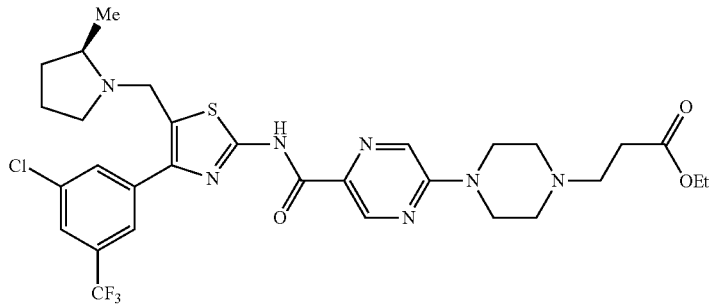 [SMILES: CCOC(=O)CCN1CCN(c2cnc(C(=O)Nc3nc(-c4cc(Cl)cc(C(F)(F)F)c4)c(CN4CCC[C@H]4C)s3)cn2)CC1] |
| 222 | 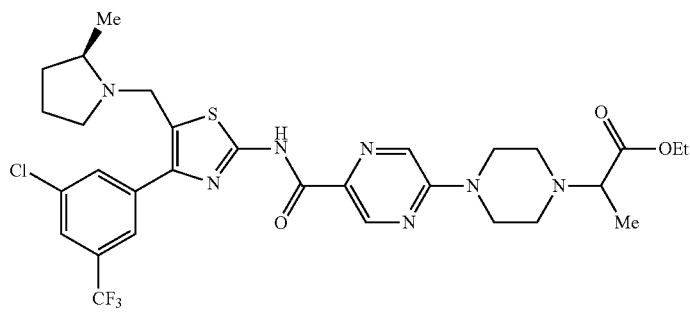 [SMILES: CCOC(=O)C(C)N1CCN(c2cnc(C(=O)Nc3nc(-c4cc(Cl)cc(C(F)(F)F)c4)c(CN4CCC[C@H]4C)s3)cn2)CC1] |
TABLE 50
| PEx | Structure |
|---|---|
| 223 | 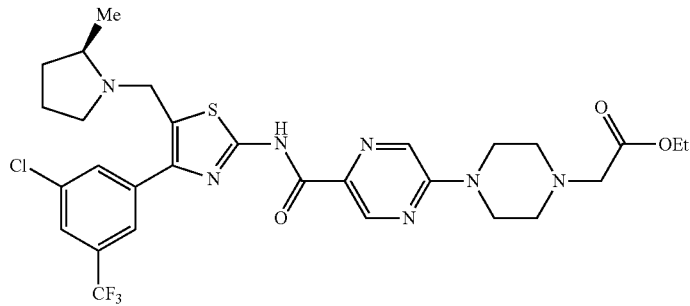 [SMILES: CCOC(=O)CN1CCN(c2cnc(C(=O)Nc3nc(-c4cc(Cl)cc(C(F)(F)F)c4)c(CN4CCC[C@H]4C)s3)cn2)CC1] |
| 224 | 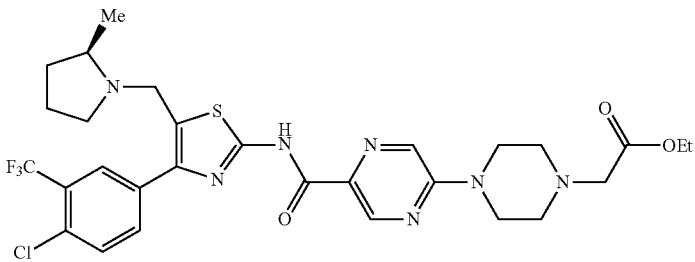 [SMILES: CCOC(=O)CN1CCN(c2cnc(C(=O)Nc3nc(-c4ccc(Cl)c(C(F)(F)F)c4)c(CN4CCC[C@H]4C)s3)cn2)CC1] |

TABLE 50-continued
| PEx | Structure |
|---|---|
| 225 | 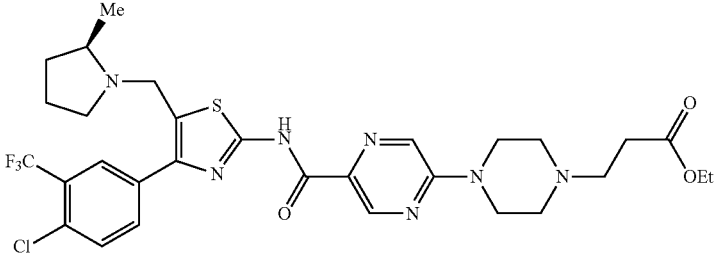 [SMILES: CCOC(=O)CCN1CCN(c2cnc(C(=O)Nc3nc(-c4ccc(Cl)c(C(F)(F)F)c4)c(CN4CCC[C@H]4C)s3)cn2)CC1] |
| 226 | 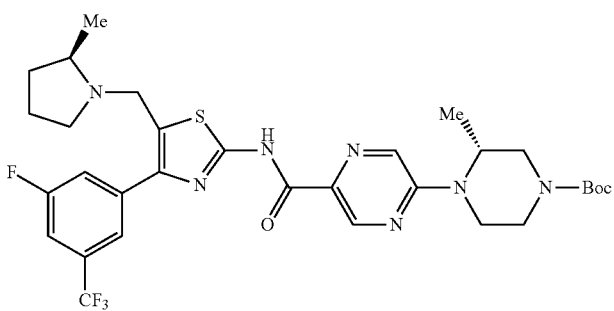 [SMILES: C[C@@H]1CCCN1Cc1sc(NC(=O)c2cnc(N3CCN(C(=O)OC(C)(C)C)C[C@H]3C)cn2)nc1-c1cc(F)cc(C(F)(F)F)c1] |
TABLE 51
| PEx | Structure |
|---|---|
| 227 | 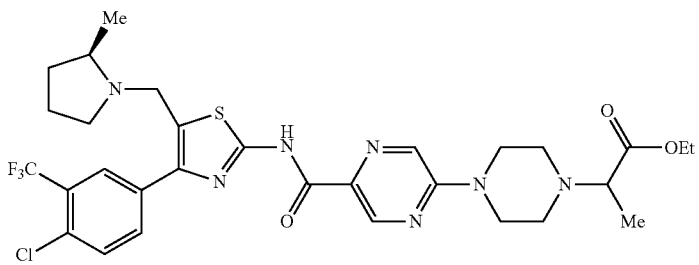 [SMILES: CCOC(=O)C(C)N1CCN(c2cnc(C(=O)Nc3nc(-c4ccc(Cl)c(C(F)(F)F)c4)c(CN4CCC[C@H]4C)s3)cn2)CC1] |
| 228 | 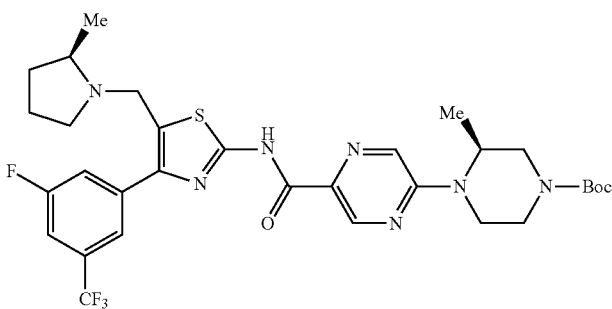 |

TABLE 51-continued
| PEx | Structure |
|---|---|
| 229 | 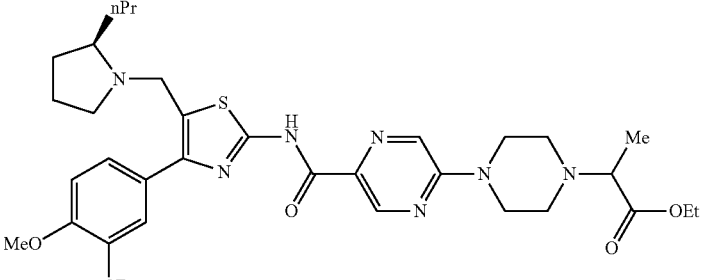 |
| 230 | 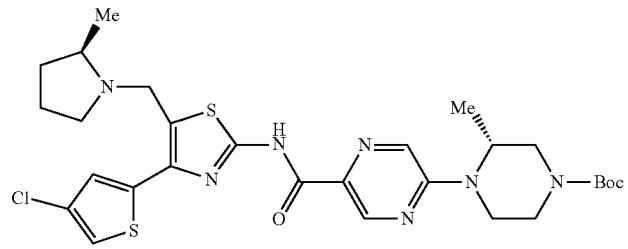 [SMILES: C[C@@H]1CCCN1Cc1sc(NC(=O)c2cnc(N3CCN(C(=O)OC(C)(C)C)C[C@H]3C)cn2)nc1-c1cc(Cl)cs1] |
| 231 | 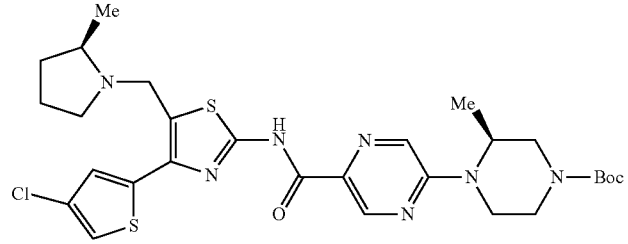 [SMILES: C[C@@H]1CCCN1Cc1sc(NC(=O)c2cnc(N3CCN(C(=O)OC(C)(C)C)C[C@@H]3C)cn2)nc1-c1cc(Cl)cs1] |
TABLE 52
| PEx | Structure |
|---|---|
| 232 | 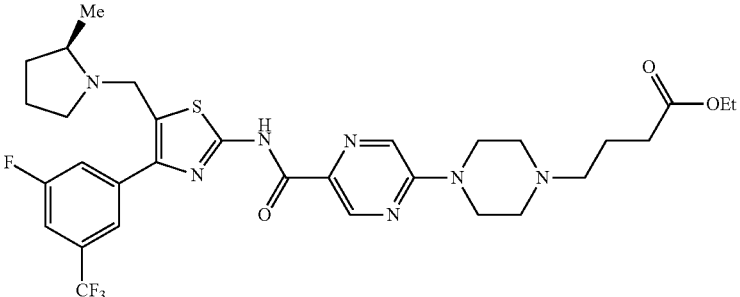 |
| 233 | 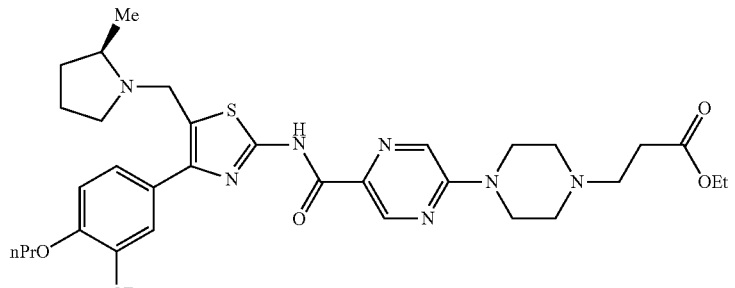 |

TABLE 52-continued
| PEx | Structure |
|---|---|
| 234 | 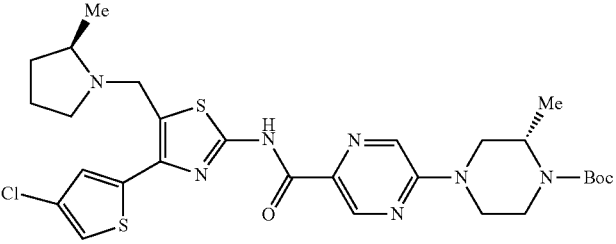 [SMILES: C[C@@H]1CCCN1Cc1sc(NC(=O)c2cnc(N3CCN(C(=O)OC(C)(C)C)[C@@H](C)C3)cn2)nc1-c1cc(Cl)cs1] |
| 235 | 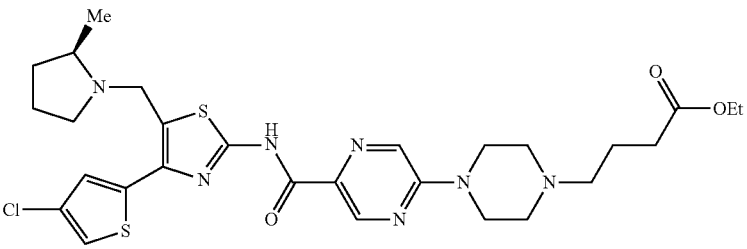 [SMILES: CCOC(=O)CCCN1CCN(c2cnc(C(=O)Nc3nc(-c4cc(Cl)cs4)c(CN4CCC[C@H]4C)s3)cn2)CC1] |
TABLE 53
| PEx | Structure |
|---|---|
| 236 | 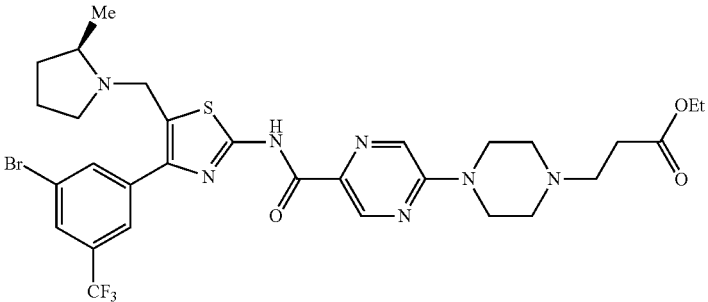 [SMILES: CCOC(=O)CCN1CCN(c2cnc(C(=O)Nc3nc(-c4cc(Br)cc(C(F)(F)F)c4)c(CN4CCC[C@H]4C)s3)cn2)CC1] |
| 237 | 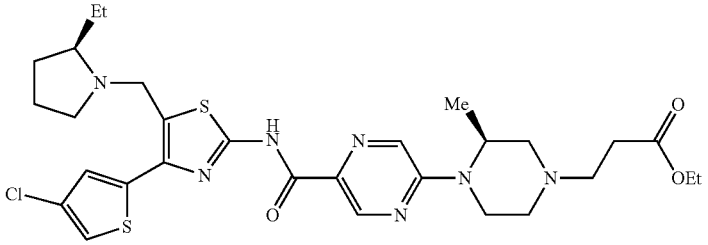 [SMILES: CCOC(=O)CCN1CCN(c2cnc(C(=O)Nc3nc(-c4cc(Cl)cs4)c(CN4CCC[C@H]4CC)s3)cn2)[C@@H](C)C1] |
| 238 | 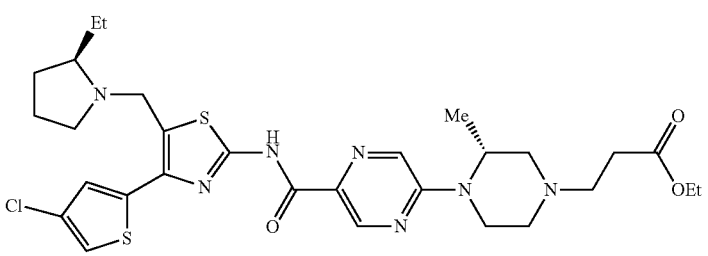 [SMILES: CCOC(=O)CCN1CCN(c2cnc(C(=O)Nc3nc(-c4cc(Cl)cs4)c(CN4CCC[C@H]4CC)s3)cn2)[C@H](C)C1] |

TABLE 53-continued
| PEx | Structure |
|---|---|
| 239 | 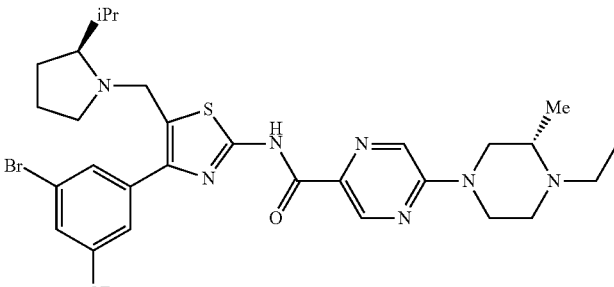 |
TABLE 54
| PEx | Structure |
|---|---|
| 240 | 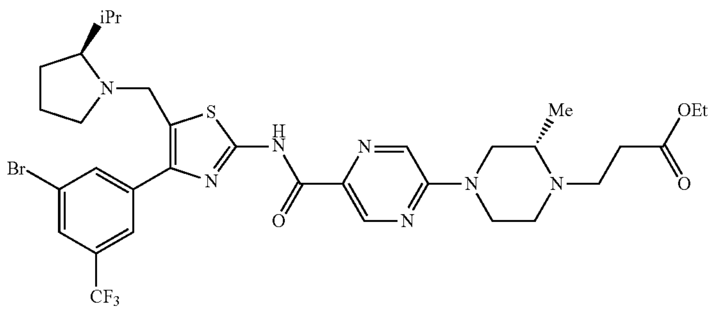 [SMILES: CCOC(=O)CCN1CCN(c2cnc(C(=O)Nc3nc(-c4cc(Br)cc(C(F)(F)F)c4)c(CN4CCC[C@H]4C(C)C)s3)cn2)C[C@@H]1C] |
| 241 | 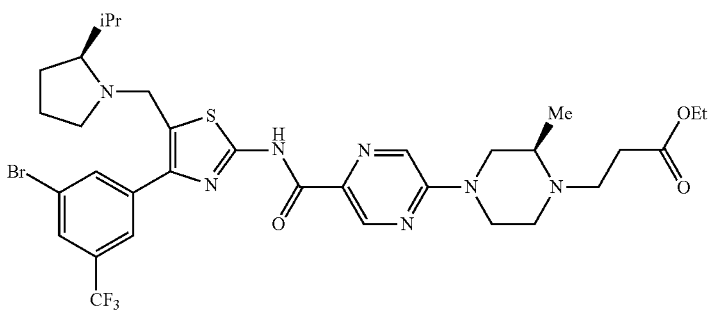 [SMILES: CCOC(=O)CCN1CCN(c2cnc(C(=O)Nc3nc(-c4cc(Br)cc(C(F)(F)F)c4)c(CN4CCC[C@H]4C(C)C)s3)cn2)C[C@H]1C] |
| 242 | 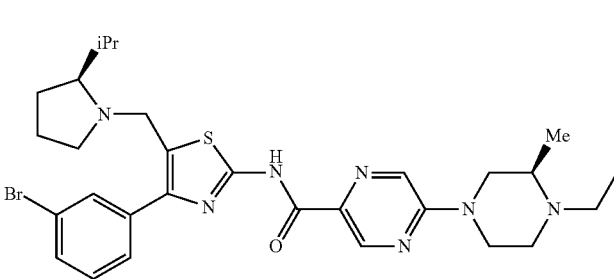 |

TABLE 54-continued
| PEx | Structure |
|---|---|
| 243 | 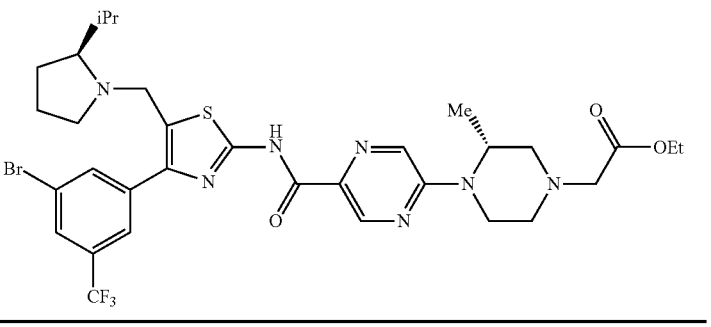 |
TABLE 55
| PEx | Structure |
|---|---|
| 244 | 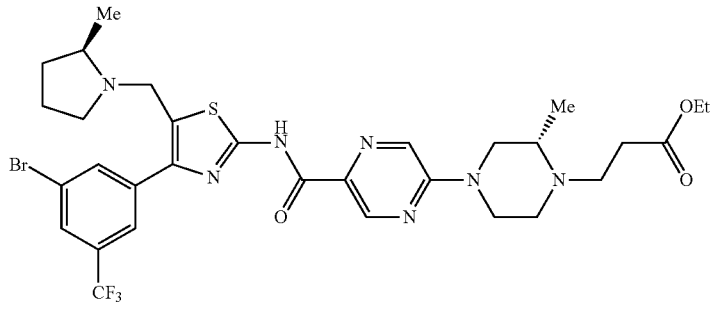 [SMILES: CCOC(=O)CCN1CCN(c2cnc(C(=O)Nc3nc(-c4cc(Br)cc(C(F)(F)F)c4)c(CN4CCC[C@H]4C)s3)cn2)C[C@@H]1C] |
| 245 | 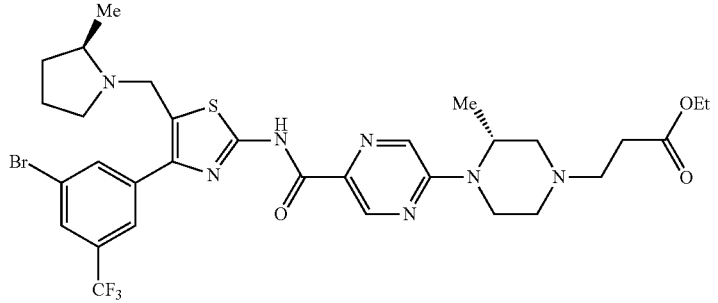 [SMILES: CCOC(=O)CCN1CCN(c2cnc(C(=O)Nc3nc(-c4cc(Br)cc(C(F)(F)F)c4)c(CN4CCC[C@H]4C)s3)cn2)[C@H](C)C1] |
| 246 | 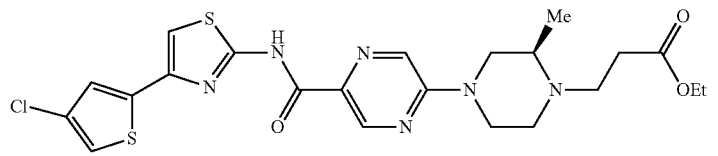 [SMILES: CCOC(=O)CCN1CCN(c2cnc(C(=O)Nc3nc(-c4cc(Cl)cs4)cs3)cn2)C[C@H]1C] |
| 247 | 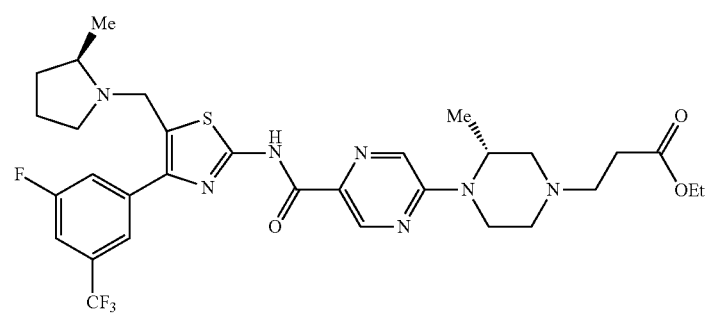 [SMILES: CCOC(=O)CCN1CCN(c2cnc(C(=O)Nc3nc(-c4cc(F)cc(C(F)(F)F)c4)c(CN4CCC[C@H]4C)s3)cn2)[C@H](C)C1] |

TABLE 56
| PEx | Structure |
|---|---|
| 248 | 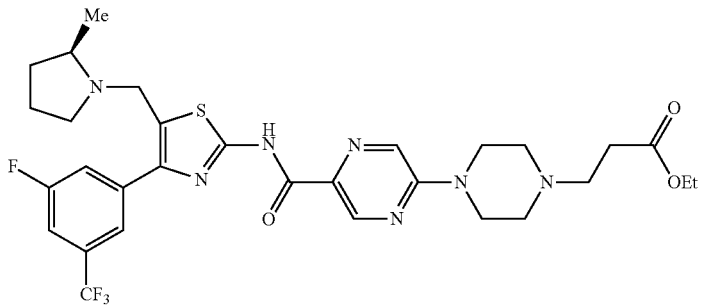 [SMILES: CCOC(=O)CCN1CCN(c2cnc(C(=O)Nc3nc(-c4cc(F)cc(C(F)(F)F)c4)c(CN4CCC[C@H]4C)s3)cn2)CC1] |
| 249 | 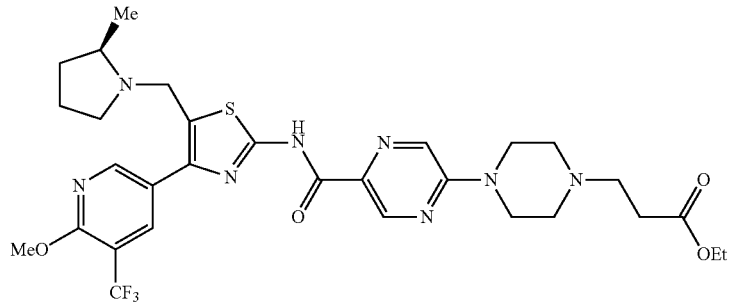 [SMILES: CCOC(=O)CCN1CCN(c2cnc(C(=O)Nc3nc(-c4cnc(OC)c(C(F)(F)F)c4)c(CN4CCC[C@H]4C)s3)cn2)CC1] |
| 250 | 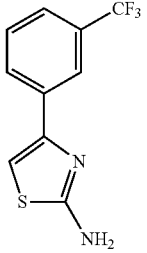 [SMILES: Nc1nc(-c2cccc(C(F)(F)F)c2)cs1] |
| 251 | 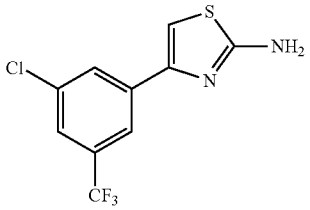 [SMILES: Nc1nc(-c2cc(Cl)cc(C(F)(F)F)c2)cs1] |
| TABLE 57 | | TABLE 57-continued | |
|---|---|---|---|
| PEx | Structure | PEx | Structure |
| 252 | 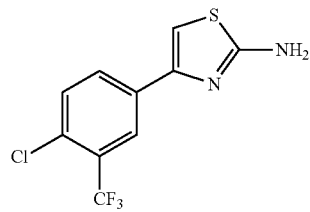 [SMILES: Nc1nc(-c2ccc(Cl)c(C(F)(F)F)c2)cs1] | 253 | 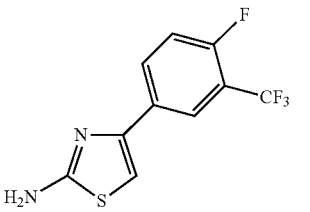 [SMILES: Nc1nc(-c2ccc(F)c(C(F)(F)F)c2)cs1] |

TABLE 57-continued
| PEx | Structure |
|---|---|
| 254 | 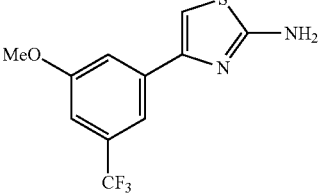 |
| 255 | 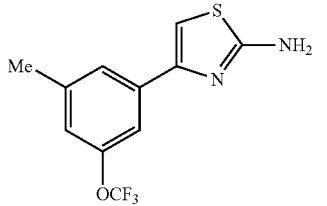 [SMILES: Cc1cc(OC(F)(F)F)cc(-c2csc(N)n2)c1] |
| 256 | 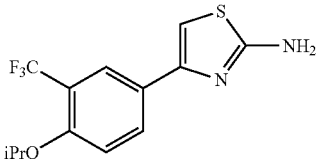 [SMILES: CC(C)Oc1ccc(-c2csc(N)n2)cc1C(F)(F)F] |
| 257 | 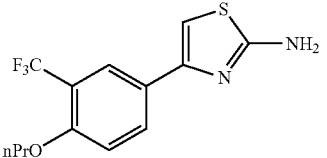 [SMILES: COc1ccc(-c2csc(N)n2)cc1C(F)(F)F] |
TABLE 58
| PEx | Structure |
|---|---|
| 258 | 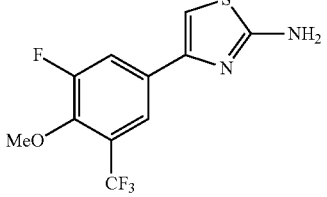 |
| 259 | 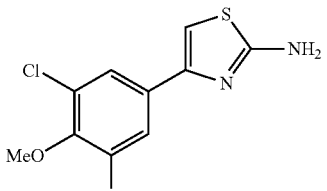 |
| 260 | 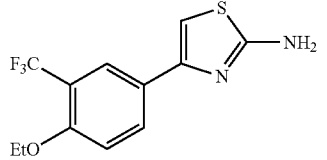 [SMILES: CCOc1ccc(-c2csc(N)n2)cc1C(F)(F)F] |
TABLE 58-continued
| PEx | Structure |
|---|---|
| 261 | 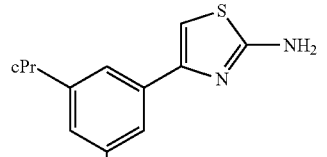 |
| 262 | 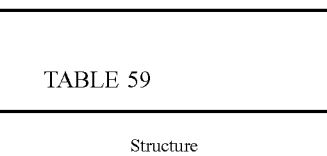 |
| 263 | 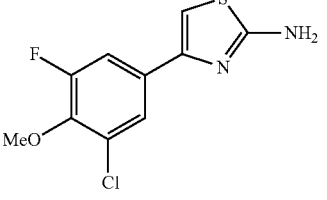 |
| 264 | 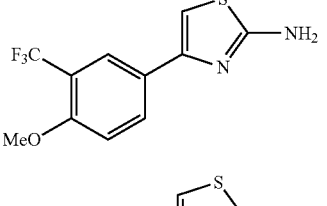 |
TABLE 59
| PEx | Structure |
|---|---|
| 265 | 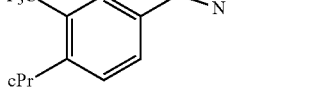 |
| 266 | 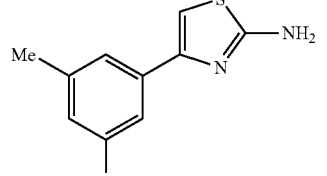 |

TABLE 59-continued
| PEx | Structure |
|---|---|
| 267 | 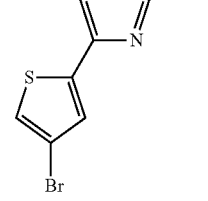 |
| 268 | 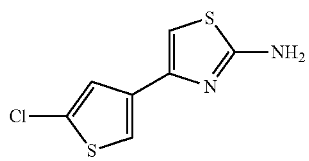 [SMILES: Nc1nc(-c2csc(Cl)c2)cs1] |
| 269 | 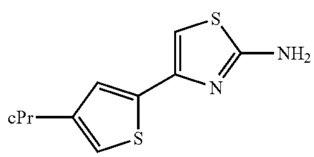 |
| 270 | 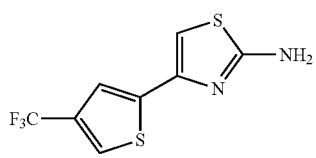 [SMILES: Nc1nc(-c2cc(C(F)(F)F)cs2)cs1] |
| 271 | 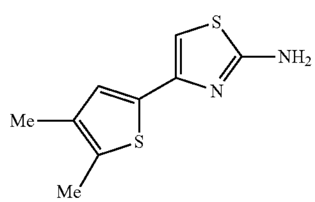 [SMILES: Cc1cc(-c2csc(N)n2)sc1C] |
TABLE 60
| PEx | Structure |
|---|---|
| 272 | |
| 273 | |
| 274 | 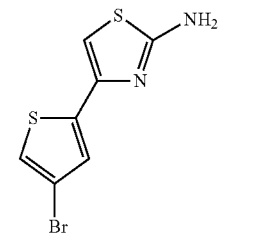 [SMILES: Nc1nc(-c2cc(Br)cs2)cs1] |
| 275 | 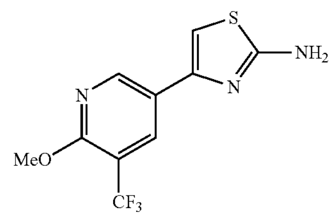 [SMILES: COc1ncc(-c2csc(N)n2)cc1C(F)(F)F] |
| 276 | 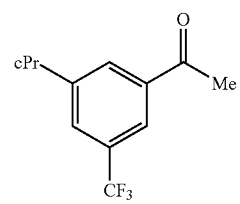 |
| 277 | 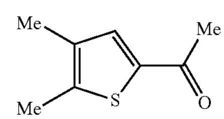 |
| 278 | 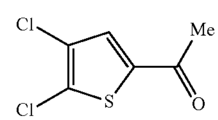 |
TABLE 61
| PEx | Structure |
|---|---|
| 279 | 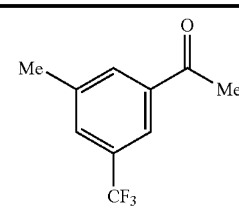 |
| 280 | 3HCl |

TABLE 61-continued

| PEx | Structure |
|---|---|
| 281 | 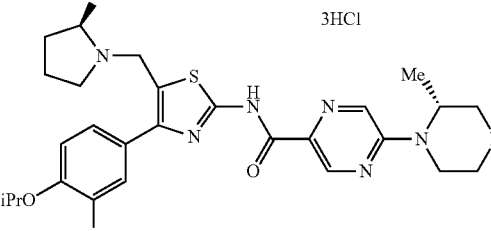 3HCl |
| 282 | 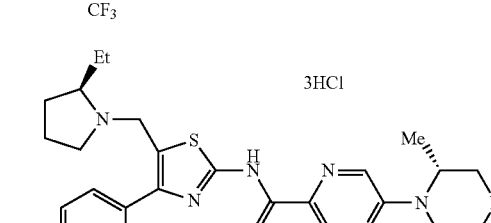 3HCl |
| 283 | 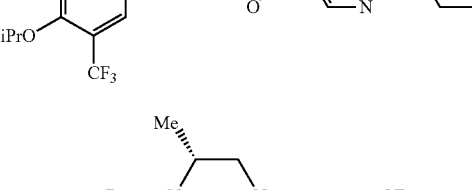 |

TABLE 62

| PEx | Structure |
|---|---|
| 284 | 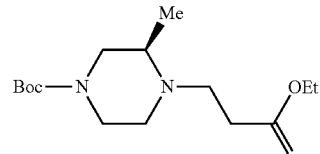 |
| 285 | 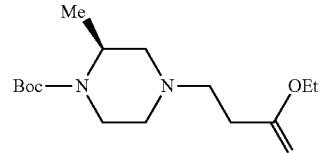 |

TABLE 63

| PEx | PSyn | Data |
|---|---|---|
| 1 | PEx1 | ESI+: 500, 502 |
| 2 | PEx2 | APCI/ESI+: 488 |
| 3 | PEx3 | NMR-DMSO-d6: 7.55 (1H, d, J = 1.5 Hz), 7.60 (1H, d, J = 1.5 Hz), 7.76 (1H, s), 8.98 (1H, d, J = 1.3 Hz), 9.15 (1H, d, J = 1.3 Hz), 12.68 (1H, brs) |
| 4 | PEx4 | ESI+: 265 |
| 5 | PEx5 | ESI+: 360 |
| 6 | PEx6 | ESI+: 374 |
| 7 | PEx7 | ESI+: 348 |
| 8 | PEx8 | ESI+: 564 |
| 9 | PEx9 | ESI+: 201 |

TABLE 63-continued

| PEx | PSyn | Data |
|---|---|---|
| 10 | PEx10 | ESI+: 100 |
| 11 | PEx11 | ESI+: 390 |
| 12 | PEx12 | ESI+: 418, 420 |
| 13 | PEx13 | ESI+: 377 |
| 14 | PEx14 | ESI+: 593, 595 |
| 15 | PEx15 | ESI+: 389 |
| 16 | PEx16 | ESI+: 402 |
| 17 | PEx17 | ESI+: 328 |
| 18 | PEx18 | ESI+: 618 |
| 19 | PEx19 | ESI+: 305 |
| 20 | PEx20 | ESI+: 313, 315 |
| 21 | PEx21 | ESI+: 664 |
| 22 | PEx22 | ESI+: 604 |
| 23 | PEx23 | ESI+: 233 |
| 24 | PEx24 | ESI+: 501 |
| 25 | PEx25 | ESI+: 650 |
| 26 | PEx26 | ESI+: 247 |
| 27 | PEx27 | ESI+: 200 |
| 28 | PEx28 | ESI+: 287 |
| 29 | PEx29 | ESI+: 521, 523 |
| 30 | PEx30 | ESI+: 263 |
| 31 | PEx31 | CI+: 195 |
| 32 | PEx32 | ESI+: 220 |

TABLE 64

| PEx | PSyn | Data |
|---|---|---|
| 33 | PEx33 | ESI+: 219 |
| 34 | PEx34 | ESI+: 222 |
| 35 | PEx35 | ESI+: 250 |
| 36 | PEx36 | CI+: 256, 258 |
| 37 | PEx37 | ESI+: 247 |
| 38 | PEx38 | EI: 228 |
| 39 | PEx39 | APCI/ESI+: 167 |
| 40 | PEx40 | EI: 266, 268 |
| 41 | PEx41 | ESI+: 237 |
| 42 | PEx42 | ESI+: 311 |
| 43 | PEx43 | ESI+: 590 |
| 44 | PEx44 | ESI+: 378 [M + Na]+ |
| 45 | PEx45 | ESI+: 301 |
| 46 | PEx1 | ESI+: 512, 514 |
| 47 | PEx1 | ESI+: 512 |
| 48 | PEx1 | ESI+: 454 |
| 49 | PEx1 | ESI+: 512 |
| 50 | PEx1 | ESI+: 526, 528 |
| 51 | PEx1 | ESI+: 540, 542 |
| 52 | PEx1 | ESI+: 540, 542 |
| 53 | PEx1 | ESI+: 554, 556 |
| 54 | PEx1 | ESI+: 516, 518 |
| 55 | PEx1 | ESI+: 500 |
| 56 | PEx1 | ESI+: 514, 516 |
| 57 | PEx1 | ESI+: 516, 518 |
| 58 | PEx1 | ESI+: 522 |
| 59 | PEx1 | ESI+: 496, 498 |
| 60 | PEx1 | ESI+: 522, 524 |
| 61 | PEx1 | ESI+: 536, 538 |
| 62 | PEx1 | ESI+: 496, 498 |
| 63 | PEx1 | ESI+: 540, 542 |
| 64 | PEx1 | ESI+: 530 |
| 65 | PEx1 | ESI+: 496 |
| 66 | PEx1 | ESI+: 548 |

TABLE 65

| PEx | PSyn | Data |
|---|---|---|
| 67 | PEx1 | ESI+: 540 |
| 68 | PEx2 | ESI+: 468 |
| 69 | PEx2 | ESI+: 454, 456 |
| 70 | PEx2 | ESI+: 560, 562 |
| 71 | PEx2 | ESI+: 510, 512 |
| 72 | PEx2 | ESI+: 510, 512 |

TABLE 65-continued

| PEx | PSyn | Data |
|---|---|---|
| 73 | PEx2 | ESI+: 496, 498 |
| 74 | PEx2 | ESI+: 510, 512 |
| 75 | PEx2 | APCI/ESI+: 460 |
| 76 | PEx2 | ESI+: 588, 590 |
| 77 | PEx2 | APCI/ESI+: 498 |
| 78 | PEx3 | ESI+: 434, 436 |
| 79 | PEx3 | ESI+: 448, 450 |
| 80 | PEx3 | ESI+: 514, 516 |
| 81 | PEx3 | ESI+: 514, 516 |
| 82 | PEx3 | ESI+: 502, 504 |
| 83 | PEx3 | ESI+: 502, 504 |
| 84 | PEx3 | ESI+: 500, 502 |
| 85 | PEx3 | ESI+: 514, 516 |
| 86 | PEx3 | ESI+: 502, 504 |
| 87 | PEx3 | ESI+: 554, 556 |
| 88 | PEx3 | ESI+: 468, 470 |
| 89 | PEx3 | ESI+: 513, 515 |
| 90 | PEx3 | ESI+: 415, 417 |
| 91 | PEx5 | ESI+: 372 |
| 92 | PEx5 | ESI−: 312 |
| 93 | PEx5 | ESI+: 372 |
| 94 | PEx5 | ESI+: 376, 378 |
| 95 | PEx5 | ESI+: 360 |
| 96 | PEx5 | ESI+: 374 |
| 97 | PEx5 | ESI+: 400 |
| 98 | PEx5 | ESI+: 356 |
| 99 | PEx5 | ESI+: 382 |
| 100 | PEx5 | ESI+: 396 |

TABLE 66

| PEx | PSyn | Data |
|---|---|---|
| 101 | PEx5 | ESI+: 356 |
| 102 | PEx5 | ESI+: 382 |
| 103 | PEx5 | NMR-DMSO-d6: 1.11 (3H, d, J = 6 Hz), 1.30-1.41 (1H, m), 1.59-1.69 (2H, m), 1.87-1.98 (1H, m), 2.05-2.15 (1H, m), 2.35-2.45 (1H, m), 2.94-3.02 (1H, m), 3.18 (1H, d, J = 14 Hz), 3.97 (3H, d, J = 2 Hz), 3.98 (1H, d, J = 14 Hz), 6.98 (2H, brs), 7.87 (1H, brs), 8.02 (1H, dd, J = 13, 2 Hz) |
| 104 | PEx5 | NMR-DMSO-d6: 1.14 (3H, d, J = 6 Hz), 1.30-1.42 (1H, m), 1.58-1.70 (2H, m), 1.87-1.98 (1H, m), 2.04-2.14 (1H, m), 2.34-2.44 (1H, m), 2.95-3.03 (1H, m), 3.14 (1H, d, J = 14 Hz), 3.91 (3H, d, J = 1 Hz), 3.98 (1H, d, J = 14 Hz), 6.93 (2H, brs), 7.63 (1H, dd, J = 13, 2 Hz), 7.72 (1H, t, J = 2 Hz) |
| 105 | PEx5 | NMR-DMSO-d6: 1.08 (3H, d, J = 6 Hz), 1.29-1.41 (1H, m), 1.58-1.70 (2H, m), 1.86-1.97 (1H, m), 2.05-2.17 (1H, m), 2.34-2.45 (1H, m), 2.94-3.03 (1H, m), 3.22 (1H, d, J = 14 Hz), 3.96 (1H, d, J = 14 Hz), 6.96 (2H, brs), 7.42 (1H, t, J = 73 Hz), 7.48 (1H, d, J = 9 Hz), 8.04 (1H, dd, J = 9, 2 Hz), 8.14 (1H, d, J = 2 Hz) |
| 106 | PEx5 | ESI+: 400 |
| 107 | PEx5 | ESI+: 370 |
| 108 | PEx5 | ESI+: 370 |
| 109 | PEx5 | ESI+: 356 |
| 110 | PEx5 | ESI+: 370 |
| 111 | PEx5 | ESI+: 420, 422 |
| 112 | PEx5 | ESI+: 448, 450 |
| 113 | PEx6 | ESI+: 374 |
| 114 | PEx6 | ESI+: 362 |
| 115 | PEx6 | ESI+: 362 |
| 116 | PEx7 | ESI+: 376, 378 |
| 117 | PEx7 | ESI+: 360 |
| 118 | PEx7 | ESI+: 376 |
| 119 | PEx7 | ESI+: 392 |
| 120 | PEx7 | ESI+: 374 |
| 121 | PEx7 | ESI+: 414 |
| 122 | PEx9 | ESI+: 201 |

TABLE 67

| PEx | PSyn | Data |
|---|---|---|
| 123 | PEx9 | ESI+: 201 |
| 124 | PEx9 | ESI+: 201 |
| 125 | PEx9 | ESI+: 187 |
| 126 | PEx11 | ESI+: 414 |
| 127 | PEx11 | ESI+: 356 |
| 128 | PEx11 | ESI+: 414 |
| 129 | PEx11 | ESI+: 416 |
| 130 | PEx11 | ESI+: 398 |
| 131 | PEx11 | ESI+: 424 |
| 132 | PEx11 | ESI+: 438 |
| 133 | PEx11 | ESI+: 398 |
| 134 | PEx11 | ESI+: 442 |
| 135 | PEx11 | ESI+: 424 |
| 136 | PEx11 | APCI/ESI+: 432 |
| 137 | PEx11 | APCI/ESI+: 398 |
| 138 | PEx11 | ESI+: 450 |
| 139 | PEx11 | ESI+: 442 |
| 140 | PEx11 | ESI+: 412 |
| 141 | PEx11 | ESI+: 412 |
| 142 | PEx11 | ESI+: 398 |
| 143 | PEx11 | ESI+: 412 |
| 144 | PEx11 | ESI+: 462, 464 |
| 145 | PEx11 | ESI+: 490, 492 |
| 146 | PEx11 | ESI+: 416 |
| 147 | PEx11 | ESI+: 416 |
| 148 | PEx11 | ESI+: 404 |
| 149 | PEx11 | ESI+: 404 |
| 150 | PEx11 | ESI+: 402 |
| 151 | PEx18 | ESI+: 632, 634 |
| 152 | PEx11 | ESI+: 418 |
| 153 | PEx11 | ESI+: 434 |
| 154 | PEx11 | ESI+: 416 |
| 155 | PEx11 | ESI+: 456 |
| 156 | PEx12 | ESI+: 418, 420 |

TABLE 68

| PEx | PSyn | Data |
|---|---|---|
| 157 | PEx13 | ESI+: 389 |
| 158 | PEx13 | ESI+: 331 |
| 159 | PEx13 | ESI+: 389 |
| 160 | PEx13 | ESI+: 393 |
| 161 | PEx13 | ESI+: 359 |
| 162 | PEx13 | ESI+: 399 |
| 163 | PEx13 | ESI+: 373 |
| 164 | PEx13 | ESI+: 399 |
| 165 | PEx13 | APCI/ESI+: 407 |
| 166 | PEx13 | APCI/ESI+: 373 |
| 167 | PEx13 | ESI+: 425 |
| 168 | PEx13 | ESI+: 417 |
| 169 | PEx13 | ESI+: 437, 439 |
| 170 | PEx13 | ESI+: 393, 395 |
| 171 | PEx14 | ESI+: 593, 595 |
| 172 | PEx16 | ESI+: 402 |
| 173 | PEx17 | ESI+: 372 |
| 174 | PEx17 | ESI+: 386 |
| 175 | PEx17 | ESI+: 400 |
| 176 | PEx17 | ESI+: 400 |
| 177 | PEx17 | ESI+: 414 |
| 178 | PEx17 | ESI+: 294 |
| 179 | PEx17 | ESI+: 308 |
| 180 | PEx17 | ESI+: 314 |
| 181 | PEx17 | APCI/ESI+: 320 |
| 182 | PEx17 | APCI/ESI+: 348 |
| 183 | PEx17 | APCI/ESI+: 358, 360 |
| 184 | PEx17 | ESI+: 362 |
| 185 | PEx17 | ESI+: 373 |
| 186 | PEx17 | ESI+: 328, 330 |
| 187 | PEx18 | ESI−: 510 |
| 188 | PEx18 | ESI+: 526 |
| 189 | PEx19 | ESI+: 321 |
| 190 | PEx19 | ESI+: 317 |

TABLE 69

| PEx | PSyn | Data |
|---|---|---|
| 191 | PEx19 | ESI+: 317 |
| 192 | PEx19 | ESI+: 259 |
| 193 | PEx19 | ESI+: 321 |
| 194 | PEx19 | ESI+: 317 |
| 195 | PEx19 | ESI+: 305 |
| 196 | PEx19 | ESI+: 287 |
| 197 | PEx19 | ESI+: 327 |
| 198 | PEx19 | ESI+: 301 |
| 199 | PEx19 | ESI+: 327 |
| 200 | PEx19 | ESI+: 335 |
| 201 | PEx19 | ESI+: 301 |
| 202 | PEx19 | ESI+: 353 |
| 203 | PEx19 | ESI+: 345 |
| 204 | PEx19 | ESI+: 365, 367 |
| 205 | PEx20 | NMR-DMSO-d6: 3.87 (3H, s), 8.01 (1H, s), 8.05 (2H, s) |
| 206 | PEx20 | ESI+: 385 |
| 207 | PEx20 | ESI+: 399 |
| 208 | PEx20 | ESI+: 293 |
| 209 | PEx20 | ESI+: 313, 315 |
| 210 | PEx20 | APCI/ESI+: 319 |
| 211 | PEx20 | APCI/ESI+: 347 |
| 212 | PEx20 | APCI/ESI+: 357 |
| 213 | PEx20 | ESI+: 372 |
| 214 | PEx21 | NMR-DMSO-d6: 1.13-1.26 (9H, m), 1.34-1.45 (1H, m), 1.60-1.76 (2H, m), 1.90-2.12 (2H, m), 2.16-2.28 (2H, m), 2.45-2.70 (5H, m), 2.78-2.85 (1H, m), 2.92-2.99 (1H, m), 3.00-3.07 (1H, m), 3.10-3.22 (1H, m), 3.55-3.62 (1H, m), 4.01-4.14 (2H, m), 4.15-4.23 (1H, m), 4.26-4.35 (1H, m), 4.66-4.78 (1H, m), 7.45 (1H, d, J = 1.5 Hz), 7.58 (1H, d, J = 1.3 Hz), 8.32 (1H, d, J = 1.1 Hz), 8.75 (1H, d, J = 1.2 Hz), 11.57 (1H, s) |
| 215 | PEx21 | ESI−: 616 |
| 216 | PEx22 | ESI+: 604 |
| 217 | PEx22 | ESI+: 604 |
| 218 | PEx24 | ESI+: 541, 543 |

TABLE 70

| PEx | PSyn | Data |
|---|---|---|
| 219 | PEx24 | ESI+: 523 |
| 220 | PEx29 | ESI+: 676 |
| 221 | PEx29 | ESI+: 666, 668 |
| 222 | PEx29 | ESI+: 666, 668 |
| 223 | PEx29 | ESI+: 652, 654 |
| 224 | PEx29 | ESI+: 652, 654 |
| 225 | PEx29 | ESI+: 666, 668 |
| 226 | PEx29 | ESI+: 664 |
| 227 | PEx29 | ESI+: 666, 668 |
| 228 | PEx29 | ESI+: 664 |
| 229 | PEx29 | ESI+: 690 |
| 230 | PEx29 | ESI+: 618, 620 |
| 231 | PEx29 | ESI+: 618 |
| 232 | PEx29 | ESI+: 664 |
| 233 | PEx29 | ESI+: 690 |
| 234 | PEx29 | ESI+: 618 |
| 235 | PEx29 | ESI+: 618 |
| 236 | PEx29 | ESI+: 710, 712 |
| 237 | PEx29 | ESI+: 632, 634 |
| 238 | PEx29 | ESI+: 632, 634 |
| 239 | PEx29 | ESI+: 738, 740 |
| 240 | PEx29 | ESI+: 752, 754 |
| 241 | PEx29 | ESI+: 752, 754 |
| 242 | PEx29 | ESI+: 752, 754 |
| 243 | PEx29 | ESI+: 738, 740 |
| 244 | PEx29 | ESI+: 724, 726 |
| 245 | PEx29 | ESI+: 724, 726 |
| 246 | PEx29 | ESI−: 519, 521 |
| 247 | PEx29 | ESI+: 664 |
| 248 | PEx29 | ESI+: 650 |
| 249 | PEx29 | ESI+: 663 |
| 250 | PEx30 | ESI+: 245 |
| 251 | PEx30 | ESI+: 279 |
| 252 | PEx30 | ESI+: 279, 281 |

TABLE 71

| PEx | PSyn | Data |
|---|---|---|
| 253 | PEx30 | ESI+: 263 |
| 254 | PEx30 | ESI+: 275 |
| 255 | PEx30 | ESI+: 275 |
| 256 | PEx30 | ESI+: 303 |
| 257 | PEx30 | ESI+: 303 |
| 258 | PEx30 | ESI+: 259, 261 |
| 259 | PEx30 | ESI+: 275 |
| 260 | PEx30 | ESI+: 285 |
| 261 | PEx30 | ESI+: 293 |
| 262 | PEx30 | ESI+: 275 |
| 263 | PEx30 | ESI+: 289 |
| 264 | PEx30 | ESI+: 285 |
| 265 | PEx30 | ESI+: 259 |
| 266 | PEx30 | ESI+: 323, 325 |
| 267 | PEx30 | ESI+: 197 |
| 268 | PEx30 | ESI+: 217, 219 |
| 269 | PEx30 | APCI/ESI+: 223 |
| 270 | PEx30 | APCI/ESI+: 251 |
| 271 | PEx30 | ESI+: 211 |
| 272 | PEx30 | ESI+: 233 |
| 273 | PEx30 | ESI+: 251, 253 |
| 274 | PEx30 | APCI/ESI+: 261, 263 |
| 275 | PEx30 | ESI+: 276 |
| 276 | PEx38 | EI: 228 |
| 277 | PEx40 | ESI+: 155 |
| 278 | PEx40 | EI: 194, 196 |
| 279 | PEx41 | EI: 202 |
| 280 | PEx43 | ESI+: 604 |
| 281 | PEx43 | ESI+: 604 |
| 282 | PEx43 | ESI+: 618 |
| 283 | PEx45 | ESI+: 301 |
| 284 | PEx45 | ESI+: 301 |
| 285 | PEx45 | ESI+: 301 |

TABLE 72

| Ex | Structure |
|---|---|
| 1 | ![structure of example 1: a chloro-thiophene connected to a thiazole bearing a (2-methylpyrrolidin-1-yl)methyl group, linked via an amide to a pyrazine-carboxamide connected to a (3-methylpiperazin-1-yl) group bearing a propanoic acid, as 2HCl salt] |

TABLE 72-continued
| Ex | Structure |
|---|---|
| 2 | 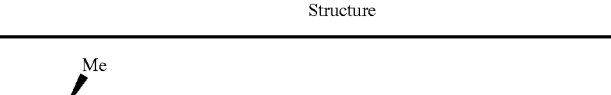 |
| 3 | 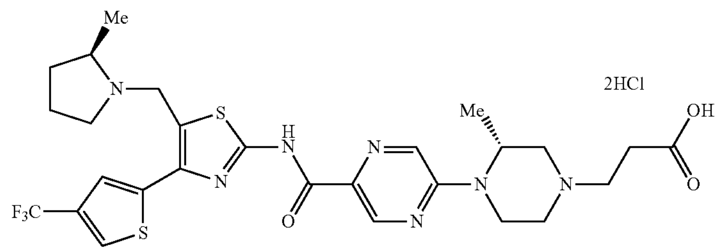 [SMILES: C[C@@H]1CCCN1Cc1sc(NC(=O)c2cnc(N3CCN(CCC(=O)O)C[C@H]3C)cn2)nc1-c1cc(C(F)(F)F)cs1] |
| 4 | 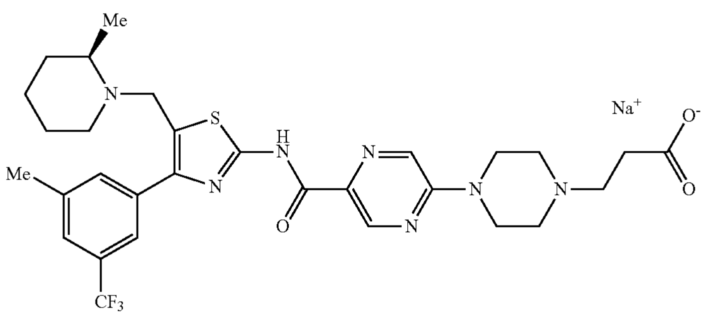 [SMILES: Cc1cc(-c2nc(NC(=O)c3cnc(N4CCN(CCC(=O)[O-])CC4)cn3)sc2CN2CCCC[C@H]2C)cc(C(F)(F)F)c1 ; [Na+]] |
| 5 | 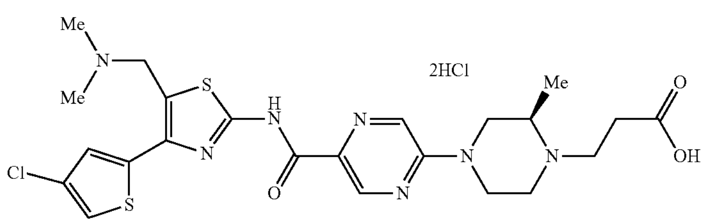 [SMILES: C[C@@H]1CN(c2cnc(C(=O)Nc3nc(-c4cc(Cl)cs4)c(CN(C)C)s3)cn2)CCN1CCC(=O)O] |
TABLE 73
| Ex | Structure |
|---|---|
| 6 | 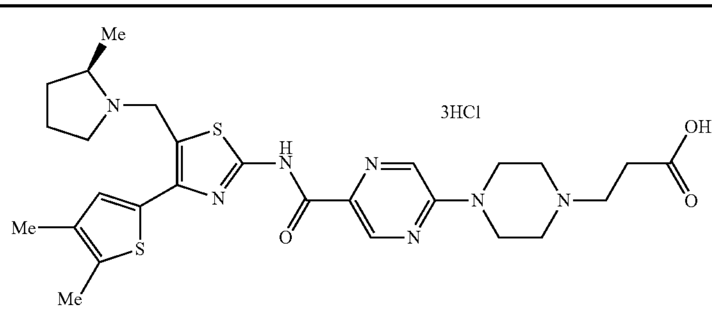 |

TABLE 73-continued
| Ex | Structure |
|---|---|
| 7 | 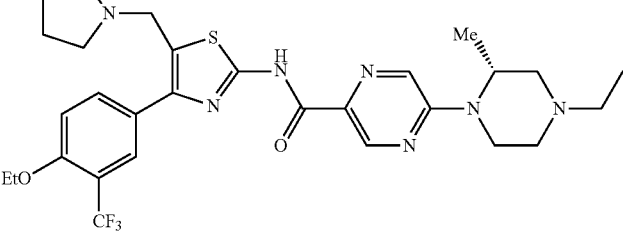 |
| 8 | 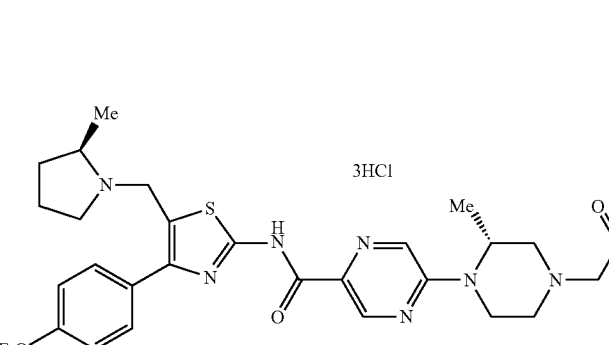 |
| 9 | 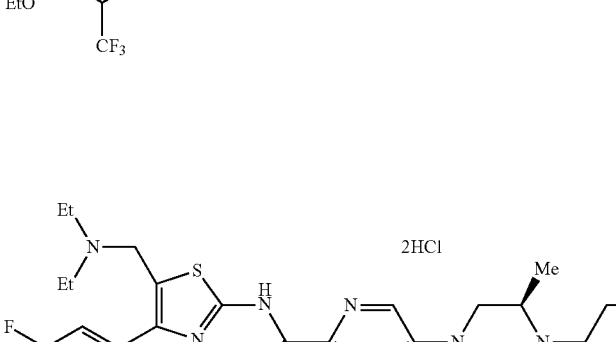 |
TABLE 74
| Ex | Structure |
|---|---|
| 10 | 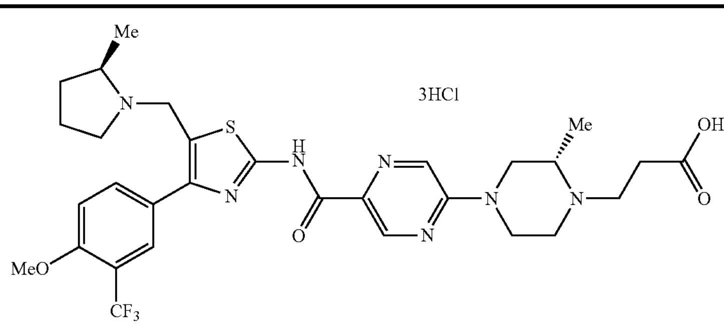 |

TABLE 74-continued

| Ex | Structure |
|---|---|
| 11 | (structure: (2S)-2-methylpyrrolidin-1-ylmethyl-[4-(3-chloro-5-trifluoromethylphenyl)thiazol-2-yl]-NH-C(O)-pyrazine-piperazine-CH2CH2-COOH, 3HCl) |
| 12 | (structure: (2S)-2-methylpyrrolidin-1-ylmethyl-[4-(3-chloro-5-trifluoromethylphenyl)thiazol-2-yl]-NH-C(O)-pyrazine-piperazine-CH(Me)-COOH, 3HCl) |
| 13 | (structure: (2S)-2-methylpyrrolidin-1-ylmethyl-[4-(3-chloro-5-trifluoromethylphenyl)thiazol-2-yl]-NH-C(O)-pyrazine-piperazine-CH2-COOH, 3HCl) |

TABLE 75

| Ex | Structure |
|---|---|
| 14 | (structure: (2S)-2-methylpyrrolidin-1-ylmethyl-[4-(4-chloro-3-trifluoromethylphenyl)thiazol-2-yl]-NH-C(O)-pyrazine-piperazine-CH2-COOH, 3HCl) |

TABLE 75-continued

| Ex | Structure |
|---|---|
| 15 | (chemical structure) 3HCl |
| 16 | (chemical structure) 3HCl |
| 17 | (chemical structure) 3HCl |

TABLE 76

| Ex | Structure |
|---|---|
| 18 | (chemical structure) 2HCl |
| 19 | (chemical structure) 3HCl |

TABLE 76-continued
| Ex | Structure |
|---|---|
| 20 | 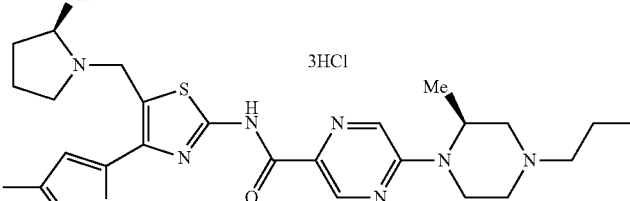 |
| 21 | 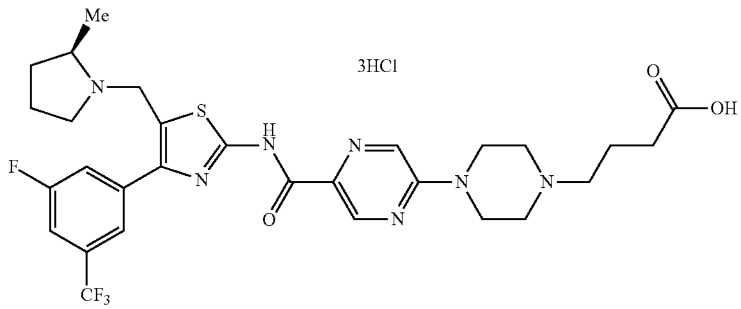 [SMILES: C[C@@H]1CCCN1Cc1sc(NC(=O)c2cnc(N3CCN(CCCC(=O)O)CC3)cn2)nc1-c1cc(F)cc(C(F)(F)F)c1] |
| 22 | 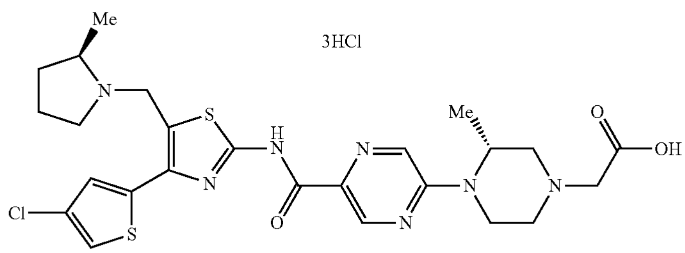 [SMILES: C[C@@H]1CCCN1Cc1sc(NC(=O)c2cnc(N3CCN(CC(=O)O)C[C@H]3C)cn2)nc1-c1cc(Cl)cs1] |
TABLE 77
| Ex | Structure |
|---|---|
| 23 | 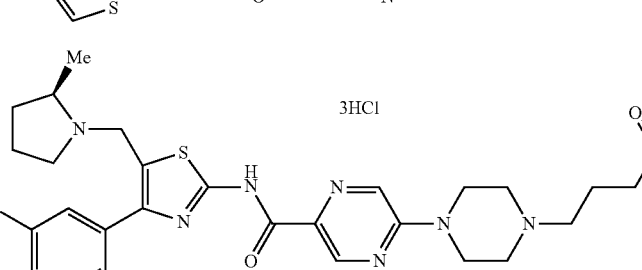 |
| 24 | 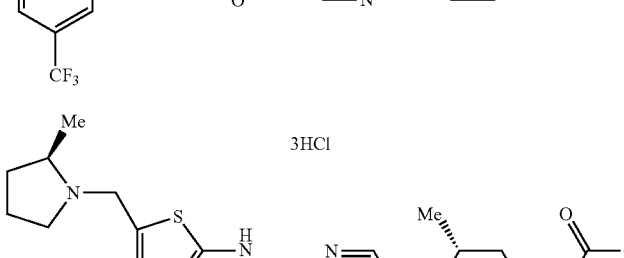 |

TABLE 77-continued
| Ex | Structure |
|---|---|
| 25 | 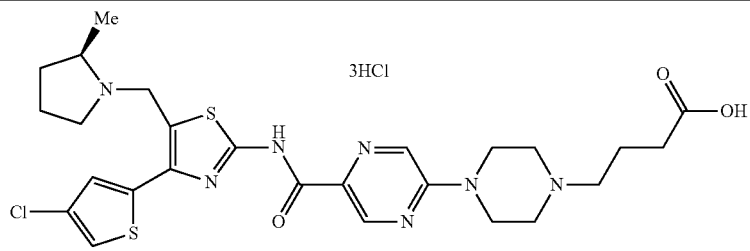 3HCl |
| 26 | 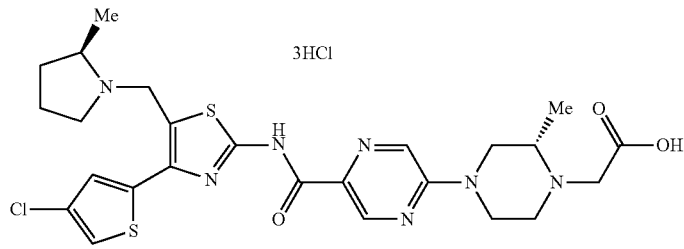 [SMILES: C[C@@H]1CCCN1Cc1sc(NC(=O)c2cnc(N3CCN(CC(=O)O)[C@@H](C)C3)cn2)nc1-c1cc(Cl)cs1] 3HCl |
| 27 | 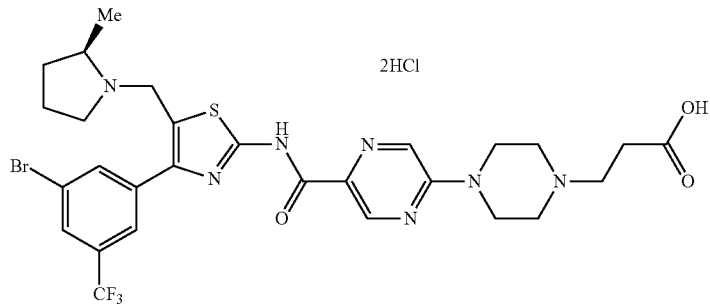 [SMILES: C[C@@H]1CCCN1Cc1sc(NC(=O)c2cnc(N3CCN(CCC(=O)O)CC3)cn2)nc1-c1cc(Br)cc(C(F)(F)F)c1] 2HCl |
TABLE 78
| Ex | Structure |
|---|---|
| 28 | 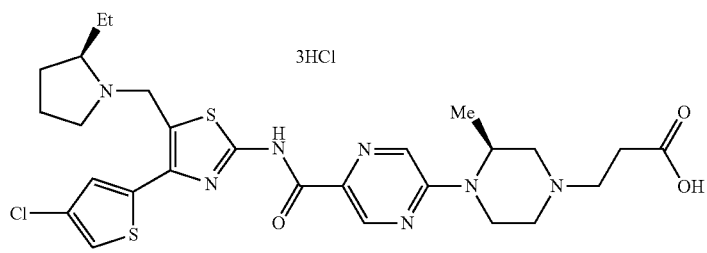 [SMILES: CC[C@@H]1CCCN1Cc1sc(NC(=O)c2cnc(N3CCN(CCC(=O)O)C[C@@H]3C)cn2)nc1-c1cc(Cl)cs1] 3HCl |
| 29 | 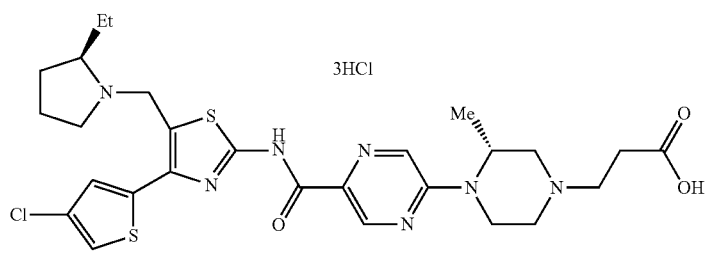 [SMILES: CC[C@@H]1CCCN1Cc1sc(NC(=O)c2cnc(N3CCN(CCC(=O)O)C[C@H]3C)cn2)nc1-c1cc(Cl)cs1] 3HCl |

TABLE 78-continued
| Ex | Structure |
|---|---|
| 30 | 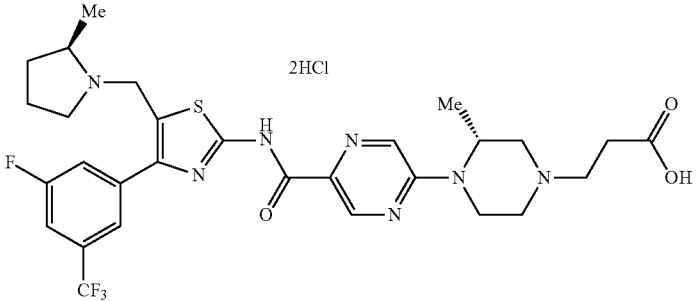 |
| 31 | 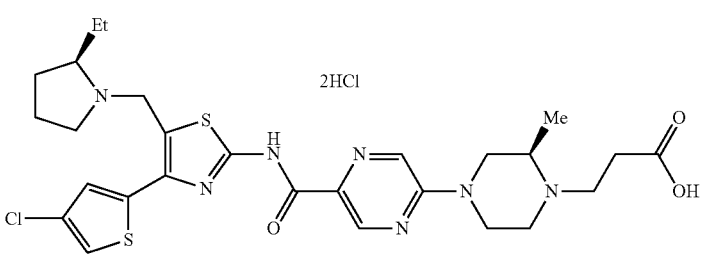 [SMILES: CC[C@@H]1CCCN1Cc1sc(NC(=O)c2cnc(N3CCN(CCC(=O)O)[C@H](C)C3)cn2)nc1-c1cc(Cl)cs1] |
| 32 | 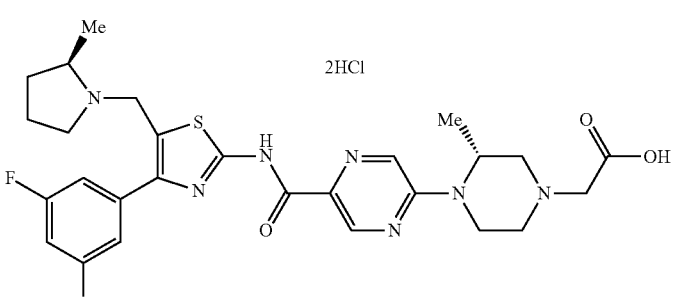 |
TABLE 79
| Ex | Structure |
|---|---|
| 33 | 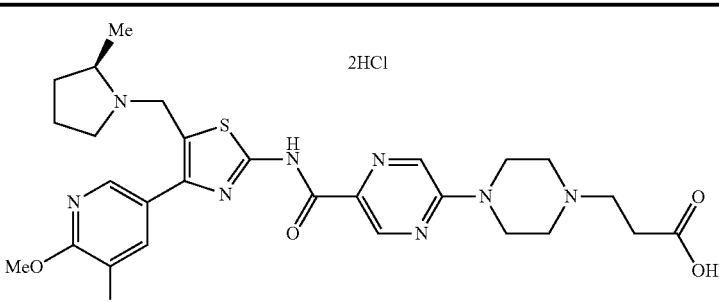 |

TABLE 79-continued

| Ex | Structure |
|---|---|
| 34 | (structure) |
| 35 | (structure) |
| 36 | (structure) |

TABLE 80

| Ex | Structure |
|---|---|
| 37 | (structure) |

TABLE 80-continued

| Ex | Structure |
|---|---|
| 38 | (2-iPr-pyrrolidinyl-methyl)-[4-(3-CN-5-CF3-phenyl)thiazol-2-yl]-NH-C(O)-pyrazine-piperazine(3-Me)-CH2-CO2⁻ Na⁺ |
| 39 | (2-Me-pyrrolidinyl-methyl)-[4-(3-CN-5-CF3-phenyl)thiazol-2-yl]-NH-C(O)-pyrazine-piperazine(3-Me)-CH2CH2-CO2⁻ Na⁺ |
| 40 | (2-Me-pyrrolidinyl-methyl)-[4-(3-CN-5-CF3-phenyl)thiazol-2-yl]-NH-C(O)-pyrazine-piperazine(3-Me)-CH2CH2-CO2⁻ Na⁺ |

TABLE 81

| Ex | Structure |
|---|---|
| 41 | (2-Et-pyrrolidinyl-methyl)-[4-(4-MeO-3-CF3-phenyl)thiazol-2-yl]-NH-C(O)-pyrazine-piperazine-CH2-CO2H · 3HCl |

TABLE 81-continued
| Ex | Structure |
|---|---|
| 42 | 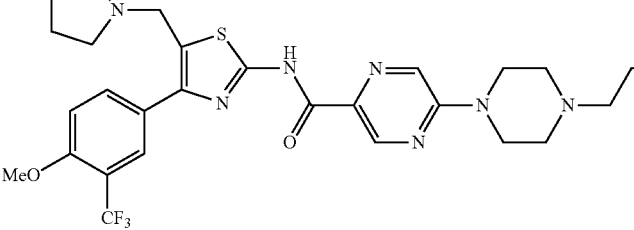 3HCl |
| 43 | 3HCl |
| 44 | 3HCl |
TABLE 82
| Ex | Structure |
|---|---|
| 45 | 3HCl |

TABLE 82-continued
| Ex | Structure |
|---|---|
| 46 | 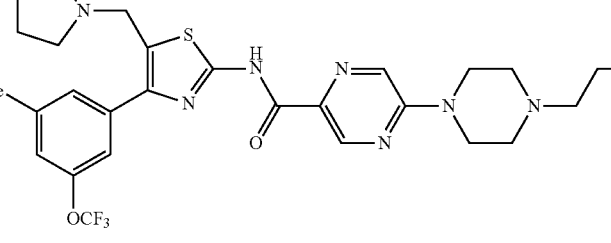 |
| 47 | 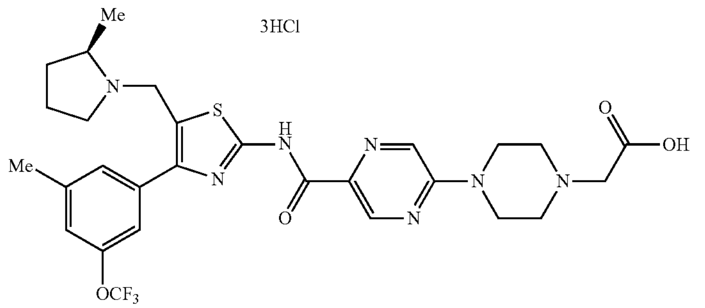 [SMILES: Cc1cc(OC(F)(F)F)cc(-c2nc(NC(=O)c3cnc(N4CCN(CC(=O)O)CC4)cn3)sc2CN2CCC[C@H]2C)c1] |
| 48 | 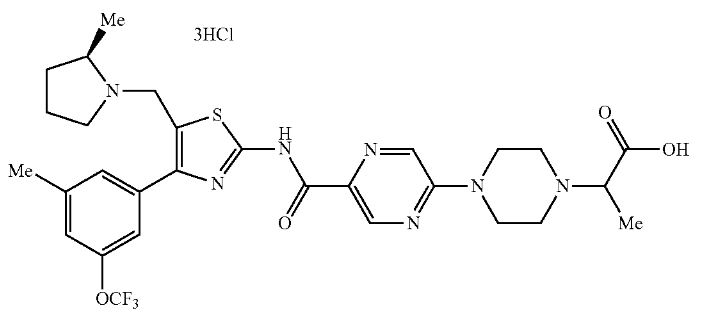 [SMILES: Cc1cc(OC(F)(F)F)cc(-c2nc(NC(=O)c3cnc(N4CCN(C(C)C(=O)O)CC4)cn3)sc2CN2CCC[C@H]2C)c1] |
TABLE 83
| Ex | Structure |
|---|---|
| 49 | 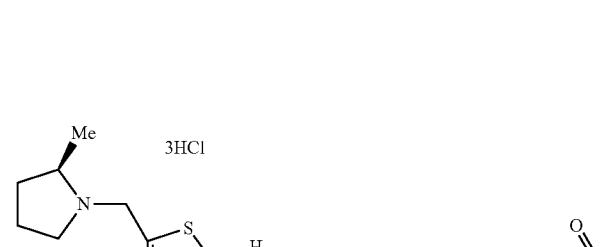 |

TABLE 83-continued
| Ex | Structure |
|---|---|
| 50 | 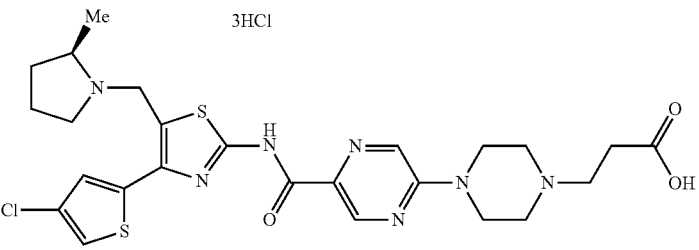 [SMILES: C[C@@H]1CCCN1Cc1sc(NC(=O)c2cnc(N3CCN(CCC(=O)O)CC3)cn2)nc1-c1cc(Cl)cs1] 3HCl |
| 51 | 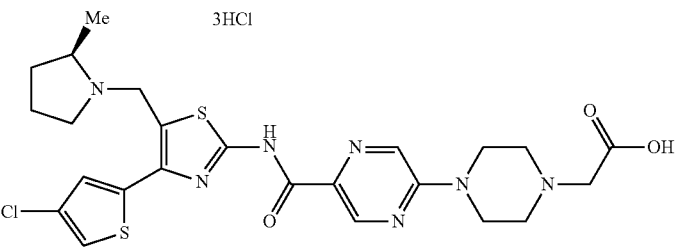 [SMILES: C[C@@H]1CCCN1Cc1sc(NC(=O)c2cnc(N3CCN(CC(=O)O)CC3)cn2)nc1-c1cc(Cl)cs1] 3HCl |
| 52 | 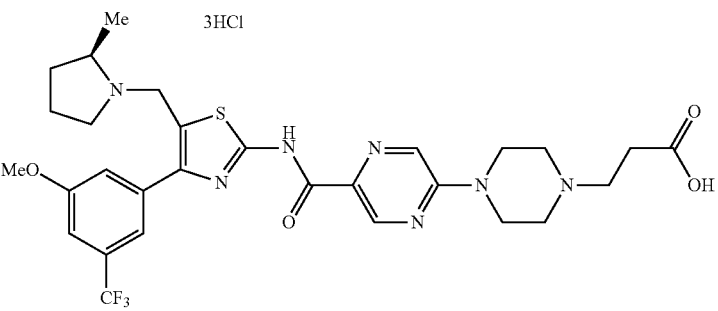 [SMILES: COc1cc(-c2nc(NC(=O)c3cnc(N4CCN(CCC(=O)O)CC4)cn3)sc2CN2CCC[C@H]2C)cc(C(F)(F)F)c1] 3HCl |
TABLE 84
| Ex | Structure |
|---|---|
| 53 | 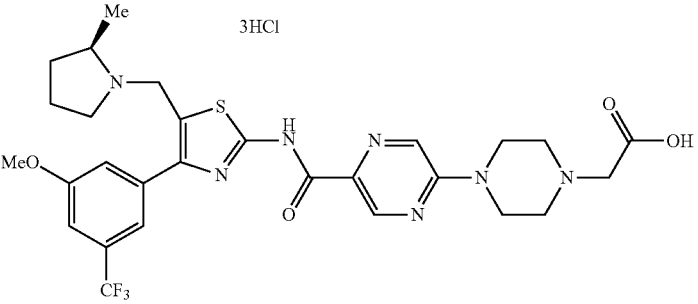 [SMILES: COc1cc(-c2nc(NC(=O)c3cnc(N4CCN(CC(=O)O)CC4)cn3)sc2CN2CCC[C@H]2C)cc(C(F)(F)F)c1] 3HCl |
| 54 | 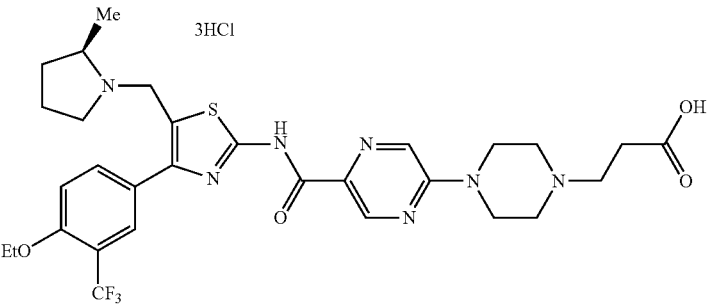 [SMILES: CCOc1ccc(-c2nc(NC(=O)c3cnc(N4CCN(CCC(=O)O)CC4)cn3)sc2CN2CCC[C@H]2C)cc1C(F)(F)F] 3HCl |

TABLE 84-continued
| Ex | Structure |
|----|-----------|
| 55 | 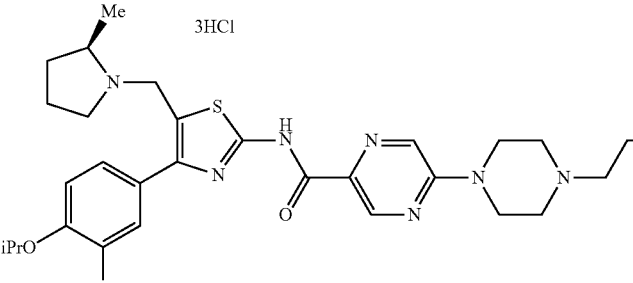 |
| 56 | 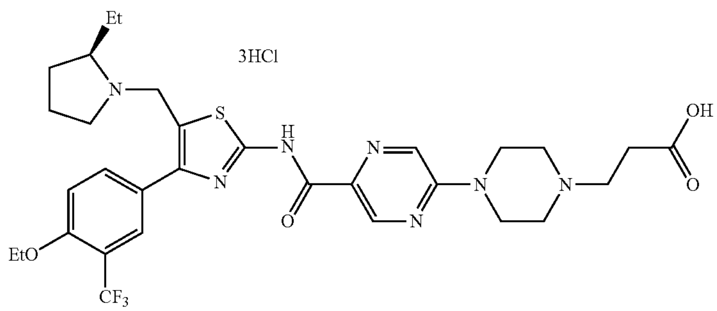 [SMILES: CCOc1ccc(-c2nc(NC(=O)c3cnc(N4CCN(CCC(=O)O)CC4)cn3)sc2CN2CCC[C@H]2CC)cc1C(F)(F)F] |
TABLE 85
| Ex | Structure |
|----|-----------|
| 57 | 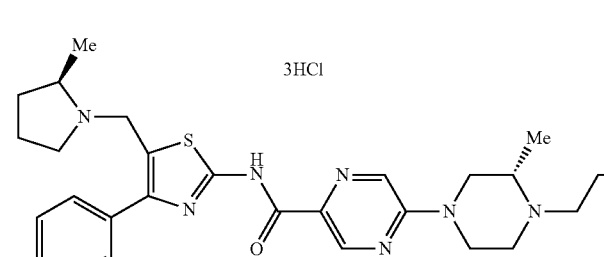 |
| 58 | 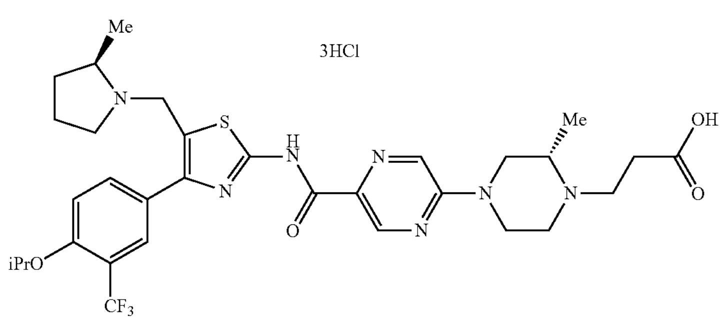 [SMILES: CC(C)Oc1ccc(-c2nc(NC(=O)c3cnc(N4CCN(CCC(=O)O)[C@@H](C)C4)cn3)sc2CN2CCC[C@H]2C)cc1C(F)(F)F] |

TABLE 85-continued

| Ex | Structure |
|---|---|
| 59 | (2-Et-pyrrolidinyl)methyl-thiazole [4-(4-iPrO-3-CF3-phenyl)]-2-NH-C(O)-pyrazine-piperazine-CH2CH2-COOH · 3HCl |
| 60 | (2-Me-pyrrolidinyl)methyl-thiazole [4-(4-F-3-CF3-phenyl)]-2-NH-C(O)-pyrazine-piperazine-CH2CH2-COOH · 3HCl |

TABLE 86

| Ex | Structure |
|---|---|
| 61 | (2-Me-pyrrolidinyl)methyl-thiazole [4-(4-F-3-CF3-phenyl)]-2-NH-C(O)-pyrazine-piperazine-CH2-COOH · 3HCl |
| 62 | (2-Et-pyrrolidinyl)methyl-thiazole [4-(3-F-5-CF3-phenyl)]-2-NH-C(O)-pyrazine-piperazine-CH2-COOH · 3HCl |

TABLE 86-continued
| Ex | Structure |
|---|---|
| 63 | 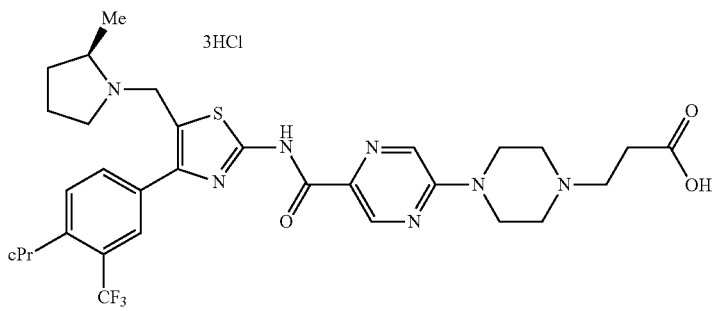 |
| 64 | 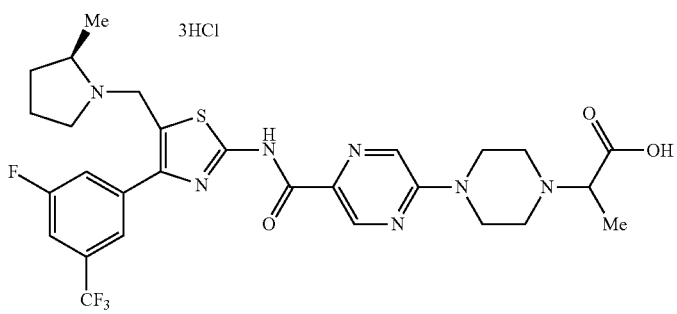 [SMILES: CC(C(=O)O)N1CCN(c2cnc(C(=O)Nc3nc(-c4cc(F)cc(C(F)(F)F)c4)c(CN4CCC[C@H]4C)s3)cn2)CC1] |
TABLE 87
| Ex | Structure |
|---|---|
| 65 | 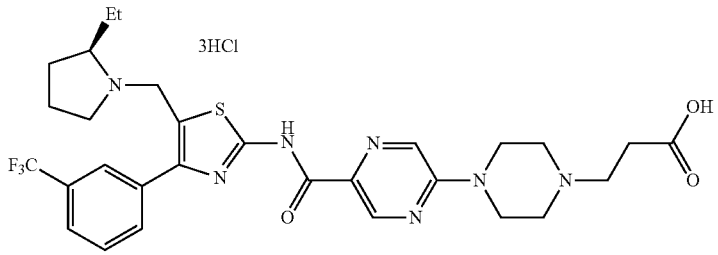 [SMILES: CC[C@@H]1CCCN1Cc1sc(NC(=O)c2cnc(N3CCN(CCC(=O)O)CC3)cn2)nc1-c1cccc(C(F)(F)F)c1] |
| 66 | 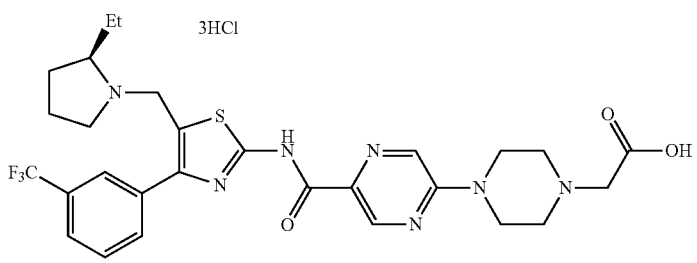 [SMILES: CC[C@@H]1CCCN1Cc1sc(NC(=O)c2cnc(N3CCN(CC(=O)O)CC3)cn2)nc1-c1cccc(C(F)(F)F)c1] |

TABLE 87-continued
| Ex | Structure |
|---|---|
| 67 | 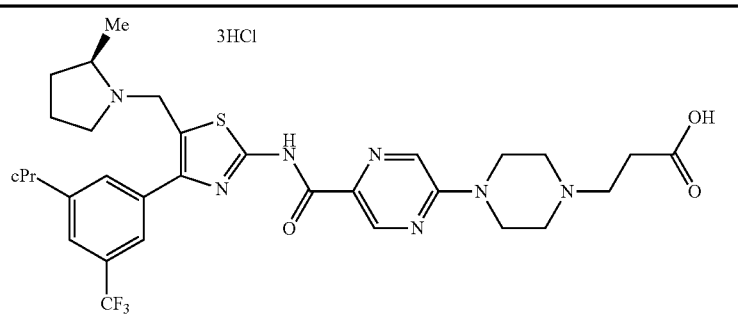 |
| 68 | 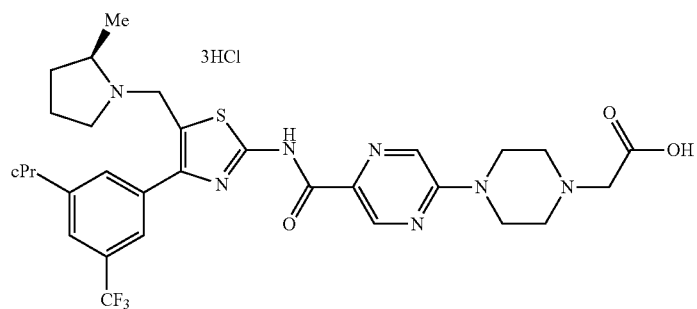 |
TABLE 88
| Ex | Structure |
|---|---|
| 69 | 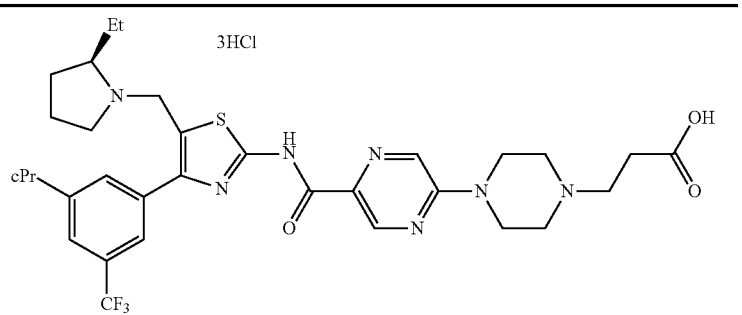 |
| 70 | 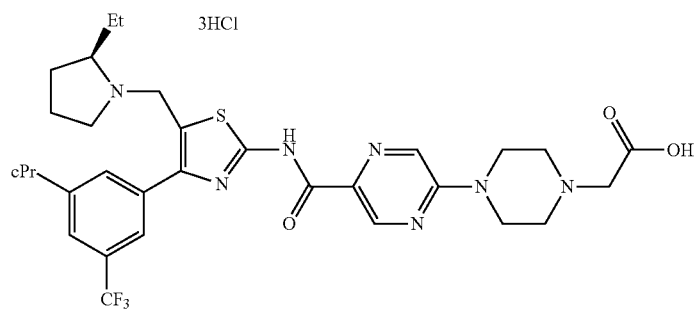 |

TABLE 88-continued
| Ex | Structure |
|---|---|
| 71 | 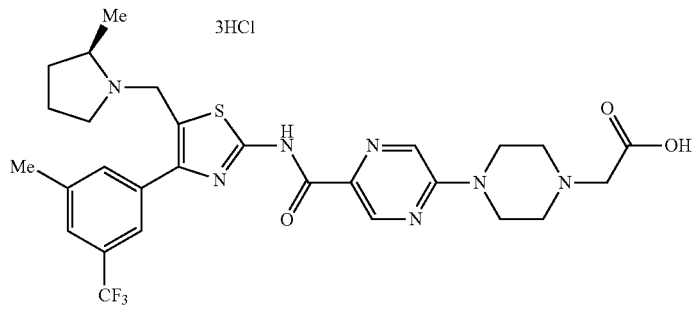 [SMILES: Cc1cc(-c2nc(NC(=O)c3cnc(N4CCN(CC(=O)O)CC4)cn3)sc2CN2CCC[C@H]2C)cc(C(F)(F)F)c1] |
| 72 | 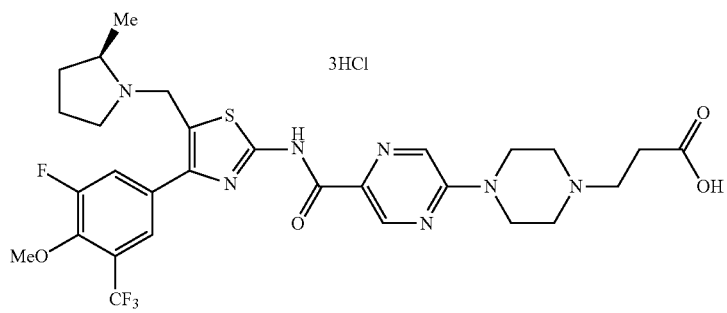 [SMILES: COc1c(F)cc(-c2nc(NC(=O)c3cnc(N4CCN(CCC(=O)O)CC4)cn3)sc2CN2CCC[C@H]2C)cc1C(F)(F)F] |
TABLE 89
| Ex | Structure |
|---|---|
| 73 | 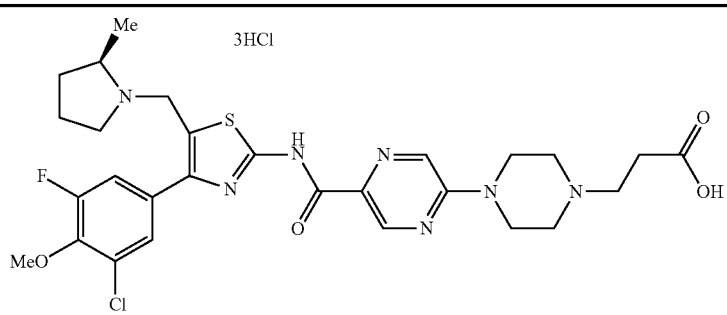 |
| 74 | 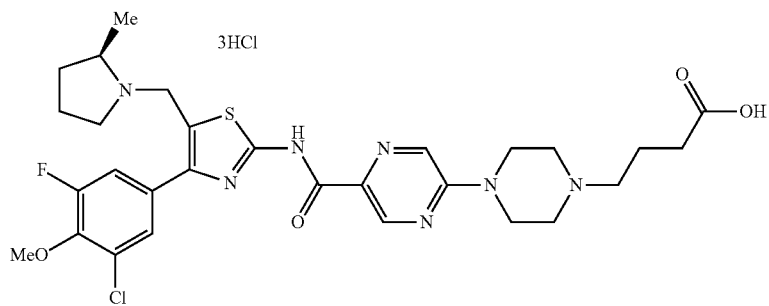 [SMILES: COc1c(F)cc(-c2nc(NC(=O)c3cnc(N4CCN(CCCC(=O)O)CC4)cn3)sc2CN2CCC[C@H]2C)cc1Cl] |

TABLE 89-continued
| Ex | Structure |
|---|---|
| 75 | 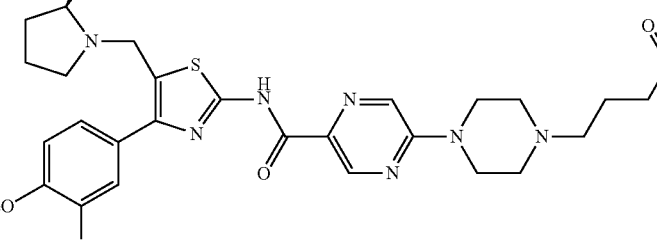 |
| 76 | 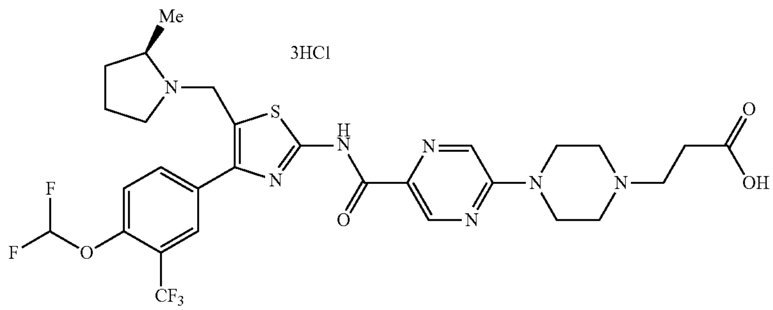 [SMILES: C[C@@H]1CCCN1Cc1sc(NC(=O)c2cnc(N3CCN(CCC(=O)O)CC3)cn2)nc1-c1ccc(OC(F)F)c(C(F)(F)F)c1] |
| 77 | 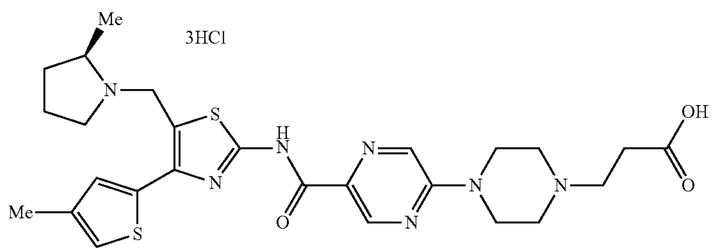 [SMILES: Cc1csc(-c2nc(NC(=O)c3cnc(N4CCN(CCC(=O)O)CC4)cn3)sc2CN2CCC[C@H]2C)c1] |
TABLE 90
| Ex | Structure |
|---|---|
| 78 | 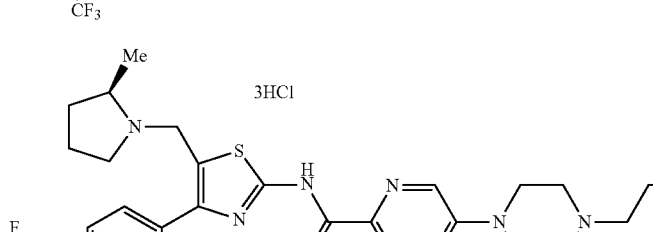 |
| 79 | 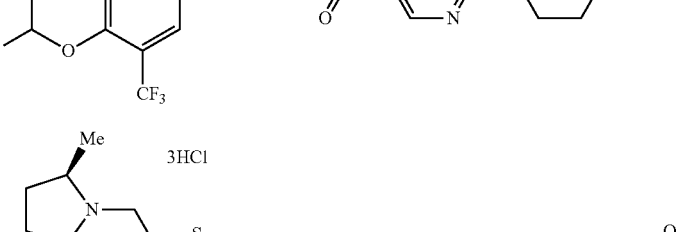 |

TABLE 90-continued
| Ex | Structure |
|---|---|
| 80 | 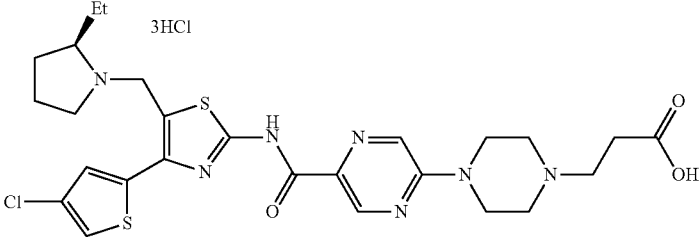 [SMILES: C[C@@H]1CCCN1Cc1sc(NC(=O)c2cnc(N3CCN(CCC(=O)O)CC3)cn2)nc1-c1cc(Cl)cs1] 3HCl |
| 81 | 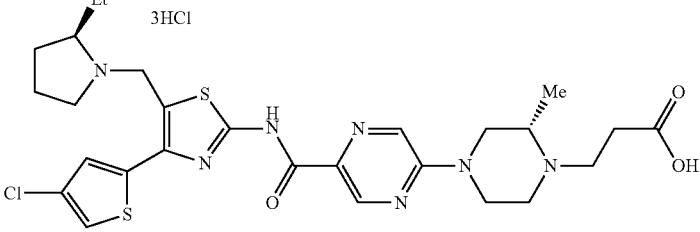 3HCl |
| 82 | 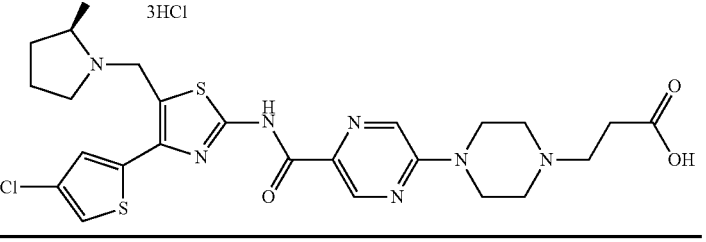 3HCl |
TABLE 91
| Ex | Structure |
|---|---|
| 83 | 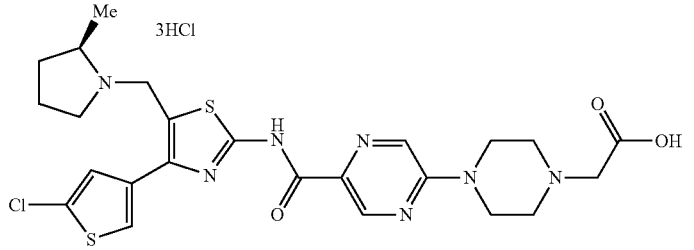 [SMILES: C[C@@H]1CCCN1Cc1sc(NC(=O)c2cnc(N3CCN(CC(=O)O)CC3)cn2)nc1-c1csc(Cl)c1] 3HCl |
| 84 | 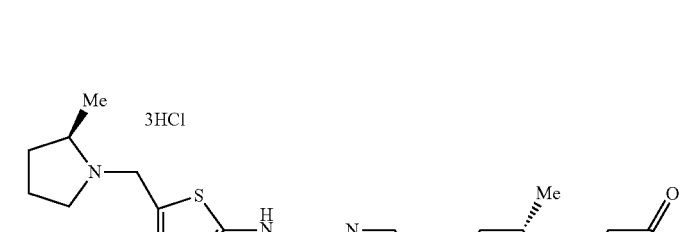 3HCl |

TABLE 91-continued
| Ex | Structure |
|---|---|
| 85 | 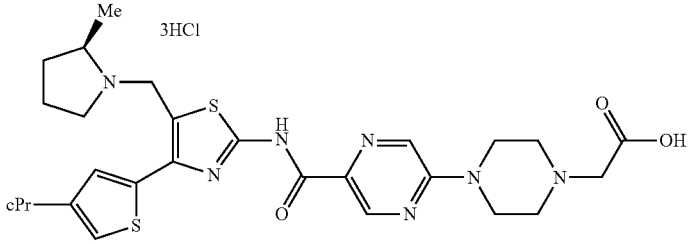 3HCl |
| 86 | 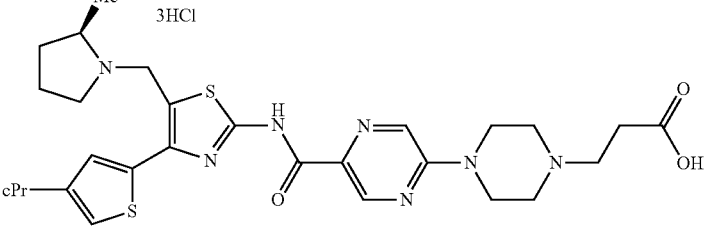 3HCl |
| 87 | 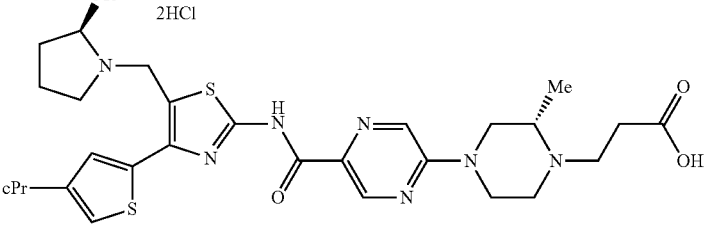 2HCl |
TABLE 92
| Ex | Structure |
|---|---|
| 88 | 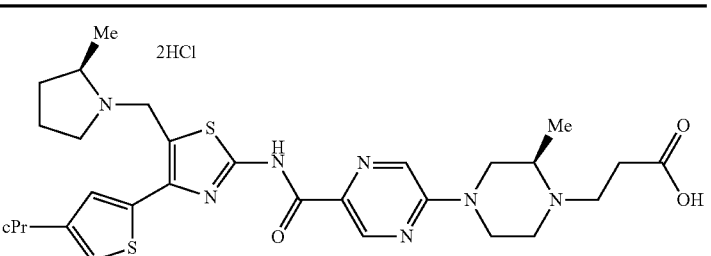 2HCl |
| 89 | 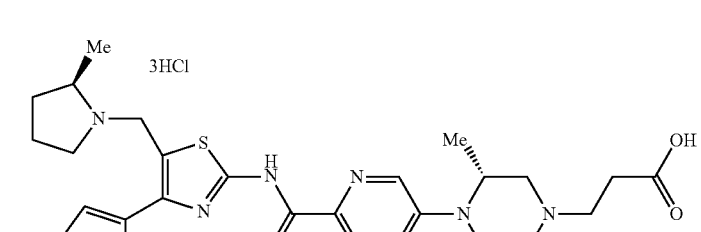 3HCl |

TABLE 92-continued

| Ex | Structure |
|---|---|
| 90 | (structure with (S)-2-methylpyrrolidine-CH2-thiazole bearing 4-cyclopropylthiophene, linked via amide to pyrazine-piperazine(3-Me)-CH2CH2COOH; 3HCl) |
| 91 | (structure with (S)-2-methylpyrrolidine-CH2-thiazole bearing 3-fluoro-4-methoxy-5-trifluoromethylphenyl, linked via amide to pyrazine-piperazine(3-Me)-CH2CH2COOH; 3HCl) |
| 92 | (structure with (S)-2-methylpyrrolidine-CH2-thiazole bearing 3-fluoro-4-methoxy-5-trifluoromethylphenyl, linked via amide to pyrazine-piperazine(3-Me, opposite stereochem)-CH2CH2COOH; 3HCl) |

TABLE 93

| Ex | Structure |
|---|---|
| 93 | (structure with (S)-2-methylpyrrolidine-CH2-thiazole bearing 3-fluoro-4-methoxy-5-trifluoromethylphenyl, linked via amide to pyrazine-piperazine-CH2COOH; 3HCl) |

TABLE 93-continued
| Ex | Structure |
|---|---|
| 94 | 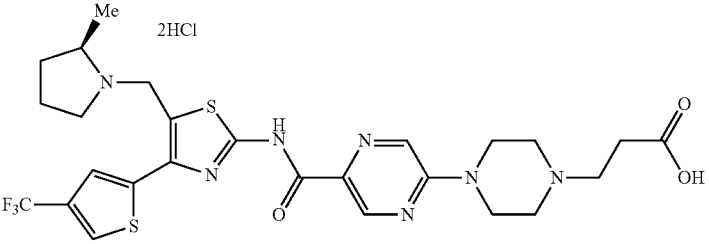 |
| 95 | 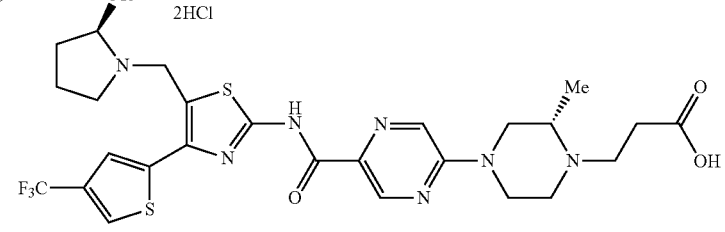 |
| 96 | 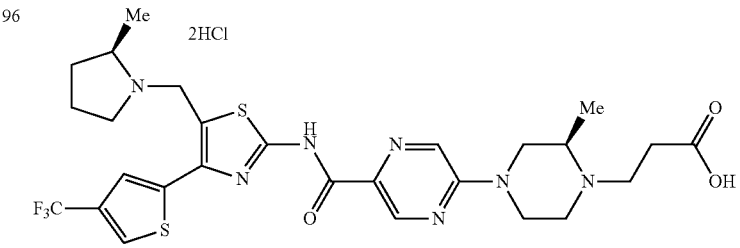 |
| 97 | 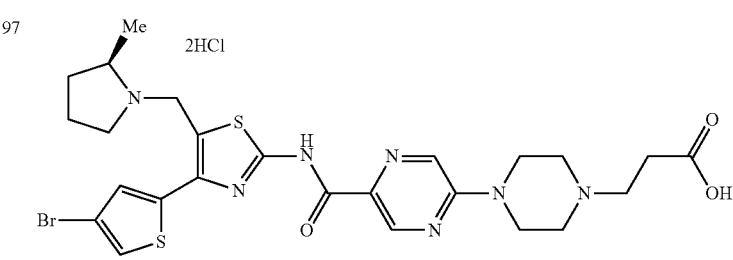 |
TABLE 94
| Ex | Structure |
|---|---|
| 98 | 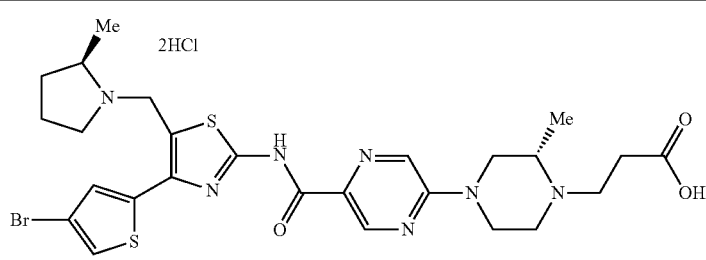 |

TABLE 94-continued
| Ex | Structure |
|---|---|
| 99 | 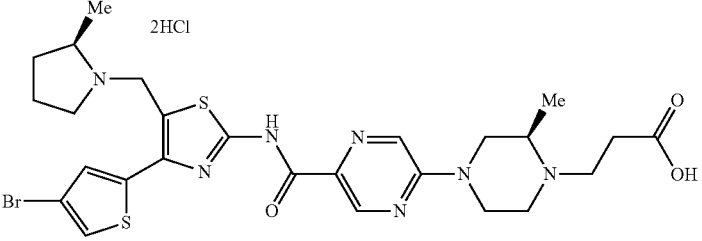 |
| 100 | 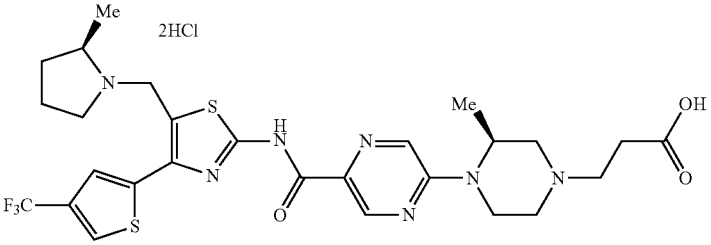 |
| 101 | 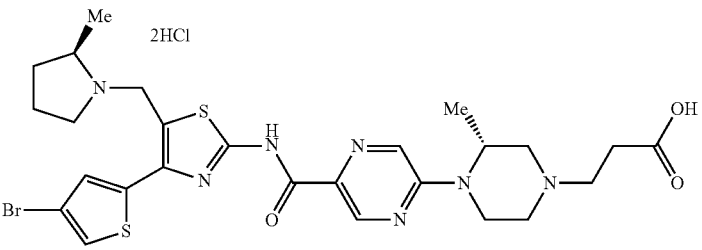 [SMILES: C[C@@H]1CCCN1Cc1sc(NC(=O)c2cnc(N3CCN(CCC(=O)O)C[C@H]3C)cn2)nc1-c1cc(Br)cs1] |
| 102 | 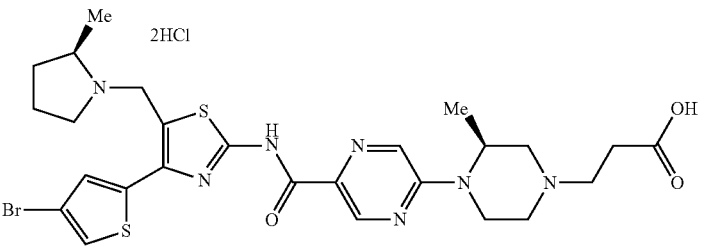 [SMILES: C[C@@H]1CCCN1Cc1sc(NC(=O)c2cnc(N3CCN(CCC(=O)O)C[C@@H]3C)cn2)nc1-c1cc(Br)cs1] |
TABLE 95
| Ex | Structure |
|---|---|
| 103 | 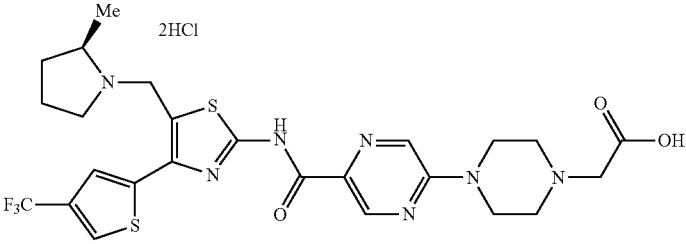 [SMILES: C[C@@H]1CCCN1Cc1sc(NC(=O)c2cnc(N3CCN(CC(=O)O)CC3)cn2)nc1-c1cc(C(F)(F)F)cs1] |

TABLE 95-continued
| Ex | Structure |
|---|---|
| 104 | 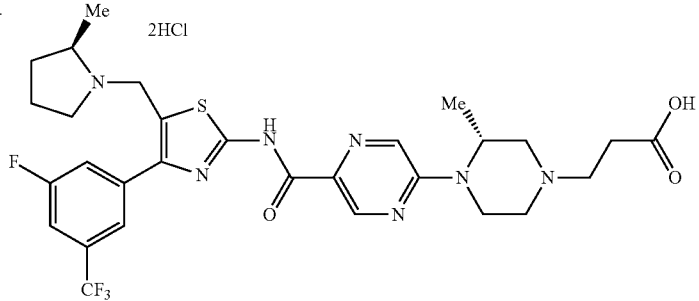 |
| 105 | 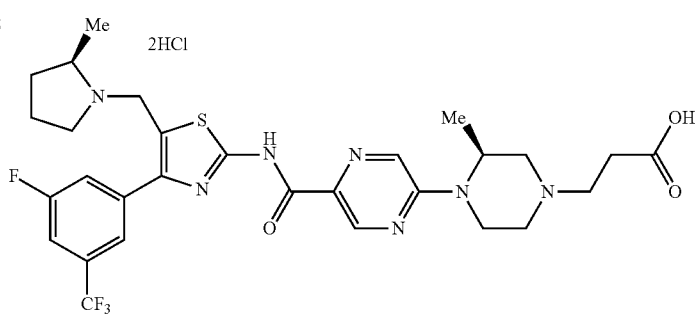 [SMILES: C[C@@H]1CCCN1Cc1sc(NC(=O)c2cnc(N3CCN(CCC(=O)O)C[C@H]3C)cn2)nc1-c1cc(F)cc(C(F)(F)F)c1] |
| 106 | 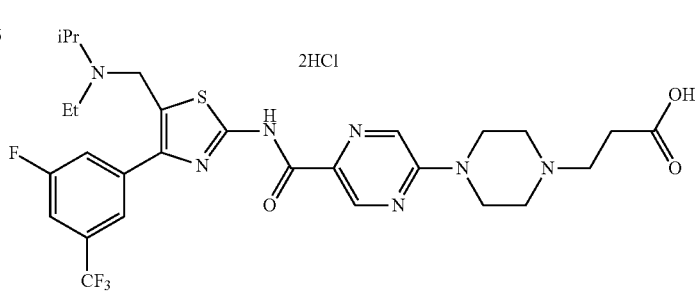 |
TABLE 96
| Ex | Structure |
|---|---|
| 107 | 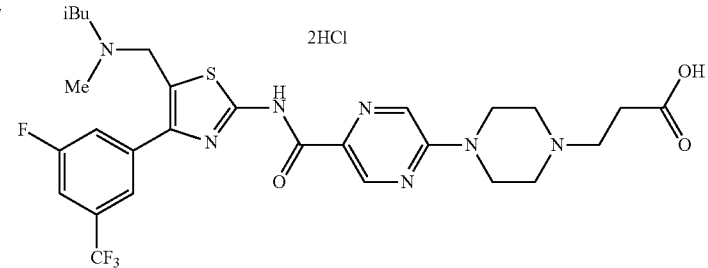 |

TABLE 96-continued

| Ex | Structure |
|---|---|
| 108 | (structure with cPr-N(Me)-CH2- thiazole bearing 3-fluoro-5-(trifluoromethyl)phenyl, linked via amide to pyrazine-piperazine-CH2CH2COOH; 2HCl) |
| 109 | (structure with Et2N-CH2- thiazole bearing 3-fluoro-5-(trifluoromethyl)phenyl, linked via amide to pyrazine-piperazine-CH2CH2COOH; 2HCl) |
| 110 | (structure with 2,5-dimethylpyrrolidin-1-ylmethyl thiazole bearing 3-fluoro-5-(trifluoromethyl)phenyl, linked via amide to pyrazine-piperazine-CH2CH2COOH; 2HCl) |
| 111 | (structure with 2,5-dimethylpyrrolidin-1-ylmethyl thiazole bearing 4-(trifluoromethyl)thiophen-2-yl, linked via amide to pyrazine-piperazine-CH2CH2COOH; 3HCl) |

TABLE 97

| Ex | Structure |
|---|---|
| 112 | (structure with 2-(trifluoromethyl)pyrrolidin-1-ylmethyl thiazole bearing 3-fluoro-5-(trifluoromethyl)phenyl, linked via amide to pyrazine-piperazine-CH2CH2COOH; 2HCl) |

TABLE 97-continued

| Ex | Structure |
|---|---|
| 113 | (structure with 2-CF3-pyrrolidine, thiazole, 3,5-bis-substituted phenyl (F, CF3), pyrazine carboxamide, (S)-3-methylpiperazine, propanoic acid; 2HCl) |
| 114 | (structure with (2R,5S)-2,5-dimethylpyrrolidine, thiazole, 5-chlorothiophen-3-yl, pyrazine carboxamide, piperazine, propanoic acid; 2HCl) |
| 115 | (structure with 2,5-dimethylpyrrolidine, thiazole, 5-chlorothiophen-3-yl, pyrazine carboxamide, 3-methylpiperazine, propanoic acid; 2HCl) |

TABLE 98

| Ex | Structure |
|---|---|
| 116 | (structure with (2R,5S)-2,5-dimethylpyrrolidine, thiazole, 5-chlorothiophen-3-yl, pyrazine carboxamide, (S)-3-methylpiperazine, propanoic acid; 2HCl) |
| 117 | (structure with (2R,5S)-2,5-dimethylpyrrolidine, thiazole, 5-chlorothiophen-3-yl, pyrazine carboxamide, (R)-3-methylpiperazine, propanoic acid; 3HCl) |

TABLE 98-continued
| Ex | Structure |
|---|---|
| 118 | 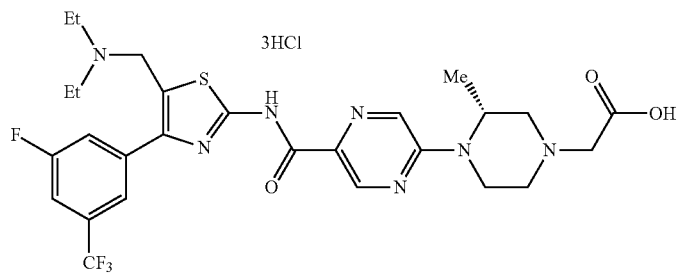 [SMILES: CCN(CC)Cc1sc(NC(=O)c2cnc(N3CCN(CC(=O)O)C[C@H]3C)cn2)nc1-c1cc(F)cc(C(F)(F)F)c1] |
| 119 | 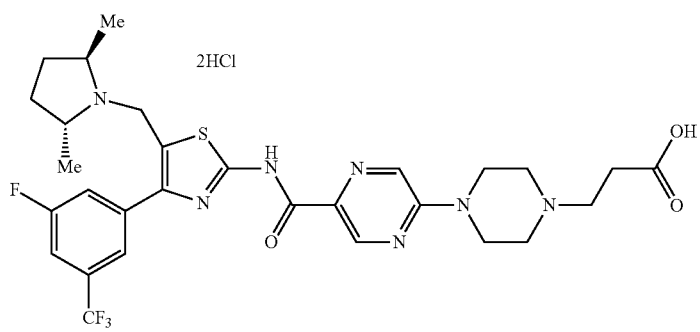 [SMILES: C[C@@H]1CC[C@@H](C)N1Cc1sc(NC(=O)c2cnc(N3CCN(CCC(=O)O)CC3)cn2)nc1-c1cc(F)cc(C(F)(F)F)c1] |
TABLE 99
| Ex | Structure |
|---|---|
| 120 | 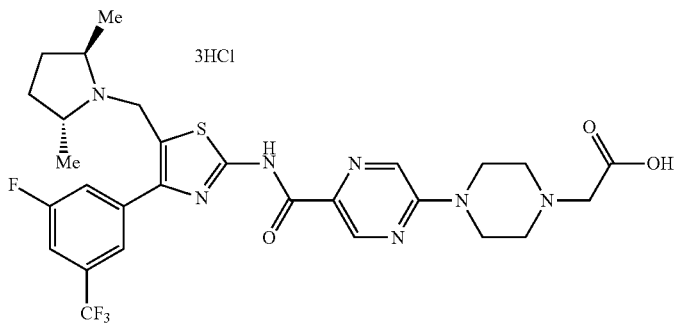 [SMILES: C[C@@H]1CC[C@@H](C)N1Cc1sc(NC(=O)c2cnc(N3CCN(CC(=O)O)CC3)cn2)nc1-c1cc(F)cc(C(F)(F)F)c1] |
| 121 | 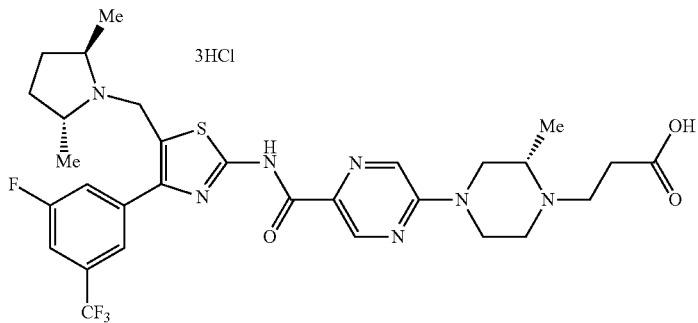 [SMILES: C[C@@H]1CC[C@@H](C)N1Cc1sc(NC(=O)c2cnc(N3CCN(CCC(=O)O)[C@@H](C)C3)cn2)nc1-c1cc(F)cc(C(F)(F)F)c1] |

TABLE 99-continued
| Ex | Structure |
|---|---|
| 122 | 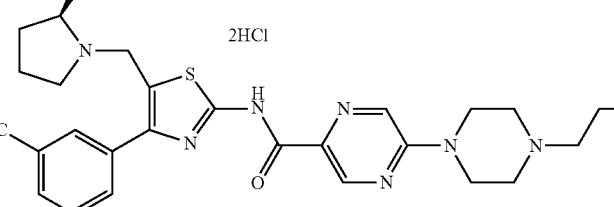 |
| 123 | 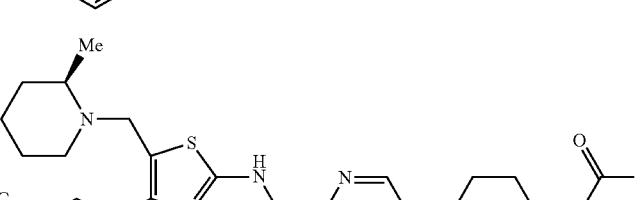 |
| 124 | 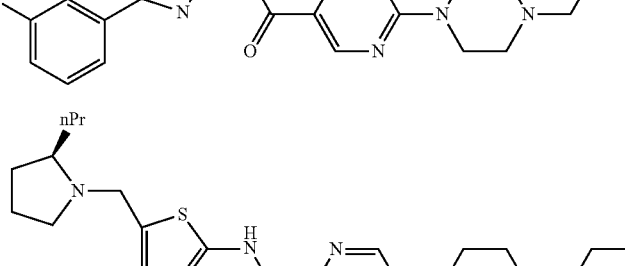 |
TABLE 100
| Ex | Structure |
|---|---|
| 125 | 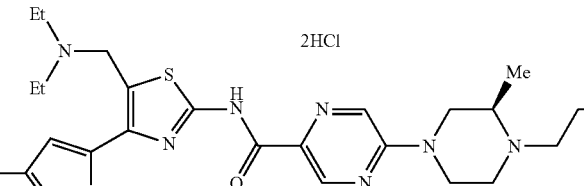 |
| 126 | 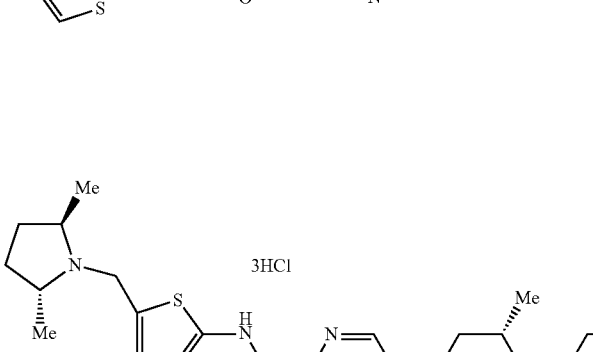 |

TABLE 100-continued

| Ex | Structure |
|---|---|
| 127 | (iPr)(Me)N-CH2-[thiazole with 4-(4-chlorothiophen-2-yl)]-NH-C(O)-[pyrazine]-[(S)-3-methylpiperazine]-CH2CH2-C(O)OH · 3HCl |
| 128 | (cPr-CH2)(Me)N-CH2-[thiazole with 4-(4-chlorothiophen-2-yl)]-NH-C(O)-[pyrazine]-[(S)-3-methylpiperazine]-CH2CH2-C(O)OH · 3HCl |
| 129 | (iPr)(Et)N-CH2-[thiazole with 4-(4-chlorothiophen-2-yl)]-NH-C(O)-[pyrazine]-[(S)-3-methylpiperazine]-CH2CH2-C(O)OH · 3HCl |
| 130 | (cPr-CH2)(Me)N-CH2-[thiazole with 4-(4-chlorothiophen-2-yl)]-NH-C(O)-[pyrazine]-[(S)-3-methylpiperazine]-CH2CH2-C(O)OH · 3HCl |

TABLE 101

| Ex | Structure |
|---|---|
| 131 | [(S)-2-methylpyrrolidin-1-yl]-CH2-[thiazole with 4-(4,5-dichlorothiophen-2-yl)]-NH-C(O)-[pyrazine]-[piperazine]-CH2CH2-C(O)OH · 3HCl |

TABLE 101-continued
| Ex | Structure |
|---|---|
| 132 | 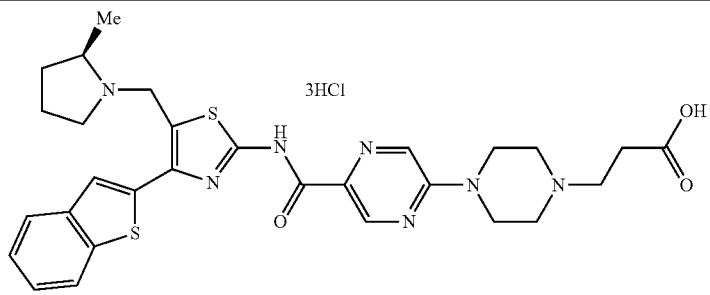 |
| 133 | 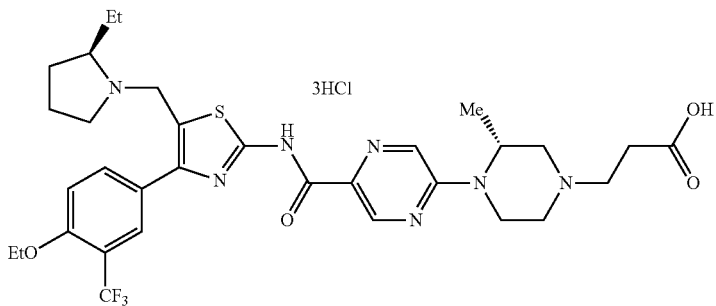 [SMILES: CCOc1ccc(-c2nc(NC(=O)c3cnc(N4CCN(CCC(=O)O)C[C@H]4C)cn3)sc2CN2CCC[C@H]2CC)cc1C(F)(F)F] |
| 134 | 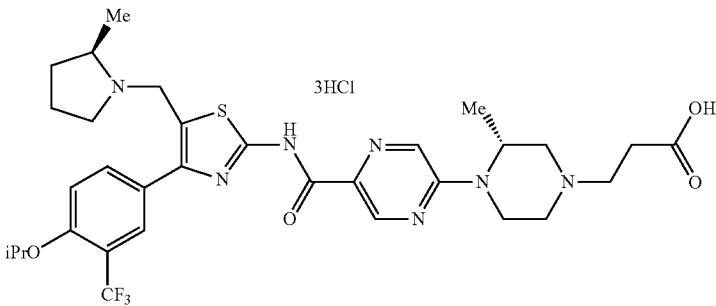 [SMILES: CC[C@@H]1CCCN1Cc1sc(NC(=O)c2cnc(N3CCN(CCC(=O)O)C[C@H]3C)cn2)nc1-c1ccc(OC(C)C)c(C(F)(F)F)c1] |
TABLE 102
| Ex | Structure |
|---|---|
| 135 | 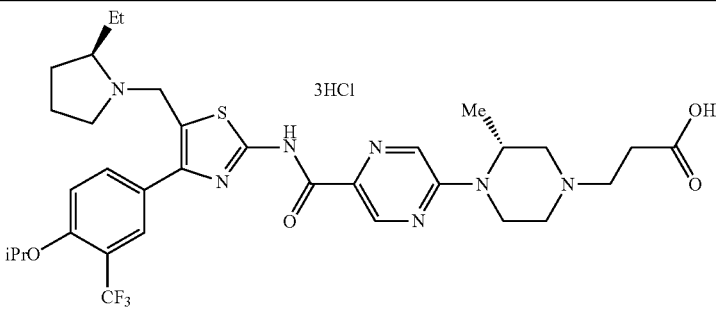 |

TABLE 102-continued
| Ex | Structure |
|---|---|
| 136 | 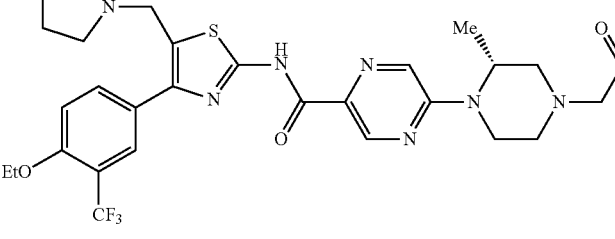 |
| 137 | 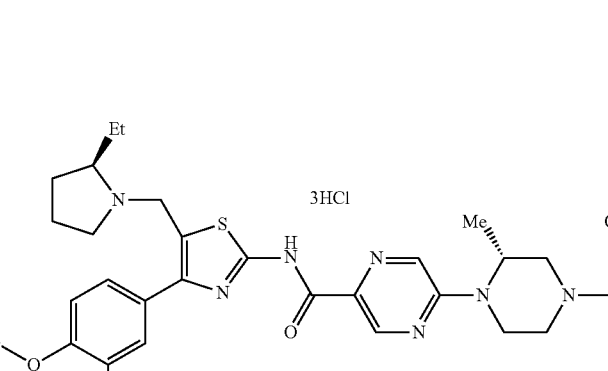 |
| 138 | 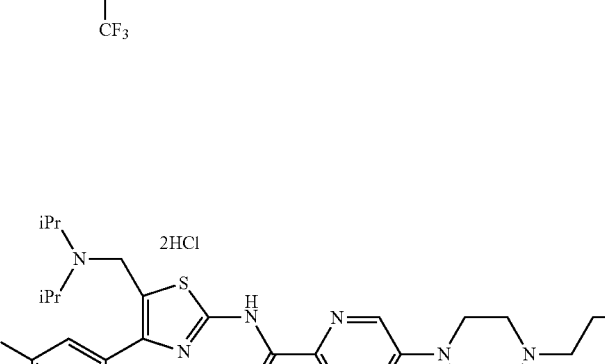 |
TABLE 103
| Ex | Structure |
|---|---|
| 139 | 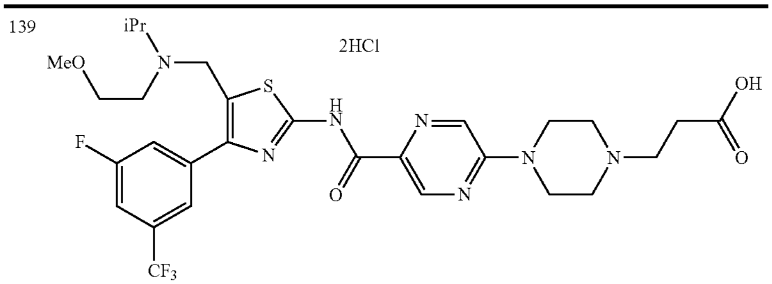 |

TABLE 103-continued
| Ex | Structure |
|---|---|
| 140 | 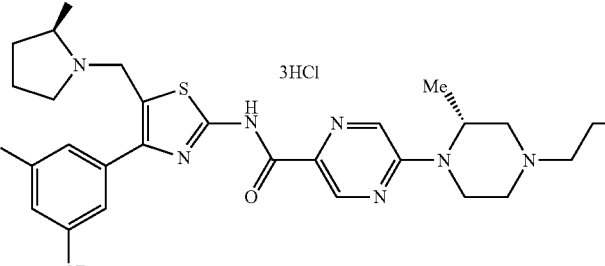 |
| 141 | 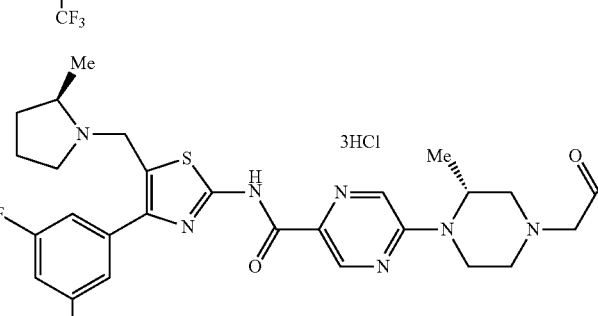 |
| 142 | 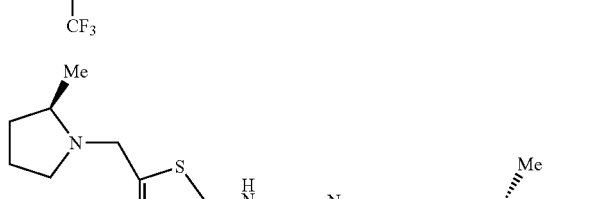 |
TABLE 104
| Ex | Structure |
|---|---|
| 143 | 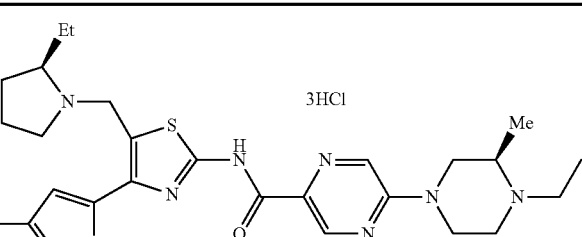 |
| 144 | 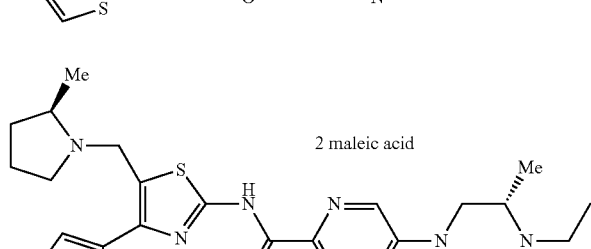 |

TABLE 105

| Ex. | Syn. | Data |
|---|---|---|
| 1 | Ex1 | ESI+: 590, 592<br>NMR-DMSO-d6: 1.20-1.52 (6H, m), 1.60-1.81 (1H, m), 1.85-2.03 (2H, m), 2.15-2.29 (1H, m), 2.77-3.00 (2H, m), 3.09-3.75 (9H, m), 3.75-4.77 (5H, m), 4.84-4.97 (1H, m), 7.65-7.71 (1H, m), 7.74 (1H, d, J = 1.3 Hz), 8.48-8.56 (1H, m), 8.79-8.85 (1H, m), 10.60-11.20 (1H, m), 11.45-11.84 (1H, m), 12.20-12.38 (1H, m) |
| 2 | Ex2 | ESI+: 657 |
| 3 | Ex3 | ESI+: 624<br>NMR-DMSO-d6: 1.40-1.54 (6H, m), 1.61-1.75 (1H, m), 1.84-2.04 (2H, m), 2.16-2.28 (1H, m), 2.84-3.12 (3H, m), 3.16-3.30 (3H, m), 3.46-3.62 (6H, m), 4.55-4.72 (2H, m), 4.94 (1H, d, J = 15 Hz), 5.05 (1H, brs), 7.95 (1H, s), 8.40 (1H, t, J = 1 Hz), 8.47 (1H, s), 8.85 (1H, d, J = 1 Hz), 10.6 (1H, brs), 11.1 (1H, brs), 12.4 (1H, s), 12.7 (1H, brs) |
| 4 | Ex4 | ESI+: 632 |
| 5 | Ex5 | ESI–: 548, 550 [M – H]– |
| 6 | Ex6 | ESI+: 570 |
| 7 | Ex7 | ESI+: 662 |
| 8 | Ex8 | ESI+: 648 |
| 9 | Ex9 | ESI+: 624<br>NMR-DMSO-d6: 1.05-1.15 (6H, m), 1.20-1.52 (3H, m), 2.75-4.20 (14H, m), 4.40-4.80 (4H, m), 7.80-7.87 (1H, m), 7.88-7.96 (2H, m), 8.53 (1H, s), 8.84 (1H, s), 10.63 (1H, brs), 11.33-11.76 (1H, m), 12.30-12.42 (1H, m) |
| 10 | Ex1 | ESI+: 648 |
| 11 | Ex1 | ESI+: 638, 640 |
| 12 | Ex1 | ESI+: 638, 640 |
| 13 | Ex1 | ESI+: 624 |
| 14 | Ex1 | ESI+: 624 |
| 15 | Ex1 | ESI+: 638 |
| 16 | Ex1 | ESI+: 638, 640 |
| 17 | Ex1 | ESI+: 636 |
| 18 | Ex1 | ESI+: 662 |
| 19 | Ex1 | ESI+: 590 |
| 20 | Ex1 | ESI+: 590, 592 |
| 21 | Ex1 | ESI+: 636 |

TABLE 106

| Ex. | Syn. | Data |
|---|---|---|
| 22 | Ex1 | ESI+: 576, 578<br>NMR-DMSO-d6: 1.34-1.50 (6H, m), 1.62-1.73 (1H, m), 1.84-2.02 (2H, m), 2.17-2.28 (1H, m), 2.92-4.27 (13H, m), 4.55-4.69 (2H, m), 4.87-4.96 (1H, m), 5.04 (1H, brs), 7.68 (1H, d, J = 1.4 Hz), 7.74 (1H, d, J = 1.4 Hz), 8.43 (1H, s), 8.84 (1H, d, J = 1.2 Hz), 10.57 (1H, brs), 12.32 (1H, s) |
| 23 | Ex1 | ESI+: 662 |
| 24 | Ex1 | ESI+: 576, 578 |
| 25 | Ex1 | ESI+: 590 |
| 26 | Ex1 | ESI+: 576 |
| 27 | Ex1 | ESI+: 682, 684 |
| 28 | Ex1 | ESI+: 604<br>NMR-DMSO-d6: 0.89 (3H, t, J = 7.3 Hz), 1.47 (3H, d, J = 7.1 Hz), 1.60-1.74 (2H, m), 1.83-2.01 (3H, m), 2.16-2.26 (1H, m), 2.85-3.91 (14H, m), 4.58-4.77 (2H, m), 4.87-4.96 (1H, m), 5.02-5.11 (1H, m), 7.70 (1H, d, J = 1.3 Hz), 7.74 (1H, d, J = 1.3 Hz), 8.47 (1H, s), 8.84 (1H, d, J = 1.1 Hz), 10.59 (1H, brs), 11.11 (1H, brs), 12.32 (1H, s) |
| 29 | Ex1 | ESI+: 604 |
| 30 | Ex1 | ESI+: 636<br>NMR-DMSO-d6: 1.36 (3H, d, J = 6.4 Hz), 1.44 (3H, d, J = 7.1 Hz), 1.59-1.69 (1H, m), 1.85-1.96 (2H, m), 2.14-2.22 (1H, m), 2.87-3.20 (4H, m), 3.20-3.74 (9H, m), 4.47-4.53 (1H, m), 4.61-4.69 (1H, m), 4.79-4.85 (1H, m), 5.03-5.10 (1H, m), 7.80-7.85 (1H, m), 7.91-7.96 (2H, m), 8.47 (1H, s), 8.86 (1H, d, J = 1.2 Hz), 10.48 (1H, brs), 10.76 (1H, brs), 12.34-12.38 (1H, m) |
| 31 | Ex1 | ESI+: 604<br>NMR-DMSO-d6: 0.89 (3H, t, J = 7.4 Hz), 1.18-1.52 (3H, m), 1.58-1.75 (2H, m), 1.81-2.02 (3H, m), 2.14-2.27 (1H, m), 2.78-2.95 (2H, m), 3.07-3.98 (10H, m), 4.37-4.78 (3H, m), 4.85-4.98 (1H, m), 7.69 (1H, s), 7.74 (1H, d, J = 1.2 Hz), 8.52 (1H, s), 8.80-8.84 (1H, m), 10.59 (1H, brs), 11.29-11.79 (1H, m), 12.32 (1H, s), 12.50-13.07 (1H, m) |

TABLE 107

| Ex. | Syn. | Data |
|---|---|---|
| 32 | Ex1 | ESI+: 622<br>NMR-DMSO-d6: 1.14-1.51 (6H, m), 1.61-1.78 (1H, m), 1.83-2.00 (2H, m), 2.11-2.24 (1H, m), 3.00-4.30 (12H, m), 4.48 (1H, dd, J = 7.4, 14.8 Hz), 4.64 (1H, d, J = 14.0 Hz), 4.76 (1H, d, J = 14.5 Hz), 5.07 (1H, brs), 7.77-7.83 (1H, m), 7.90-8.04 (2H, m), 8.41-8.48 (1H, m), 8.85 (1H, d, J = 1.3 Hz), 11.05-11.60 (1H, m), 12.28-12.42 (1H, m) |
| 33 | Ex1 | ESI+: 635<br>NMR-DMSO-d6: 1.36 (3H, d, J = 6.3 Hz), 1.59-1.69 (1H, m), 1.83-1.97 (2H, m), 2.13-2.22 (1H, m), 2.85-2.89 (2H, m), 3.03-3.78 (11H, m), 4.07 (3H, s), 4.39-4.87 (4H, m), 8.38-8.41 (1H, m), 8.49-8.52 (1H, m), 8.75-8.80 (1H, m), 8.84 (1H, d, J = 1.3 Hz), 10.50 (1H, brs), 10.76-11.73 (1H, m), 12.34 (1H, s), 12.40-12.90 (1H, br) |
| 34 | Ex2 | ESI+: 629 |
| 35 | Ex2 | ESI+: 671 |
| 36 | Ex2 | ESI+: 671 |
| 37 | Ex2 | ESI+: 671 |
| 38 | Ex2 | ESI+: 657 |
| 39 | Ex2 | ESI+: 643 |
| 40 | Ex2 | ESI+: 643 |
| 41 | Ex3 | ESI+: 634 |
| 42 | Ex3 | ESI–: 646 [M – H]– |
| 43 | Ex3 | ESI+: 634, 636 |
| 44 | Ex3 | ESI+: 634 |
| 45 | Ex3 | ESI+: 620, 622 |
| 46 | Ex3 | ESI+: 634 |
| 47 | Ex3 | ESI+: 620 |
| 48 | Ex3 | ESI+: 634 |
| 49 | Ex3 | ESI+: 622<br>NMR-DMSO-d6: 1.34-1.40 (3H, m), 1.58-1.76 (1H, m), 1.83-1.97 (2H, m), 2.11-2.23 (1H, m), 2.90 (2H, t, J = 7.6 Hz), 3.03-3.97 (13H, m), 4.42-4.56 (1H, m), 4.60-4.87 (3H, m), 7.79-7.85 (1H, m), 7.91-8.00 (2H, m), 8.51 (1H, d, J = 1.2 Hz), 8.85 (1H, d, J = 1.3 Hz), 10.75 (1H, brs), 11.05-11.45 (1H, m), 12.33-12.41 (1H, m) |

TABLE 108

| Ex. | Syn. | Data |
|---|---|---|
| 50 | Ex3 | ESI+: 576, 578<br>NMR-DMSO-d6: 1.44 (3H, d, J = 6.5 Hz), 1.62-1.73 (1H, m), 1.84-2.02 (2H, m), 2.17-2.28 (1H, m), 2.90 (2H, t, J = 7.7 Hz), 3.08-3.23 (3H, m), 3.30-3.39 (2H, m), 3.42-4.07 (8H, m), 4.56-4.77 (3H, m), 4.88-4.96 (1H, m), 7.68 (1H, d, J = 1.4 Hz), 7.74 (1H, d, J = 1.4 Hz), 8.51 (1H, d, J = 1.2 Hz), 8.83 (1H, d, J = 1.2 Hz), 10.45-11.00 (1H, m), 11.44 (1H, brs), 12.26-12.43 (1H, m) |
| 51 | Ex3 | ESI+: 562 |
| 52 | Ex3 | ESI+: 634 |
| 53 | Ex3 | ESI+: 620 |
| 54 | Ex3 | ESI+: 648 |
| 55 | Ex3 | ESI+: 662 |
| 56 | Ex3 | ESI+: 662 |
| 57 | Ex3 | ESI+: 662 |
| 58 | Ex3 | ESI+: 676 |
| 59 | Ex3 | ESI+: 676 |
| 60 | Ex3 | ESI+: 622 |
| 61 | Ex3 | ESI+: 608 |
| 62 | Ex3 | ESI+: 622 |
| 63 | Ex3 | ESI+: 644 |
| 64 | Ex3 | ESI+: 622 |
| 65 | Ex3 | ESI+: 618 |
| 66 | Ex3 | ESI+: 604 |
| 67 | Ex3 | ESI+: 644 |

TABLE 108-continued

| Ex. | Syn. | Data |
|---|---|---|
| 68 | Ex3 | ESI+: 630 |
| 69 | Ex3 | ESI+: 658 |
| 70 | Ex3 | ESI+: 644 |
| 71 | Ex3 | ESI+: 604 |
| 72 | Ex3 | ESI+: 652 |
| 73 | Ex3 | ESI+: 618 |
| 74 | Ex3 | ESI+: 632, 634 |
| 75 | Ex3 | ESI+: 662 |
| 76 | Ex3 | ESI+: 670 |
| 77 | Ex3 | ESI+: 556 |
| 78 | Ex3 | ESI+: 570 |

TABLE 109

| Ex. | Syn. | Data |
|---|---|---|
| 79 | Ex3 | ESI+: 590 |
| 80 | Ex3 | ESI+: 590, 592<br>NMR-DMSO-d6: 0.89 (3H, t, J = 7.4 Hz), 1.58-1.72 (2H, m), 1.82-2.02 (3H, m), 2.16-2.27 (1H, m), 2.89 (2H, t, J = 7.6 Hz), 3.06-3.70 (13H, m), 4.60-4.78 (3H, m), 4.89-4.98 (1H, m), 7.69 (1H, d, J = 1.3 Hz), 7.74 (1H, d, J = 1.4 Hz), 8.51 (1H, d, J = 1.2 Hz), 8.84 (1H, d, J = 1.3 Hz), 10.43 (1H, brs), 11.30 (1H, brs), 12.35 (1H, s) |
| 81 | Ex3 | ESI+: 604, 606 |
| 82 | Ex3 | ESI+: 576 |
| 83 | Ex3 | ESI+: 562 |
| 84 | Ex3 | ESI+: 590 |
| 85 | Ex3 | ESI+: 568 |
| 86 | Ex3 | ESI+: 582 |
| 87 | Ex3 | ESI+: 596 |
| 88 | Ex3 | ESI+: 596 |
| 89 | Ex3 | ESI+: 596 |
| 90 | Ex3 | ESI+: 596 |
| 91 | Ex3 | ESI+: 666 |
| 92 | Ex3 | ESI+: 666 |
| 93 | Ex3 | ESI+: 638 |
| 94 | Ex3 | ESI+: 610 |
| 95 | Ex3 | ESI+: 624 |
| 96 | Ex3 | ESI+: 624 |
| 97 | Ex3 | ESI+: 620, 622 |
| 98 | Ex3 | ESI+: 636, 638 |
| 99 | Ex3 | ESI+: 634, 636 |
| 100 | Ex3 | ESI+: 624 |
| 101 | Ex3 | ESI+: 634 |
| 102 | Ex3 | ESI+: 634 |
| 103 | Ex3 | ESI+: 596 |
| 104 | Ex3 | ESI+: 650 |
| 105 | Ex3 | ESI+: 650 |
| 106 | Ex3 | ESI+: 624 |

TABLE 110

| Ex. | Syn. | Data |
|---|---|---|
| 107 | Ex3 | ESI+: 624<br>NMR-DMSO-d6: 0.85 (3H, d, J = 6.6 Hz), 0.90 (3H, d, J = 6.5 Hz), 1.90-2.00 (1H, m), 2.60-2.71 (3H, m), 2.71-2.81 (2H, m), 2.91 (2H, t, J = 7.7 Hz), 3.05-3.25 (2H, m), 3.28-3.38 (2H, m), 3.49-3.67 (4H, m), 3.80-4.82 (5H, m), 7.82-7.90 (3H, m), 8.51 (1H, d, J = 1.2 Hz), 8.85 (1H, d, J = 1.3 Hz), 10.25 (1H, brs), 11.62 (1H, brs), 12.36 (1H, s) |
| 108 | Ex3 | ESI+: 622 |
| 109 | Ex9 | ESI+: 610 |
| 110 | Ex3 | ESI+: 636 |
| 111 | Ex3 | ESI+: 624<br>NMR-DMSO-d6: 1.27 (3H, d, J = 6.8 Hz), 1.42 (3H, d, J = 6.5 Hz), 1.55-1.80 (2H, m), 2.12-2.34 (2H, m), 2.92 (2H, t, J = 7.7 Hz), 3.05-3.25 (2H, m), 3.25-3.40 (2H, m), 3.48-3.79 (5H, m), 3.82-3.97 (1H, m), 4.51 (1H, dd, J = 7.2, 15.3 Hz), 4.59-4.83 (3H, m), 4.90-6.65 (2H, m), 7.96-7.99 (1H, m), 8.39-8.42 (1H, m), 8.49-8.53 (1H, m), 8.84 (1H, d, J = 1.3 Hz), 10.99 (1H, brs), 11.75 (1H, brs), 12.37 (1H, s) |
| 112 | Ex3 | ESI+: 676 |
| 113 | Ex3 | ESI+: 690 |
| 114 | Ex3 | ESI−: 588, 590 [M − H]− |
| 115 | Ex3 | ESI−: 602, 604 [M − H]− |
| 116 | Ex3 | ESI−: 602, 604 [M − H]− |
| 117 | Ex3 | ESI−: 602, 604 [M − H]− |
| 118 | Ex9 | ESI+: 610<br>NMR-DMSO-d6: 1.06-1.14 (6H, m), 1.43 (3H, d, J = 6.8 Hz), 2.92-3.15 (4H, m), 3.16-3.45 (2H, m), 3.51-3.75 (4H, m), 3.80-4.84 (6H, m), 4.97-5.24 (1H, m), 7.80-7.86 (1H, m), 7.87-7.97 (2H, m), 8.42-8.48 (1H, m), 8.86 (1H, d, J = 1.2 Hz), 10.00-11.50 (2H, m), 12.37 (1H, s) |
| 119 | Ex3 | ESI+: 636<br>NMR-DMSO-d6: 1.21 (3H, d, J = 6.8 Hz), 1.40 (3H, d, J = 6.5 Hz), 1.60-1.71 (2H, m), 2.17-2.30 (2H, m), 2.91 (2H, t, J = 7.7 Hz), 3.08-3.25 (2H, m), 3.29-3.37 (2H, m), 3.50-3.70 (4H, m), 3.87-3.98 (1H, m), 4.38 (1H, dd, J = 7.5, 15.3 Hz), 4.50-6.00 (5H, m), 7.79-7.85 (1H, m), 7.94-8.00 (2H, m), 8.51 (1H, d, J = 1.2 Hz), 8.85 (1H, d, J = 1.3 Hz), 11.08 (1H, brs), 11.63 (1H, brs), 12.37 (1H, s) |

TABLE 111

| Ex. | Syn. | Data |
|---|---|---|
| 120 | Ex3 | ESI+: 622<br>NMR-DMSO-d6: 1.22 (3H, d, J = 6.8 Hz), 1.41 (3H, d, J = 6.5 Hz), 1.57-1.75 (2H, m), 2.12-2.33 (2H, m), 3.11-4.03 (7H, m), 4.20 (2H, s), 4.25-5.21 (7H, m), 7.78-7.85 (1H, m), 7.95-8.03 (2H, m), 8.50 (1H, d, J = 1.2 Hz), 8.85 (1H, d, J = 1.3 Hz), 10.60-11.70 (2H, m), 12.38 (1H, s) |
| 121 | Ex3 | ESI+: 650 |
| 122 | Ex3 | ESI+: 632 |
| 123 | Ex4 | ESI+: 604 |
| 124 | Ex4 | ESI+: 632 |
| 125 | Ex5 | ESI−: 576, 578 [M − H]− |
| 126 | Ex5 | ESI−: 602, 604 [M − H]− |
| 127 | Ex5 | ESI−: 576, 578 [M − H]− |
| 128 | Ex5 | ESI−: 588, 590 [M − H]− |
| 129 | Ex5 | ESI−: 576, 578 [M − H]− |
| 130 | Ex5 | ESI−: 588, 590 [M − H]−<br>NMR-DMSO-d6: 0.33-0.54 (2H, m), 0.60-0.72 (2H, m), 1.13-1.50 (4H, m), 2.75-2.81 (3H, m), 2.81-3.07 (3H, m), 3.11-3.74 (7H, m), 3.74-4.94 (7H, m), 7.68 (1H, d, J = 1.4 Hz), 7.74 (1H, d, J = 1.4 Hz), 8.47-8.57 (1H, m), 8.78-8.86 (1H, m), 10.58 (1H, brs), 11.33-11.77 (1H, m), 12.22-12.42 (1H, m) |
| 131 | Ex6 | ESI+: 610, 612 |
| 132 | Ex6 | ESI+: 592 |
| 133 | Ex7 | ESI+: 676 |
| 134 | Ex7 | ESI+: 676 |
| 135 | Ex7 | ESI+: 690 |
| 136 | Ex8 | ESI+: 662 |
| 137 | Ex8 | ESI+: 676 |
| 138 | Ex9 | ESI+: 638 |
| 139 | Ex9 | ESI+: 654 |
| 140 | Ex1 | ESI+: 636 [M + H]+<br>NMR-DMSO-d6: 1.34-1.41 (3H, m), 1.47 (3H, d, J = 7.0 Hz), 1.60-1.74 (1H, m), 1.86-1.97 (2H, m), 2.11-2.23 (1H, m), 2.81-4.17 (15H, m), 4.43-4.54 (1H, m), 4.61-4.71 (1H, m), 4.75-4.84 (1H, m), 5.01-5.12 (1H, m), 7.79-7.84 (1H, m), 7.91-8.00 (2H, m), 8.45-8.49 (1H, m), 8.85 (1H, d, J = 1.2 Hz), 10.85 (1H, brs), 10.95-11.31 (1H, m), 12.30-12.41 (1H, m) |

TABLE 112

| Ex. | Syn. | Data |
|---|---|---|
| 141 | Ex1 | ESI+: 622 [M + H]+<br>NMR-DMSO-d6: 1.34-1.47 (6H, m), 1.60-1.74 (1H, m), 1.86-1.97 (2H, m), 2.11-2.23 (1H, m), 3.10-4.29 |

TABLE 112-continued

| Ex. | Syn. | Data |
|---|---|---|
| | | (13H, m), 4.42-4.54 (1H, m), 4.57-4.72 (1H, m), 4.74-4.83 (1H, m), 5.09 (1H, brs), 7.78-7.85 (1H, m), 7.91-8.02 (2H, m), 8.45 (1H, s), 8.86 (1H, d, J = 1.3 Hz), 10.75-11.42 (1H, m), 12.32-12.41 (1H, m) |
| 142 | Ex3 | ESI+: 590, 592 [M + H]+<br>NMR-DMSO-d6: 1.21-1.31 (1H, m), 1.35-1.49 (6H, m), 1.61-1.74 (1H, m), 1.84-2.02 (2H, m), 2.13-2.29 (1H, m), 2.79-2.98 (2H, m), 3.10-3.98 (10H, m), 4.40-4.77 (3H, m), 4.87-4.98 (1H, m), 7.67 (1H, d, J = 1.3 Hz), 7.74 (1H, d, J = 1.3 Hz), 8.52 (1H, s), 8.82 (1H, s), 10.39-10.97 (1H, m), 11.25-11.65 (1H, m), 12.25-12.42 (1H, m), 12.56-13.02 (1H, br) |
| 143 | Ex3 | ESI+: 604, 606 [M + H]+<br>NMR-DMSO-d6: 0.89 (3H, t, J = 7.4 Hz), 1.22-1.30 (1H, m), 1.40-1.49 (2H, m), 1.59-1.73 (2H, m), 1.83-2.03 (3H, m), 2.14-2.27 (1H, m), 2.80-2.97 (2H, m), 3.10-3.95 (12H, m), 4.42-4.79 (3H , m), 4.88-4.97 (1H, m), 7.69 (1H, d, J = 1.3 Hz), 7.74 (1H, d, J = 1.3 Hz), 8.52 (1H, s), 8.83 (1H, s), 10.38-11.04 (1H, m), 11.20-11.74 (1H, m), 12.21-13.19 (2H, m) |
| 144 | Ex144 | ESI+: 590, 592 [M + H]+<br>NMR-DMSO-d6: 1.13-1.45 (6H, m), 1.46-2.29 (4H, m), 2.53-2.70 (2H, m), 2.80-3.84 (14H, m), 4.00-5.18 (4H, m), 6.09 (4H, s), 7.57 (1H , s), 7.71 (1H, s), 8.47 (1H, s), 8.79 (1H, d, J = 1.2 Hz), 9.15-10.50 (1H, m), 11.70-12.50 (1H, m) |

INDUSTRIAL APPLICABILITY

The compound of the formula (I) or a salt thereof is a muscarinic $M_3$ receptor-positive allosteric modulator, and can thus be used as an agent for preventing or treating bladder/urinary tract diseases associated with bladder contractions via a muscarinic $M_3$ receptor.

The invention claimed is:

1. A compound of formula (I) or a salt thereof:

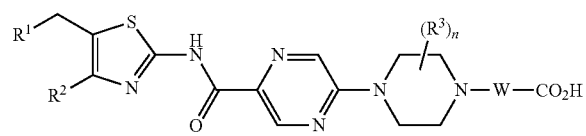

(I)

wherein
$R^1$ is —N(—$R^{12}$)(—$R^{12}$), or optionally-substituted cyclic amino,
$R^{11}$ is $C_{1-6}$ alkyl,
$R^{12}$ is optionally-substituted $C_{1-6}$ alkyl, or optionally-substituted $C_{3-8}$ cycloalkyl,
$R^2$ is optionally-substituted aryl, optionally-substituted monocyclic aromatic hetero ring, or optionally-substituted bicyclic aromatic hetero ring,
each $R^3$ if present is, independently, $C_{1-6}$ alkyl,
W is $C_{1-6}$ alkylene, and
n is an integer of 0 to 4.

2. The compound or a salt thereof according to claim 1, wherein
$R^1$ is cyclic amino optionally substituted with 1 to 5 of a substituent G and/or an oxo substituent, or $R^1$ is —N(—$R^{11}$)(—$R^{12}$),
$R^{11}$ is $C_{1-6}$ alkyl
$R^{12}$ is $C_{1-6}$ alkyl optionally substituted with 1 to 3 substituents selected from the group consisting of
—OH,
—O—$C_{1-6}$ alkyl optionally substituted with at least one group selected from the group consisting of —OH, —O—($C_{1-6}$ alkyl), —CN, —$SO_2$—($C_{1-6}$ alkyl), and halogen,
$C_{3-8}$ cycloalkyl,
—O—($C_{3-8}$ cycloalkyl),
halogen,
—CN, and
a saturated hetero ring,
$R^2$ is phenyl optionally substituted with 1 to 5 substituents G, thienyl optionally substituted with 1 to 3 substituents G, pyridyl optionally substituted with 1 to 3 substituents G, or benzothienyl optionally substituted with 1 to 5 substituents G, and
each substituent G is a substituent selected from the group consisting of:
$C_{1-6}$ alkyl optionally substituted with at least one group selected from the group consisting of —OH, —O—($C_{1-6}$ alkyl), —CN, —$SO_2$—($C_{1-6}$ alkyl), and halogen,
—OH,
—O—$C_{1-6}$ alkyl optionally substituted with at least one group selected from the group consisting of —OH, —O—($C_{1-6}$ alkyl), —CN, —$SO_2$—($C_{1-6}$ alkyl), and halogen,
$C_{3-8}$ cycloalkyl,
—O—($C_{3-8}$ cycloalkyl),
halogen,
—CN,
—$SO_2$—($C_{1-6}$ alkyl),
—$CO_2$—($C_{1-6}$ alkyl),
—COOH,
—CO—N($C_{1-6}$ alkyl)$_2$,
—CO—NH($C_{1-6}$ alkyl),
—$CONH_2$,
—CO—($C_{1-6}$ alkyl),
—$SO_2$—N($C_{1-6}$ alkyl)$_2$,
—$SO_2$—NH($C_{1-6}$ alkyl),
—$SO_2NH_2$,
—N($C_{1-6}$ alkyl)$_2$,
—NH($C_{1-6}$ alkyl),
—$NH_2$,
a saturated hetero ring, and
—O-saturated hetero ring.

3. The compound or a salt thereof according to claim 2, wherein
$R^1$ is pyrrolidin-1-yl or piperidin-1-yl, each substituted with 1 to 2 substituents selected from the group consisting of $C_{1-6}$ alkyl and halogeno-$C_{1-6}$ alkyl, or wherein $R^1$ is —N(—$R^{11}$)(—$R^{12}$),
$R^{11}$ is $C_{1-6}$ alkyl, and
$R^{12}$ is $C_{1-6}$ alkyl optionally substituted with one group selected from the group consisting of $C_{3-8}$ cycloalkyl and —O—($C_{1-6}$ alkyl),
$R^2$ is
phenyl optionally substituted with 1 to 3 groups selected from the group consisting of $C_{1-6}$ alkyl, halogeno-$C_{1-6}$ alkyl, —O—($C_{1-6}$ alkyl), —O-(halogeno-$C_{1-6}$ alkyl), halogen, $C_{3-8}$ cycloalkyl, and —CN;
thienyl optionally substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen;
pyridyl optionally substituted with 1 to 3 groups selected from the group consisting of $C_{1-6}$ alkyl, halogeno-$C_{1-6}$ alkyl, —O—($C_{1-6}$ alkyl), $C_{3-8}$ cycloalkyl, and halogen; or
benzothienyl,
W is $C_{1-3}$ alkylene, and
n is 0 or 1.

4. The compound or a salt thereof according to claim 3, wherein
  $R^2$ is phenyl di-substituted with trifluoromethyl and fluoro, thienyl mono-substituted with trifluoromethyl or chloro, or pyridyl di-substituted with trifluoromethyl and methoxy, and
  W is methylene or ethylene.

5. The compound or a salt thereof according to claim 3, wherein
  $R^1$ is pyrrolidin-1-yl or piperidin-1-yl, each substituted with 1 to 2 substituents selected from the group consisting of $C_{1-6}$ alkyl and halogeno-$C_{1-6}$ alkyl,
  $R^2$ is thienyl optionally substituted with 1 or 2 substituents selected from the group consisting of halogeno-$C_{1-6}$ alkyl and halogen, or wherein $R^2$ is phenyl optionally substituted with 1 or 2 substituents selected from the group consisting of halogeno-$C_{1-6}$ alkyl and halogen, and
  W is methylene or ethylene.

6. The compound or a salt thereof according to claim 1, wherein the compound is a compound selected from the group consisting of:
  3-[(2S)-4-(5-{[4-(4-chlorothiophen-2-yl)-5-{[(2R)-2-methylpyrrolidin-1-yl]methyl}-1,3-thiazol-2-yl]carbamoyl}pyrazin-2-yl)-2-methylpiperazin-1-yl]propanoic acid,
  3-[(3R)-4-{5-[(4-[3-fluoro-5-(trifluoromethyl)phenyl]-5-{[(2R)-2-methylpyrrolidin-1-yl] methyl}-1,3-thiazol-2-yl)carbamoyl]pyrazin-2-yl}-3-methylpiperazin-1-yl]propanoic acid,
  [(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]acetic acid,
  3-(4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}piperazin-1-yl)propanoic acid,
  3-[(2R)-4-(5-{[4-(4-chlorothiophen-2-yl)-5-{[(2R)-2-ethylpyrrolidin-1-yl]methyl}-1,3-thiazol-2-yl]carbamoyl}pyrazin-2-yl)-2-methylpiperazin-1-yl]propanoic acid,
  3-[(3R)-3-methyl-4-{5-[(5-{[(2R)-2-methylpyrrolidin-1-yl]methyl}-4-[4-(trifluoromethyl)thiophen-2-yl]-1,3-thiazol-2-yl)carbamoyl]pyrazin-2-yl}piperazin-1-yl]propanoic acid,
  3-(4-{5-[(5-{[(2R,5R)-2,5-dimethylpyrrolidin-1-yl]methyl}-4-[3-fluoro-5-(trifluoromethyl)phenyl]-1,3-thiazol-2-yl)carbamoyl]pyrazin-2-yl}piperazin-1-yl)propanoic acid, and
  3-{(2R)-4-[5-({5-[(diethylamino)methyl]-4-[3-fluoro-5-(trifluoromethyl)phenyl]-1,3-thiazol-2-yl}carbamoyl)pyrazin-2-yl]-2-methylpiperazin-1-yl}propanoic acid.

7. A pharmaceutical composition, comprising:
  the compound or a salt thereof according to claim 1; and
  a pharmaceutically acceptable excipient.

8. A method for treating a bladder/urinary tract disease associated with bladder contractions via a muscarinic $M_3$ receptor, the method comprising:
  administering, to a subject in need thereof, an effective amount of the compound or a salt thereof according to claim 1.

9. The method according to claim 8, wherein the bladder/urinary tract disease associated with bladder contractions via a muscarinic $M_3$ receptor is voiding dysfunction or urine storage dysfunction in underactive bladder, hypotonic bladder, acontractile bladder, detrusor underactivity, or neurogenic bladder.

10. The compound or a salt thereof according to claim 6, wherein the compound is 3-[(2S)-4-(5-{[4-(4-chlorothiophen-2-yl)-5-{[(2R)-2-methylpyrrolidin-1-yl]methyl}-1,3-thiazol-2-yl] carbamoyl}pyrazin-2-yl)-2-methylpiperazin-1-yl]propanoic acid.

11. The compound or a salt thereof according to claim 6, wherein the compound is 3-[(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]propanoic acid.

12. The compound or a salt thereof according to claim 6, wherein the compound is [(3R)-4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}-3-methylpiperazin-1-yl]acetic acid.

13. The compound or a salt thereof according to claim 6, wherein the compound is 3-(4-{5-[(4-[3-fluoro-5-(trifluoromethyl)phenyl]-5-{[(2R)-2-methylpyrrolidin-1-yl]methyl}-1,3-thiazol-2-yl)carbamoyl]pyrazin-2-yl}piperazin-1-yl)propanoic acid.

14. The compound or a salt thereof according to claim 6, wherein the compound is 3-[(2R)-4-(5-{[4-(4-chlorothiophen-2-yl)-5-{[(2R)-2-ethylpyrrolidin-1-yl]methyl}-1,3-thiazol-2-yl] carbamoyl}pyrazin-2-yl)-2-methylpiperazin-1-yl]propanoic acid.

15. The compound or a salt thereof according to claim 6, wherein the compound is 3-[(3R)-3-methyl-4-{5-[(5-{[(2R)-2-methylpyrrolidin-1-yl]methyl}-4-[4-(trifluoromethyl)thiophen-2-yl]-1,3-thiazol-2-yl)carbamoyl]pyrazin-2-yl}piperazin-1-yl]propanoic acid.

16. The compound or a salt thereof according to claim 6, wherein the compound is 3-(4-{5-[(5-{[(2R,5R)-2,5-dimethylpyrrolidin-1-yl]methyl}-4-[3-fluoro-5-(trifluoromethyl)phenyl]-1,3-thiazol-2-yl)carbamoyl]pyrazin-2-yl}piperazin-1-yl)propanoic acid.

17. The compound or a salt thereof according to claim 6, wherein the compound is 3-{(2R)-4-[5-({5-[(diethylamino)methyl]-4-[3-fluoro-5-(trifluoromethyl)phenyl]-1,3-thiazol-2-yl}carbamoyl)pyrazin-2-yl]-2-methylpiperazin-1-yl}propanoic acid.

* * * * *